US007947739B2

(12) United States Patent
Moore et al.

(10) Patent No.: US 7,947,739 B2
(45) Date of Patent: May 24, 2011

(54) TRANEXAMIC ACID FORMULATIONS

(75) Inventors: Keith A. Moore, Loveland, OH (US);
Ralph A. Heasley, Webster Grove, MO (US); Jeffrey S. Greiwe, Ft. Thomas, KY (US); John W. Facemire, Douglasville, GA (US); Jason D. Modest, Minneapolis, MN (US)

(73) Assignee: Ferring B.V., Hoofddorp (NL)

( * ) Notice: Subject to any disclaimer, the term of this patent is extended or adjusted under 35 U.S.C. 154(b) by 0 days.

(21) Appl. No.: 12/714,181

(22) Filed: Feb. 26, 2010

(65) Prior Publication Data
US 2010/0143468 A1 Jun. 10, 2010

Related U.S. Application Data

(63) Continuation of application No. 12/433,510, filed on Apr. 30, 2009, which is a continuation-in-part of application No. 12/228,489, filed on Aug. 13, 2008, which is a continuation of application No. 11/072,194, filed on Mar. 4, 2005, now abandoned.

(60) Provisional application No. 60/550,113, filed on Mar. 4, 2004, provisional application No. 60/592,885, filed on Jul. 30, 2004.

(51) Int. Cl.
*A61K 31/19* (2006.01)
*A61K 31/195* (2006.01)
(52) U.S. Cl. ........................... 514/574; 514/561
(58) Field of Classification Search .................. 514/561, 514/574
See application file for complete search history.

(56) References Cited

U.S. PATENT DOCUMENTS

| | | | |
|---|---|---|---|
| 4,171,377 A | 10/1979 | Green et al. |
| 4,258,030 A | 3/1981 | Sasaki et al. |
| 4,465,662 A | 8/1984 | Sato et al. |
| 4,483,867 A | 11/1984 | Svahn et al. |
| 4,711,782 A | 12/1987 | Okada |
| 5,229,135 A | 7/1993 | Phillipon et al. |
| 5,242,337 A | 9/1993 | Greenwood et al. |
| 5,271,945 A | 12/1993 | Yoshioka |
| 5,506,264 A | 4/1996 | Fujimara et al. |
| 5,575,987 A | 11/1996 | Kamei et al. |
| 5,622,657 A | 4/1997 | Takada et al. |
| 5,650,174 A | 7/1997 | Muhammad et al. |
| 5,723,269 A | 3/1998 | Akagi et al. |
| 5,747,030 A | 5/1998 | Kohnert et al. |
| 5,807,583 A | 9/1998 | Kristensen et al. |
| 5,858,411 A | 1/1999 | Nakagami et al. |
| 5,874,463 A | 2/1999 | Ancira |
| 5,897,910 A | 4/1999 | Rosenberg |
| 6,051,253 A | 4/2000 | Zettler |
| 6,066,339 A | 5/2000 | Stark et al. |
| 6,113,943 A | 9/2000 | Okada et al. |
| 6,120,802 A | 9/2000 | Breitenbach |
| 6,159,502 A | 12/2000 | Russell Jones |
| 6,197,331 B1 | 3/2001 | Lerner et al. |
| 6,300,369 B1 | 10/2001 | Ancira |
| 6,433,215 B1 | 8/2002 | Jung et al. |
| 6,548,084 B2 | 4/2003 | Leonard et al. |
| 6,551,616 B1 | 4/2003 | Notario et al. |
| 7,192,608 B2 | 3/2007 | Ochiai |
| 7,235,530 B2 | 6/2007 | Blair et al. |
| 7,351,740 B2 | 4/2008 | Zerangue |
| 2002/0132855 A1 | 9/2002 | Nelson et al. |
| 2003/0190353 A1* | 10/2003 | Oosterbaan et al. .......... 424/465 |
| 2004/0006021 A1 | 1/2004 | Rojkjaer et al. |
| 2004/0096499 A1 | 5/2004 | Vaya |
| 2004/0258753 A1 | 12/2004 | Demeesteer |
| 2005/0025825 A1 | 2/2005 | Heasley et al. |
| 2005/0059742 A1 | 3/2005 | Jabbour et al. |
| 2005/0244495 A1 | 11/2005 | Moore et al. |
| 2005/0245614 A1 | 11/2005 | Moore et al. |
| 2005/0267014 A1 | 12/2005 | Rojkaer et al. |
| 2006/0003006 A1 | 1/2006 | Remon |
| 2006/0018933 A1 | 1/2006 | Vaya et al. |
| 2006/0018934 A1 | 1/2006 | Vaya |
| 2006/0127476 A1 | 6/2006 | Heasley et al. |
| 2006/0193914 A1 | 8/2006 | Ashworth |
| 2006/0287258 A1 | 12/2006 | Jabbour et al. |
| 2007/0020335 A1 | 1/2007 | Chen et al. |
| 2007/0027210 A1 | 2/2007 | Zerangue et al. |
| 2008/0193414 A1 | 8/2008 | Proudfoot |
| 2008/0280981 A1 | 11/2008 | Moore et al. |
| 2009/0017114 A1 | 1/2009 | Moore et al. |
| 2009/0048341 A1 | 2/2009 | Moore et al. |
| 2009/0209646 A1 | 8/2009 | Moore et al. |
| 2009/0214644 A1 | 8/2009 | Heasley et al. |
| 2009/0215898 A1 | 8/2009 | Moore et al. |
| 2010/0280117 A1 | 11/2010 | Patrick et al. |

FOREIGN PATENT DOCUMENTS

CA 2086565 7/1994

(Continued)

OTHER PUBLICATIONS

Wellington et al 'Tranexamic Acid, A Review of its Use in the Management of Menorrhagia' Drugs, 63(13), p. 1417-1433, 2003.*
Bravo et al 'In-Vitro Studies of Diclofenac Sodium Controlled-release from Biopolymeric Hydrophilic Matrices' Journal of Pharmacy and Pharmaceutical Science, 5(3), p. 213-219, 2002.*
Florence et al 'Novel Oral Drug Formulation, Their Potential in Modulating Adverse Effects' Drug Safety, 10(3), p. 233-266, 1994.*
Cyklokapron® Package Insert, Pharmacia & Upjohn. Revised Oct. 2000, 6 pgs.
Cyklokapron® Package Insert, Pharmacia Canada, Inc., Misissauga, Ontario, (Nov. 2002).
Lee et al., "Treatment of Menorrhagia with Tranxamic Acid", *Fertility and Sterility*, Oct. 18, 1997, Supple. 1, p. 96.
Shin-Yakuzaigaku Souron (New General Pharmaceutics), Nankodo, revised edition vol. 3, Apr. 10, 1987, pp. 287-291 (Note: An English translation of Table 10.2 is included), 6 pgs.
Stirrat, Gordon M., "Choice of treatment for menorrhagia", *The Lancet*, Jun. 26, 1999, vol. 353, pp. 2175-2176.

(Continued)

*Primary Examiner* — Brandon Fetterolf
*Assistant Examiner* — Christopher R Stone
(74) *Attorney, Agent, or Firm* — Fish & Richardson P.C.

(57) ABSTRACT

Disclosed are modified release oral tranexamic acid formulations and methods of treatment therewith.

19 Claims, 7 Drawing Sheets

FOREIGN PATENT DOCUMENTS

| | | |
|---|---|---|
| EP | 0 998 916 A1 | 5/2000 |
| EP | 0998916 | 5/2000 |
| EP | 0 923 934 B1 | 8/2003 |
| EP | 0923934 | 8/2003 |
| EP | 1 586 315 | 10/2005 |
| GB | 2073019 | 10/1981 |
| JP | 57059847 | 4/1982 |
| JP | 4-243825 | 8/1992 |
| JP | 621994 | 8/1994 |
| JP | 06219942 | 8/1994 |
| JP | 07206660 | 8/1995 |
| JP | 9077726 | 3/1997 |
| JP | 09124878 | 5/1997 |
| JP | 09255542 | 9/1997 |
| JP | 10-017497 | 1/1998 |
| JP | 2000-159674 | 6/2000 |
| JP | 2001-163774 | 6/2001 |
| JP | 2002-265358 | 9/2002 |
| WO | 9415904 | 7/1994 |
| WO | WO96/19200 | 6/1996 |
| WO | 2004028503 | 4/2004 |
| WO | WO 2004/028503 | 4/2004 |
| WO | WO2004/060364 | 7/2004 |
| WO | WO2005/011650 | 2/2005 |
| WO | WO2006/023000 | 3/2006 |
| WO | WO2006/023001 | 3/2006 |
| WO | 2008111096 | 9/2008 |
| WO | 2008148798 | 12/2008 |

OTHER PUBLICATIONS

Notice of Rejection dated Sep. 29, 2009 for Japanese Appln. No. 2006-521917 (with English translation), 25 pgs.
Final Rejection dated Oct. 12, 2010 for Japanese Appln No. 2006-521917 (with English translation), 6 pgs.
Notice of Rejection dated Sep. 3, 2010 for Japanese Appln. No. 2007-523555 (with English translation), 11 pgs.
Notice of Rejection dated Aug. 17, 2010 for Japanese Appln. No. 2007-523556 (with English translation), 11 pgs.
Office Action (Restriction Requirement) dated Feb. 14, 2008 for U.S. Appl. No. 11/072,194, 7 pgs.
Office Action (Restriction Requirement) dated Jul. 20, 2010 for U.S. Appl. No. 12/228,489, 5 pgs.
Office Action (Non-Final) dated Nov. 8, 2010 for U.S. Appl. No. 12/228,489, 16 pgs.
Office Action (Restriction Requirement) dated Nov. 27, 2007 for U.S. Appl. No. 11/072,162, 9 pgs.
Office Action (Non-Final) dated Jan. 23, 2008 for U.S. Appl. No. 11/072,162, 6 pgs.
Office Action (Final Rejection) dated Sep. 9, 2010 for U.S. Appl. No. 12/220,241, 8 pgs.
Office Action (Non-Final) dated Feb. 5, 2010 for U.S. Appl. No. 12/220,241, 7 pgs.
Office Action (Restriction Requirement) dated Oct. 20, 2009 for U.S. Appl. No. 12/220,241, 9 pgs.
Office Action (Examiner Interview Summary Record) dated Oct. 28, 2008 for U.S. Appl. No. 10/631,371, 2 pgs.
Office Action (Non-Final) dated Mar. 13, 2008 for U.S. Appl. No. 10/631,371, 7 pgs.
Advisory Action dated Oct. 23, 2007 for U.S. Appl. No. 10/631,371, 3 pgs.
Office Action (Final Rejection) dated Jun. 14, 2007 for U.S. Appl. No. 10/631,371, 9 pgs.
Office Action (Non-Final) dated Dec. 15, 2006 for U.S. Appl. No. 10/631,371, 6 pgs.
Office Action (Restriction Requirement) dated Aug. 25, 2006 for U.S. Appl. No. 10/631,371, 6 pgs.
Office Action (Restriction Requirement) dated Feb. 17, 2010 for U.S. Appl. No. 12/433,408, 8 pgs.
Office Action (Non-Final) dated Jul. 30, 2010 for U.S. Appl. No. 12/433,408, 7 pgs.
Office Action (Final Rejection) dated Dec. 6, 2010 for U.S. Appl. No. 11/346,710, 12 pgs.
Office Action (Non-Final) dated Mar. 18, 2010 for U.S. Appl. No. 11/346,710, 9 pgs.
Office Action (Restriction Requirement) dated Aug. 17, 2009 for U.S. Appl. No. 11/346,710, 7 pgs.
Office Action (Non-Final) dated May 10, 2010 for U.S. Appl. No. 12/433,510, 9 pgs.
Office Action (Non-Final) dated Oct. 28, 2010 for U.S. Appl. No. 12/433,510, 11pgs.
EMEA, "Committee for Proprietary Medicinal Products Opinion Following an Article 10 Referral CYKLO-f (Tranexamic acid)", EMEA Jul. 27, 2000, pp. 1-9.
Product Information Cyklokapron® Pfizer Australia, most recent amendment Mar. 11, 2008, pp. 1-8.
Package Leaflet: Information for the user, Cyklonova 500mg film-coated tablet. Leaflet approved Dec. 12, 2005. pp. 1-3.
1996 Physician's Desk Reference, 50th Edition, on Tranexamic acid (Cyklokapron), pp. 1950-1951.
Pilbrandt, A., et al., "Pharmaceutical and Bioavailability of Tranexamic Acid", Eur. J. Clin. Pharmacol. (1981)-20: 65-72.
International Search Report from PCT/US2004/023528, (2004).
International Search Report from PCT/US2005/20558, (2005).
International Search Report from PCT/US2005/20563, (2005).
Alexander, D. A. et al, "Randomized trial comparing hysterectomy with endometrial ablation for dysfunctional uterine bleeding: psychiatric and psychosocial aspects," *BMJ*, 1996, 312: 280-284.
Busija, L. et al, "Magnitude and meaningfulness of change in SF-36 scores in four types of orthopedic surgery", Health and Quality of Life Outcomes, 2008, 6:55.
Cella, D., Mayo Clinic Proc. vol. 77(4), Apr. 2002,384-392.
Cooper, Jay, MD et al, "A randomized, multicenter trial of safety and efficacy of the Nova Sure System in the treatment of Menorrhagia," *J Am Assoc Gynecol Laparosc*, 2002; 9 (4): 418-428.
Coulter, Angela et al, "Sharing decisions with patients: is the information good enough?" *BMJ*, 1999; 318: 318-322.
Chauhan, Cynthia, "Denouement: A Patient-Reported Observation," *Value in Health*, 2007; 10: suppl 2, 1098-3015/07/S146.
Crosignani, Pier Giorgio, MD et al, "Levonorgestrel-Releasing Intrauterine Device versus Hysteroscopic Endometrial Resection in the Treatment of Dysfunctional Uterine Bleeding," *Obstet Gynecol*, 1997, 90: No. 2.
Crosignani, Pier Giorgio, MD et al, "Endometrial resection versus vaginal hysterectomy for menorrhagia: Long-term clinical and quality-of-life Outcomes," *Obstet Gynecol*, 1997, 177: 95-101.
Coulter, A., et al, "Quality of Life and Patient Satisfaction Following Treatment for Menorrhagia," *Family Practice*, 1994; 11: No. 4.
"Committee for Proprietary Medicinal Products (CPMP) Opinion Following an Article 10 Referral. CYKLO-f," Jul. 2000.
Cooper, K., et al, "Comparison of microwave endometrial ablation and transcervical resection of the endometrium for treatment of heave menstrual loss: a randomized trial," *The Lancet*, 1999; 354.
Cooper, K. G. et al, "A randomized comparison of medical and hysterscopic management in women consulting a gynecologist for treatment of heavy menstrual loss," *British Journal of Obstetrics and Gynaecology*, 1997; 104: 1360.
Cooper, Kevin G. et al, "Two-year follow up of women randomized to medical management or transcervical resection of the endometrium for heavy menstrual loss: clinical and quality of life outcomes," *British Journal of Obstetrics and Gynaecology*, Mar. 1999; 106: 258-265.
Draft Guidance: Patient-reported Outcome Measures: Use in Medical Product Development to Support Labeling Claims, Feb. 2006.
Dueck, A., et al, "Meeting on the FDA Draft Guidance on Patient-Reported Outcomes," *Value in Health*, 2007; 10: suppl 2, S64-S65.
EuroQol Group, "Euro-Qol-a new facility for the measurement of health-related quality of life", health Policy, 16 (1990) 199-208.
Fraser, I. S., "Estimating Menstrual Blood Loss in women with Normal and Excessive Menstrual Fluid Volume," *Obstet Gynecol*, 2001; 98: 806-14.
Ferguson, R. J., et al., "Use of the Reliable Change index to evaluate Clinical significance in SF-36 Outcomes", Quality of Life Research, 11:509-6, 2002.
Frost, M.,et al, "What is Sufficient Evidence for the Reliability and Validity of Patient-Reported Outcome Measures?" *Value in Health*, 2007; 10: suppl 2, S94-S105.

Gath, D., et al, "Psychiatric disorder and gynaecological symptoms in middle aged women: a community survey," *British Medical Journal*, 1987; 294: 213.

Guyatt, G. H., MD et al, "Interpreting treatment effects in randomized trials," *BMJ*, 1998; 316.

Guyatt, G. H., MD et al, "Measuring disease-specific quality of life in clinical trials," *CMAJ*, 1986; 134: 889.

Guyatt, G.H., MD et al, "Postscript," *Controlled Clinical Trials*, 1991; 12: 266S-269S.

Garratt, A. M. et al, "The SF 36 health survey questionnaire: an outcome measure suitable for routine use within the NHS?" *British Medical Journal*, 1993; 306.

Garratt, A. M. et al, "SF 36 health survey questionnaire: II: Responsiveness to changes in health status in four common clinical conditions," *Quality in Health Care*, 1994; 3: 186-192.

Hurskainen, R., et al, "Quality of life and cost-effectiveness of levonorgestrel-releasing intrauterine system versus hysterectomy for treatment of menorrhagia: a randomized trial," *The Lancet*, 2001; 357.

Hurskainen, R., et al, "Combined Laboratory and diary method for objective Assessment of menstrual Blood loss"; Acta. Obstet. Gynecol. Scand. 1998, 77; 201-204.

Hays, R. D. et al, "The Rand 36-Item Health Survey 1.0," *Health Economics*, 1993; 2: 217-227.

Hays, j. et al., Effects of Estrogen plus Progestin on health Related Quality of Life: N. Engl. J. Med., 2003, 348: 1839-54.

Jaeschke, R., et al, "Ascertaining the Minimal Clinically Important Difference," *Controlled Clinical Trials*, 1989; 10: 407-415.

Jaeschke, R., et al, "Interpreting Changes in Quality-of-Life Score in N of 1 Randomized Trials," *Controlled Clinical Trials*, 1991; 12: 226S-233S.

Jenkinson, C., et al, "Making sense of ambiguity: evaluation of internal reliability and face validity of the SF 36 questionnaire in women presenting with menorrhagia," *Quality in Health Care*, 1996; 5: 9-12.

Jenkinson, C. et al, "Measuring change over time: a comparison of results from a global single item of health status and the multidimensional SF-36 health status survey questionnaire in patients presenting with menorrhagia," *Quality of Life Survey*, 1994; 3: 317-321.

Jones, G., et al, "Health-related quality of life measurement in women with common benign gynecologic conditions: A systematic review," *AJOG Reviews*, 2002; 187: 501-11.

Juniper, E., et al., "Determining a Minimal Improtant Change in a Disease-Specific Quality of Life Questionaire", J. Clin. Epidemlol. vol. 47, No. 1, 81-87, 1994.

Kadir, R.A. et al, "Quality of life during menstruation in patients with inherited bleeding disorders," *Haemophilia*, 1998; 4: 836-841.

Kennedy, A., et al, "Effects of Decision Aids for Menorrhagia on Treatment Choices, Health Outcomes and Costs," *JAMA*, 2002; 288: 2701-2708.

Kirshner, B., et al, "A Methodological Framework for Assessing Health Indices," *J Chron Dis*, 1985; 38: No. 1, 27-36.

Kjerulff, K. H., et al. "Patient satisfaction with results of hysterectomy", Am. J. Obstet. Gynecol., 2000; 183: 1440-7.

Kuppermann, M., et al, "Effect of Hysterectomy vs Medical Treatment on Health-Related Quality of Life and Sexual Functioning," *JAMA*, 2004; Mar. 2004; 291: No. 12.

Lethaby, A., et al. "Antifibrinolytics for heavy menstrual bleeding," *The Cochrane Collaboration*, 2002; issue 4.

Lamping, D. L. et al, "Development and validation of the menorrhagia outcomes questionnaires," *British Journal of Obstetrics and Gynaecology*, 1998; 105: 766-779.

Lohr, K., et al., evaluating Quality of Life and Health Status Instruments: Development of Scientific Review Criteria, Clin. Therapeutics, vol. 18, No. 5, 1996, 979.

Moos, K., MDQ Form C, published by Western Psychological Services, 1989.

Osoba, D., et al, "Evaluating Health-Related Quality of Life in Cancer Clinical Trials: The National Cancer Institute of Canada Clinical Trials Group Experience," *Value in Health*, 2007; 10: suppl 2, 1098-3015/07/S138.

Patrick, D. L., et al, "Patient-Reported Outcomes to Support Medical Product Labeling Claims: FDA Perspective," *Value in Health*, 2007; 10: suppl 2, 1098-3015/07/S125.

Patrick, D. L., et al, "Assessing the Clinical Significance of health related quality of life (HrQOL) improvements in anaemic cancer patients receiving epotin-alfa", European j. of Cancer, 39(2003) 335-345.

Patrick, D. L., et al. "Quality of Life of Women with Urinary Incontinence, Further development of the incontinence quality of Life Instrument (I-QOL)", Urology, 53: 71-76, 1999.

Philipp, C. S., et al, "Development of a screening tool for identifying women with menorrhagia for haemostatic evaluation," *American Journal of Obstetrics and Gynecology*, 2008; 1998: issue 2, 163.

Revicki, D. A, et al, "Interpreting and Reporting Results Based on Patient-Reported Outcomes," *Value in Health*, 2007; 10: suppl 2, 1098-3015/07/S138.

Reid, P. C., et al., "Assessment of Menstrual Blood Loss using a Pictorial Chart: a Validation Study " British L. Obstetrics and Gynaecology, Mar. 2000, vol. 107, pp. 320-322.

Richter, H. E., et al., "Medroxyprogesterone acetate treatment of abnormal uterine bleeding: Factors predicting satisfaction", Am. J. Obstet. Gynecol, Jul. 2003, pp. 37-42.

Rothman, M.L. et al., "Patient Reported Outcomes: Conceptual Issues", Value in Health, vol. 10 Supp. 2, 2007,pp. S66-S75.

Ruta, D. A. et al, "Patient centered assessment of quality of life for patients with four common conditions, " *Quality in Health Care*, 1999; 8: 22-29.

Ruta, D. A. et al, SF 36 health survey questionnaire: I. Reliability in two patient based studies, *Quality in Health Care*, 1994; 3: 180-185.

Ruta, D. A. et al, Assessment of patients with Menorrhagia: how valid is a structured clinical history as a measure of health status, *Quality of Life Research*, 1995; 4: 33-40.

Sculpher, M.J., et al., "Randomized trial comparing hysterectomy and transcervical endometrial resection: effect on health related quality of life and costs two years after surgery", Br. J, of Obstet. Gynaecol., 1996, 103, 142-149.

Shaw, R. W. et al, "Perceptions of women on the impact of menorrhagia on their health using multi-attribute utility assessment," *British Journal of Obstetrics and Gynaecology*, Nov. 1998; 105: 1155-1159.

Shankar, M. et al, "Review of quality of life: Menorrhagia in women with or without inherited bleeding disorders," *Haemophilia*, 2008; 14: 15-20.

Sloan, J. A., et al. "Analysis and Interpretation of Results Based on Patient Reported Outcomes", ISPOR, Values In Health, 2007, 10, Supp2.,S106-S115.

Sloan, J. A., et al. "The Mayo Clinic manuscript Series Relative to the Discussion Dissemination, and Operationalization of the Food and Drug Administration Guidance on Patient Reported Outcomes ",ISPOR, Values In Health, 2007, 10, Supp2.,S59-S63.

Smith, N. D., "Quality of Life Studies From the Perspective of an FDA Reviewing Statistician", Drug Inf. J. 1993, 27,617-623.

Snyder, C. F., et al., "Patient Reported Outcome Instrument Selection: Designing a Measuring Strategy" ISPOR, Values In Health, 2007, 10, Supp2.,S76-S85.

Spies, J.B., et al., "The UFS-QOL, a New Disease-Specific Symptom and Health-Related Quality of Life Questionnaire for Leiomyomata", Obstet Gynecol 2002, 99: 290-300.

Spies, J.B., et al., "The Fibroid Registry; Symptom and Quality of Life Status 1 Year After Therapy", Obstet Gynecol 2005,106: 1309-18.

Srinil, S., et al., "Treatment of Idiopathic Menorrhagia with Tranexamic Acid", J Med Assoc. Thai 2005; 88(Suppl. 2): S1-6.

Stanford School of Medicine, Div. Imm. & Rheu., "The Health Assessment Questionnaire", Jan. 19, 2001.

Turner, R. R., "Patient-Reported Outcomes: Instrument Development and Selection Issues," ISPOR, *Value in Health*, 2007; 10: supp. 2, S86-S93.

Wallenstein, G., et al, "Development and Validation of the Premenstrual Symptoms Impact Survey (PMSIS): A Disease-Specific Quality of Life Assessment Tool," *Journal of Women's Health*, 2008; 17: No. 3.

Ware, J. E., Jr. et al, "The MOS 36-Item Short-Form Health Survey (SF36)," *Med. Care*, 1992; 30: 473-483.

Warner, P.E. et al, "Menorrhagia I: Measured blood loss, clinical feathers, and outcome in women with heavy periods: A survey with follow-up data," *Am. J. Obstetrics and Gynecology*, 2004; 190: 1216-23.

Warner, P. E. et al, "Menorrhagia II: Is the 80mL blood loss criterion useful in management of complaint of menorrhagia?" *Am. J. Obstetrics and Gynecology*, 2004; 190: 1224-29.

Winkler, U. H., "The effect of tranexamic acid on the quality of life of women with heavy menstrual bleeding," *European J.Obstetrics & Gynecology and Reproductive Biology*, 2001; 99: 238-243.

Wilson, I.B., et al., "Linking Clinical Variables with Health Related Quality of Life: A Conceptual model of Patient Outcomes", JAMA 1995, 273(1), 59-65.

Wyrwich, K. W. et al., "Linking Clinical relevance and Statistical Significance in Evaluating Intra-Individual Changes in health Related quality of Life", Med. Care 1999 37(5), 469-478.

Wyrwich, K. W. et al., "Identifying meaningful intra-individual change standards for health related quality of life measures", J. Evaluation in Clinical Practice,2000, 6, 1, 39-49.

Abbott, J. A., et al. "Quality of Life should Be Considered the Primary outcome for Measuring success of endometrial Ablation", J. Am. Assoc. Gynecol. Laparosc., 2003, 10(4); 491-495.

Ben-Tovim, D. I., et al., "The Influence of Age and Weight on Women's Body Attitudes As measured by the Body Attitudes Questionnaire (BAQ)" j. Psychosomatic Res., 1994,38(5) 477-481.

Carlson, K. J., et al. "The Maine Women's health Study: I. Outcomes of Hysterectomy", Obstet. Gynecol ,1994; 83: 556-65.

Cooper, K. et al, "Five-year follow-up of women randomized to medical management or transcervical resection of the endometrium for heavy menstrual loss: clinical and quality of life outcomes," *Br. J. Obstet. Gynaecol.*, 2001; 108: 1222-1228.

Coulter A., et. al. "Quality of Life and Patent Satisfaction Following Treatment for Menorrhagia "Family Practice, 1994:11(4); 394-401.

Deyo, R.A., et al., "Reproducibility and Responsiveness of Health Status Measures; Statistics and Strategies for Evaluation", Controlled Clinical Trials; 1991, 12, 142S-158S.

Liu, Z., et al., "A Systematic Review Evaluating health-Related Quality of Life, Work Impairment, and Health-Care Costs and Utilization in Abnormal Uterine Bleeding ", ISPOR, Value in health, 2007; 10 (3), 183-194.

Greenberg Quinlan Rosner Research inc, "Survey of Women Who Experience Heavy Menstrual Bleeding" for Nation Women's Health Resource Center, Nov. 15, 2005.

Wiegel, M., et al., "The Female Sexual Function Index (FSFI): Cross Validation and Development of Clinical Cutoff Scores" , J Sex Martial Ther. 2005, 31; 1-20.

Dunn, C.J., et al., "Tranexamic Acid; A Review of its Use in Surgery and Other Indications", Drugs, Jun. 1999. 57 (6); 1005-1032.

Lamping D.L., et al., "Development and Validation of an Audit instrument: the Prostate Outcomes Questionnaire", Br. J. Urology, 1998, 82, 49-62.

Leidy, N. K. et al., "Recommendations for Evaluating the Validity of Quality of Life Claims for Labeling and Promotion ", ISPOR, Value in health, 1999; 2(2), 113-127.

Lydick E., et al., "Interpretation of quality of life changes", Quality of life Research, 1993; 2, 221-226.

McHorney, C. A., et al, "The MOS 36-Item Short-Form Health Survey (SF36) II. Psychometric and Clinical Test of Validity in Measuring Physical and Mental Health Constructs", Med. Care, 1993; 31(3):247-263.

McHorney, C. A., et al, "The MOS 36-Item Short-Form Health Survey (SF36) III. Psychometric and Clinical Test of Data Quality, Scaling Assumptions, and Reliability Across Diverse Patient Groups" , Med. Care, 1994; 32 (1):40-66.

Article: "Health-Related Quality of Life and Activity limitation-Eight States", 1995, MMWR, 1998, 47(7), 134-140.

Pawar, A. et al., "Perceptions about quality of life in a school-based population of adolescents with menorrhagia: implications for adolescents with bleeding disorders", Haemophilia, 2008, 14, 579-583.

Radloff, L. S., "The CES-D Scale: A Self Reported Depression Scale for Research in the General Population", App. Psychological. Measurement, 1977; 1(3), 385-401.

Shapley, M., et al. "Why women consult with increased vaginal bleeding: a case-control study", British Journal of General Practice, 2002,52, 108-113.

Shapley, M., et al. "An epidemiological survey of symptoms of menstrual loss in the community", British Journal of General Practice, 2004, 54; 359-363.

Silverman, E., "Your Drug Target Audience", The Scientist, Oct. 2007; 65-70.

Strik, J., et al., "Sensitivity and Specificity of Observer and Self-Report Questionnaires in major and minor Depression Following Myocardial Infarction" Psychosomatics, 2001: 42: 423-428.

Tapanainen, J. S., "Medical management of Menstrual Disorders" International Congress Series 1266(2004) 63-68.

Testa, M.A., et al., "Methods For Quality of Life Studies", Annu. Rev. Public Health. 1994, 15: 535-59.

Zee, B.C., "Growth Curve model Analysis For Quality of Life Data", Statist. Med., 17, 757-766(1998).

Cote I., et al., "Work Loss Associated With Increased Menstrual Loss in the United States", Obstet Gynecol, 2002; 100; 683-7.

Gorgen, H., et al., "Use of the Levonorgestrel-IUS in the treatment of menorrhagia: assessment of quality of life in Turkish users", Arch Gynecol Obstet, pub. Online Nov. 19, 2008.

Philipp, C. S.et al., "Age and the Prevalence of Bleeding Disorders in Women with Menorrhagia", Obstst Gynecol 2005; 105: 61-6.

Santer, M. et al., "what aspects of periods are most bothersome for women reporting heavy menstrual bleeding? Community survey and qualitative study", BMC Women's Health 2007, 7:8.

Protheroe, J., et al "The role of primary care in the diagnosis and management of menorrhagia: a qualitative study of women with menorrhagia", Primary Health Care Research and Development 2005: 6: 21-22.

Van Den Akker, O., et al. "Psycho physiological Responses in Women Reporting Severe Premenstrual Symptoms" Psychosomatic Medicine 51: 319-328 (1989).

Scientific Advisory Committee, "Assessing health status and quality of life instruments: Attributes and review criteria", Quality of Life Research 11: 193-205, 2002.

Flood, E.M., et al., "Psychometric evaluation of the Osteoporosis Patient Treatment Satisfaction Questionnaire (OPSAT-Q), a novel measure to assess satisfaction with bisphosphonate treatment in postmenopausal women" Health and Quality of Life Outcomes 2006, 4: 42.

New Zealand Working Party Guidelines, "An evidence-based guideline for the management of heavy menstrual bleeding", N Z Medical Journal , 1999, 112; 174-7.

FDA Guidance for Industry: Patient-Reported Outcome Measures: Use in Medical Product Development to Support Labeling Claims; Feb. 2006.

FDA Guidance for Industry: Patient-Reported Outcome Measures: Use in Medical Product Development to Support Labeling Claims; Dec. 2009.

Varner, R. et al., "Medicine or Surgery (MS); a randomized clinical trial comparing hysterectomy and medical treatment in premenopausal women with abnormal bleeding", Controlled Clinical Trials, 25 (2004) 104-118.

De Souza, S.S, et al., "Hemoglobin levels predict quality of life in women with heavy menstrual bleeding", Arch. Gynecol. Obstet., Aug. 20, 2009.

Park, Serena and Farquhar, CM, "A survey of practice preferences and attitudes of the New Zealand Guidelines for the management of heavy menstrual bleeding", Aust NZ J Obstet Gynaecol 2002; 42, 4:376, p. 377-80.

Quantification of Menstrual Blood Loss, Review, The Obstetrician & Gynaecologist, 2004; 6: p. 88-92.

Andersson L., et al, "Special Considerations with Regard to the Dosage of Tranexamic Acid in patients with Chronic Renal Diseases," *Urological Research* 6, 83-88 (1978).

Astedt, B., "Clinical Pharmacology of Tranexamic Acid", Scand. J. Gastroenterol, 1987, 22( Suppl 137), 22-25.

Bonnar J.et al., "Treatment of menorrhagia during menstruation: randomized controlled trial of ethamsylate, mefenamic acid, and tranexamic acid," *BMJ* 1996; 313: 579-82.

Callendar S., et al, "Treatment of Menorrhagia with Tranexamic Acid. A Double-blind Trial," *British Medical Journal*, 1970, 4, 214-216.

CPMP Opinion, *The European Agency for the Evaluation of Medicinal Products Evaluation of Medicines for Human Use*, Jul. 27, 2000—CPMP/902/00.

Dowd N., et al, "Pharmacokinetics of Tranexamic Acid during Cardiopulmonary Bypass," *Anesthesiology*, 2002; 97: 390-99.

Dockeray, C.et al, "The fibrinolytic enzyme system in normal menstruation and excessive uterine bleeding and the effect of tranexamic acid," *Eur. J. Obstet. Gynecol. Reprod. Biol.*, 24 (1987) 309-318.

Dubber, AHC., et al, "Some Properties of the antifibrinolytic active isomer of Amino-Methylclohexane Carboxylic Acid," *The Lancet*, 1964;2:1317-9.

Dubber, AHC. et al, "Amino Methyl Cyclohexane Carboxylic Acid (AMCHA), A New Synthetic Fibrinolytic Inhibitor," *British J Haemat*, 1965; 11: 237.

Eriksson O., et al, "Pharmacokinetics of Tranexamic Acid after Intravenous Administration to Normal Volunteers," *Europ. J. clin. Pharmacol.* 7, 375-380 (1974).

Gleeson, N. C. et al, "The effect of tranexamic acid on measured menstrual loss and endometrial fibinolytic enzymes in dysfunctional uterine bleeding," *Acta Obstet Gynecol Scand* 1994; 73: 274-277.

Hoylaerts, M., et al, "Studies on the Mechanism of the Antifibrinolytic Action of Tranexamic Acid," *Biochimica et Biophysica Acta.* 673 (1981) 75-85.

Kaller H., "Enterale Resorption, Verteilung und Elimination von 4-Ainomethylcyclohexancarbonsäure (AMCHA) und a-Aminocapronsäure (ACS) beim Menschen," *Naunyn-Schmiedeberts Arch. Pharmak. U. exp. Path.* 256, 160-168 (1967).

Lakhani, K. P. et al, "Uterine artery blood flow parameters in women with dysfunctional uterine bleeding and uterine fibroids: the effects of tranexamic acid," *Ultrasound Obstet Gynecol* (1998); 11: 283-285.

Lethaby, A. et al, "Antifibrinolytics for heavy menstrual bleeding (Review)," *The Cochrane Collaboration*, 2002; issue 4.

Lethaby, A. et al, "Antifibrinolytics for heavy menstrual bleeding (Review)," *The Cochrane Collaboration*, 2008; issue24.

Longstaff, C., "Studies on the mechanisms of action of aprotinin and tranexamic acid as plasmin inhibitors and antifibrinolytic agents," *Blood Coagulation and Fibrinolysis*, vol. 5, 1994, pp. 537-542.

Melander, B., et al, "Biochemistry and Toxicology of Amikapron®; The Antifibrinolytically Active Isomer of (AMCHA.) (A Comparative Study with Aminocaproic Acid)," *Acta Pharmacol. et Toxicol.* 1965, 22, 340-352.

Mohri, H., "High Dose of Tranexamic Acid for Treatment of Severe Menorrhagia in Patients with von Willebrand Disease," *Journal of Thrombosis and Thrombolysis*, 14 (3), 255-257, 2002.

Nilsson, L and Rybo, G, "Treatment of Menorrhagia with an Antifibrinolytic Agent, Tranexamic Acid (AMCA)," *Acta obst. Et gynec. Scandinav.*, 46, 572, 1967.

Pilbrant A., et al, "Pharmacokinetcis and Bioavailability of Tranexamic Acid," *Eur J Clin Pharmacol*, (1961) 20: 65-72.

Preston J. T., et al, "Comparative study of tranexamic acid and norethisterone in the treatment of ovulatory menorrhagia," *British Journal of Obstetrics and Gynaecology*, May 1995, vol. 102, pp. 401-406.

Puigdellivol, E. et al, "Pharmacokinetics and absolute bioavailability of intramuscular tranexamic acid in man," *International Journal of Clinical Pharmacology, Therapy and Toxicology*, 1985; 23: No. 6, 298-301.

Rybo G., "Plasminogen Activators in the Endometrium, I. Methodological Apects," *Acta obst. et gynec. Scandinav.* 45, 411, 1966.

Svahn C M, et al, "Absorption of Tranexamic Acid as a Prodrug in Healthy Volunteers," *Arzneim-Forsch/Drug Res.* 38 (I), Nr. 5 (1988).

Svahn, Carl M., "Tranexamic Acid Derivatives with Enhanced Absorption," *J. Med Chem.*, 1986; 29: 448-453.

Tapanainen, Juha S., "Medical management of menstrual disorders," *International Congress Series*, 2004; 1266: 63-68.

Thorsen S., "Differences in the Binding to Fibrin of Native Plasminogen and Plasminogen Modified by Proteolytic Degradation Influence of w-Aminocarboxylic Acids," Biochimica et Biophysica Acta, 393 (1975) 55-65—Elsevier Scientific Publishing Company, Amsterdam.

Vermylen J., et al, "A double blind study of the effect of tranexamic acid in essential menorrhagia." *Throm Diath Haemorrh.*, Dec. 31, 1968; 20(3): 583-587.

Wellington K., et al, "Tranexamic Acid: A Review of its Use in the Management of Menorrhagia," *Drugs*, 2003:63 (13): 1417-1433.

ACOG Practice Bulletin; "Management of anovulatory bleeding, 2000, No. 14", International J. Gynecology obstetrics 72(2001) 263-271.

Andersch, Björn et al, "An Objective Evaluation of Flurbiprofen and Tranexamic Acid in the Treatment of Idiopathic Menorrhagia," *Acta Obstet Gynecol Scand*, 1988; 67: 645-648.

Bonnar J.et al., "Treatment of menorrhagia during menstruation: randomized controlled trial of ethamsylate, mefenamic acid, and tranexamic acid," *BMJ* 1996; 313: 579-82.

Callender S., et al, "Treatment of Menorrhagia with Tranexamic Acid. A Double-blind Trial, " *British Medical Journal*, 1970, 4, 214-216.

Dunn, C. J. et al, "Tranexamic Acid, A Review of its use in surgery and other indications," *Drugs*, 1999; 6: 1005-1032.

Edlund, M., et al, "Reduction of menstrual blood loss in women suffering from idiopathic menorrhagia with a novel antifibrinolytic drug (Kabi2161)," *British Journal of Obstetrics and Gynaecology*, 1995; 102: 913-917.

Hallberg, Leif et al, "Menstrual Blood Loss-A Population Study," *Goran. Acta obst. gynec. Scandinav*, 1966; 45: 320.

Higham, J. M. et al, "Risk-Benefit Assessment of Drugs Used for the Treatment of Menstrual Disorders," *Drug Safety*, 1991; 6(3): 183-191.

Kadir, R. A., et al, "Management of excessive menstrual bleeding in women with hemostatic disorders," *Fertility and Sterility*, 2005; 85(5), 1352-1359.

Kouides, PA et al, "Multisite management study of menorrhagia with abnormal laboratory haemostasis: a prospective crossover study of intranasal desmopressin and oral tranexamic acid," *Br J Haemotol*, 2009; 145(2): 212-220.

Lethaby A, Farquhar C, Cooke I. Antifibrinolytics for heavy menstrual bleeding. *Cochrane Database of Systematic Reviews* 2000, Issue4;. In The Cochrane Library, 2008 Issue 2.

Lockhart, I., "Comments on MHRA Consultation Arm 39; Request to Reclassify CYKLO-F 500 Mg. Tablets (Tranexamic Acid) from Prescription only Medicine (POM) to Pharmacy available (P); royal College of Physicians of Edinburgh, , Feb. 27, 2007.

Mehta, B.C. et al, "Epsilon-Amino-Caproic Acid in the Treatment of Menorrhagia," *Journal of Postgraduate Medicine*, 1977; 23(3): 121-123.

Milsom, I. et al, "A comparison of flurbiprofen, tranexamic acid, and a levonorgestrel-releasing intrauterine contraceptive device in the treatment of idiopathic menorrhagia," *AM J Obstet Gynecol*, 1991; 194: 879-883.

Mohri, H., "High Dose of Tranexamic Acid for Treatment of Severe Menorrhagia in Patients with von Willebrand Disease," *Journal of Thrombosis and Thrombolysis*, 14 (3), 255-257, 2002.

NICE Clinical Guideline 44, "Heavy Menstrual bleeding", Jan. 2007.

National Center for Women's and Children's Health; Heavy Menstrual Bleeding Full Guideline Draft, (Jul. 2006).

Nilsson, L , et al., "Treatment of Menorrhagia with an Antifibrinolytic Agent, Tranexamic Acid (AMCA)," *Acta obst. Et gynec. Scandinav.*, 46, 572, 1967.

Ogston, D, "Current Status of Antifibrinolytic Drugs," *Blood Reviews*, 1989; (3): 1-4.

Ong, Y.L. et al, "Menorrhagia in von Willebrand disease successfully treated with single daily dose tranexamic acid," *Haemophilia*, 1998, 4: 63-65.

Prentice, C.R.M., "Indications for Antifibrinolytic Therapy," *Thrombos. Diathes. Haemorrh. (Stuttg.)*, 1975; 34: 634.

Preston J. T., et al, "Comparative study of tranexamic acid and norethisterone in the treatment of ovulatory menorrhagia," *British Journal of Obstetrics and Gynaecology*, May 1995, vol. 102, pp. 401-406.

Popo, V., MHRA, Consultant Doc.: ARM 39, Request to Reclassify a product from POM to P; Cyklo-F, Feb. 7, 2007.

Ragab, M.I. et al, The Use of Tranexamic Acid (AMCA) in IUDs as an Anti-bleeding agent, *Int.J. Gynaecol Obstet*, 1976; 14:137-141.

Ranzcog, NHC Guidelines, Mar. 1999.

Rybo,"Tranexamic acid therapy—effective treatment in heavy menstrual bleeding." *Therapeutic Advances*, 1991; issue 4.

Shaw, R.W., "Assessment of medical treatments for Menorrhagia," *British Journal of Obstetrics and Gynaecology*, 1994; vol. 101, suppl. 11: 15-18.

Siegel, J.E. et al, "Menorrhagia from a haematologist's point of view. Part II: management," *Haemophilia*, 2002; 8: 339-347.

Srinil, Sukanya, MD, "Treatment of Idiopathic Menorrhagia the Tranexamic Acid," *J Med Assoc Thai*, 2005; 88: suppl 2.

Vermylen J., et al, "A double blind study of the effect of tranexamic acid in essential menorrhagia." *Throm Diath Haemorrh.*, Dec. 31, 1968; 20(3): 583-587.

van Eijkeren, M.A. et al, "Menorrhagia. Current Drug Treatment Concepts," *Drugs*, 1992; 43 (2): 201-209.

Vilos, GA, et al, "Guidelines for the management of abnormal uterine bleeding." J. Obstet. Gynaecol Can., 2001; 23; 704-709.

Wellington K., et al, "Tranexamic Acid: A Review of its Use in the Management of Menorrhagia," *Drugs*, 2003:63 (13): 1417-1433.

Weström, Lars, MD et al, "Effect of Tranexamic Acid (AMCA) in Menorrhagia with Intrauterine Contraceptive Devices," *J. of Reproductive Medicine*, 1970; 5: No. 4.

*Working Party for Guidelines for the Management of Heavy Menstrual Bleeding*. "An evidence-based guideline for the management of heavy menstrual bleeding," NZ Med J; 1999; 112: 174-7.

Ylikorkala, O., et al, "Comparison between antifibrinolytic and antiprostaglandin treatment in the reduction of increased menstrual blood loss in women with intrauterine contraceptive devices," *British Journal of Obstetrics and Gynaecology*, 1983; 90: 87-83.

Siegel, J.E. and Kouides, P.A., Menorrhagia from a haematologist's point of view. Part II: management, Haemophilia (2002), 8, p. 339-347.

Svahn, Carl M. et al, "Tranexamic Acid Derivatives with Enhanced Absorption", Journal of Medicinal Chemistry, 1986, vol. 29, No. 4, p. 448-453.

Marjoribanks, J. et al, "Surgery versus medical therapy for heavy menstrual bleeding (Review)", The Cochrane Library, 2009, Issue 2.

Apgar, Barbara S. et al, "Treatment of Menorrhagia", American Family Physician, Jun. 15, 2007, vol. 75, No. 12, p. 1813-1819.

Siddiquil, Shahnaz Hasan, "Spectrum of Dysfunctional Uterine Bleeding and its Conservative Management", JCPSP 2003, vol. 13 (7):375-377.

Tapanainen, Juha S., "Medical management of menstrual disorders", J.S. Tapanainen/International Congress Series 1266 (2004) 63-68.

Dr. Srinil, Sukanya and Dr. Jaisamrarn, Unnop, "Treatment of idiopathic menorrhagia with tranexamic acid", J Med Assoc Thai, vol. 88, suppl 2, 2005, p. S1-6.

Lee, J. et al., "Treatment of Menorrhagia with Tranexamic Acid," *J. Soc. Obstet. Gynaecol. Can.*, 2000;22(109):794-8.

Bekassy, Z. et al., "Treatment with the Fibrinolytic Inhibitor Tranexamic Acid—Risk for Thrombosis?" *Acta Obstet Gynecol Scand*, 1990; 69: 353-354.

Verstraete, M., "Clinical Application of Inhibitors of Fibrinolysis," *Drugs*, 29: 236-261 (1985).

Cyklokapron, Tranexamic acid tablets and injection, Pharmacia, 2001.

Heavy Menstrual Bleeding, Clinical Guideline, Jan. 2007.

Consultation Document: Arm 30, Request to Reclassify a Product from Pom to P, Safeguarding public health, Medicines and Healthcare products Regulatory Agency, Feb. 7, 2007.

Cycklokapron, Tranexamic acid tablets BP and Tranexamic acid injection BP, Product Monograph, Pfizer Canada Inc. Sep. 10, 2003.

Astedt, B., "Clinical Pharmacology of Tranexamic Acid", Scand J. Gastroenterol 1987, 22 (suppl 137), 22-25.

Ansari, Tariq Mahmood, et al, "Spectrophotometric Determination of Tranexamic Acid in Pharmaceutical Bulk and Dosage Forms", Analytical Sciences, Sep. 2005, vol. 21, p. 1133-35.

Product Information: Cyklokapron Pharmacia; South Africa; 500mg tablets, 500mg IV, 1g effervescent tablets; package insert dated Dec. 1999.

Product Information: Cycklokapron Pharmacia; US, 500mg tablets, injection; package insert dated Oct. 2000.

Product Information: Cyklokapron KabiVitrumAB; US, 500mg tablets and injection; package insert dated Jan. 1987.

Product Information: Cyklonova 500mg film coated tablets; product Information date Oct. 5, 2007.

Product Information: Tranon 500mg film coated tablet, product information approved Apr. 16, 2008.

Product Information: Transamin Capsules, 250mg tablets, 500mg tablets, 50% powder, product information revision Jun. 2005.

Product Information: Transamin Capsures, dated Feb. 1998.

Information Sheet: Transamin Capsules, with Product Information: Transamin Tablets 500mg dated Feb. 1998.

Product Information: Cyklokapron Tablets 500 mg, product authorization Feb. 2005.

Product Information: Cycklo-f 500mg film coated tablet, authorization Jan. 31, 1997.

Product Information: Cyklokapron "Meda, Pfizer," injection, 500mg tablets, dated Oct. 24, 2006.

Product Information: Kalnex Capsules (250mg), tablets (500mg), injection, 1991.

Product Monograph: CykloKapron; Pfizer Canada Control No. 086534; Tranexamic acid tablets BP and Tranexamic acid injection BP date: Sep. 10, 2003, control No. 086534.

Martindale—revision Nov. 28, 2001, Monograph, Tranexamic acid (1726j).

Monograph: British Nat. Formulatry No. 43, 2002 sec. 2.11 Antifibrolytic drugs and haemostatics; Tranexamic acid pp. 123.

Monograph Health Canada; Cyklokapron; solution: for IV Use, date May 2005.

Product Information: Cyklokapron Injection, Ampoules 500mg per 5ml, Pharmacia Limited UK, authorization date Feb. 9, 1987.

Product Information: Cyklokapron tablets and Injection; 100mg/1ml water; Pharmacia & Upjohn revision Jun. 2008.

Product Information: Cyklokapron—tranexamic acid injection solution, 100mg/1ml. Pharmacia & Upjohn revision Jun. 2008.

Quixil solutions for sealant, date of first authorization Sep. 1999.

Crotts, G et al., Development of an enteric coating formulation and process for tablets primarily composed of a highly water soluble organic acid: European. J. Pharmaceutics and Biopharmaceutics 51, (2001), 71-76.

Tsementzis, S.A., et al., "Fibrinolytic Activity After Subarachnoid Haemorrhage and the Effects of Tranexamic Acid," *Acta Neurochir (Wien)*, vol. 103 (1990), pp. 116-121.

Patent Abstracts of Japan Publication No. JP 06219942, *Gelatin Capsule Preparation Mixed With Tranexamic Acid*, Published Aug. 9, 1994.

Patent Abstracts of Japan Publication No. JP 07206660, *External Preparation for Skin*, Published Aug. 8, 1995.

Patent Abstracts of Japan Publication No. JP 09124878, *Gel Composition*, Published May 13, 1997.

Patent Abstracts of Japan Publication No. JP 0925542, *Composition for Oral Cavity Application*, Published Sep. 30, 1997.

Patent Abstracts of Japan Publication No. JP 57059847, *4-Aminomethylcyclohexanecarboxylic Acid Derivative*, Published Apr. 10, 1982.

Walzman, M. and Bonnar, J. Effects of Tranexamic Acid on the Coagulation and Fibrinolytic Systems in Pregnancy Complicated by Placental Bleeding, *New Toxicology for Old Arch. Toxicol.*, Suppl. 5 (1982), pp. 214-220.

Erikkson, O. et al., "Pharmacokinetics of tranexamic acid after intravenous administration to normal volunteers," *Eur. J. Clin. Pharmacol*, 1974;7:375-380.

Berntorp E., "No increased Risk of Venous Thrombosis in Women Taking Tranexamic Acid," *Thromb Haemostat.*, 2001; 86: 714-5.

Sindet-Pedersen, "Distribution of tranexamic acid to plasma and saliva after oral administration and mouth rinsing: a pharmacokinetic study," *J. Clin. Pharmacol.* 1987; 27; 1005.

Physician's Desk Reference, 1996, on Tranexamic acid (Cyklokapron), pp. 1950-1951.

Kriplani, A. et al., "Role of tranexamic acid in management of dysfunctional uterine bleeding in comparison with medroxyprogesterone acetate," *Journal of Obstetrics and Gynaecology*, vol. 26, No. 7 (2006), pp. 673-678.

Demers, Christine et al., "Gynaecological and Obstetric Management of Women with Inherited Bleeding Disorders," *JOGC*, No. 163, Jul. 2005, pp. 707-718.

EMEA, "Committee for Proprietary Medicinal Products Opinion Following an Article 10 Referral CYKLO-f (Tranexamic acid)", EMEA Jul. 27, 2000.

Product Information Cyklokapron® Pfizer Australia, most recent amendment Mar. 11, 2008, pp. 1-8.

Package Leaflet: Information for the user, Cyklonova 500mg film-coated tablet. Leaflet approved Dec. 12, 2005, pp. 1-3.

Investigative report dated Apr. 7, 2010 and prepared by Chief Investigator D.C. Sharma of ClueWise Services, Pvt. LTD. (India) concerning information sought on Mefro Pharmaceuticals and Terrance Pharma (both of India), specifically in relation to a Trexamic Rx product (tranexamic acid) (Reference All).

* cited by examiner

Measure #1
During your most recent menstrual period, your blood loss was:
1. LIGHT   2. MODERATE   3. HEAVY   4. VERY HEAVY

Measure #2
During your most recent menstrual period, how much did your bleeding limit your work outside or inside the home?
1. NOT AT ALL  2. SLIGHTLY  3. MODERATELY
4. QUITE A BIT  5. EXTREMELY

Measure #4
During your most recent menstrual period, how much did you bleeding limit you in your social or leisure activities?
1. NOT AT ALL  2. SLIGHTLY  3. MODERATELY
4. QUITE A BIT  5. EXTREMELY

Measure #3
During your most recent menstrual period, how much did you bleeding limit you in your physical activities?
1. NOT AT ALL  2. SLIGHTLY  3. MODERATELY  4. QUITE A BIT
5. EXTREMELY

Measure #5
Please mark [X] all activities that were limited by bleeding during your recent menstrual period.
- [ ] Walking
- [ ] Standing
- [ ] Climbing Stairs
- [ ] Squatting or bending down
- [ ] Childcare
- [ ] Shopping
- [ ] Home Management
- [ ] Leisure
- [ ] Exercise
- [ ] Sports
- [ ] Gardening
- [ ] Traveling / Vacation
- [ ] Other? _____
- [ ] Other? _____

Measure #6
Compared to your previous menstrual period, would you say your blood loss during this period was:
0. ABOUT THE SAME   1. BETTER (go to 6a)   2. WORSE (go to 6b)

Measure #6a
If you menstrual bleeding 'improved' since your last period, please indicate how much.
7. A VERY GREAT DEAL BETTER
6. A GREAT DEAL BETTER
5. A GOOD DEAL BETTER
4. AN AVERAGE AMOUNT BETTER
3. SOMEWHAT BETTER
2. A LITTLE BETTER
1. ALMOST THE SAME

Measure #6b
If you menstrual bleeding 'worsened' since your last period, please indicate how much.
7. A VERY GREAT DEAL WORSE
6. A GREAT DEAL WORSE
5. A GOOD DEAL WORSE
4. AN AVERAGE AMOUNT WORSE
3. SOMEWHAT WORSE
2. A LITTLE WORSE
1. ALMOST THE SAME, HARDLY WORSE AT ALL

Measure #6c
Was this a meaningful or important change for you?
0. NO    1. YES

FIG. 7

Menorrhagia Impact Measure #1 Percentage of Patients and Normals Indicating Each Response at Baseline (BL) and at Month 1 (M1)

TRANEXAMIC ACID FORMULATIONS

This application is a continuation of U.S. patent application Ser. No. 12/433,510, filed Apr. 30, 2009, which is a continuation-in-part of U.S. patent application Ser. No. 12/228,489, which is a continuation of U.S. patent application Ser. No. 11/072,194 filed Mar. 4, 2005, now abandoned, which claims the benefit of U.S. Provisional Application No. 60/550,113, filed Mar. 4, 2004, and U.S. Provisional Application No. 60/592,885, filed Jul. 30, 2004, the disclosures of which are both hereby incorporated by reference in their entireties.

FIELD OF THE INVENTION

The invention is directed to modified release oral tranexamic acid formulations that preferably minimize or eliminate undesirable side effects and methods of treatment with these formulations.

BACKGROUND OF THE INVENTION

Tranexamic acid (trans-4-(aminomethyl)cyclohexanecarboxylic acid, Cyklokapron® (Pfizer) is an antifibrinolytic agent. That is, it helps to prevent lysis or dissolution of a fibrin clot which forms in the normal physiologic process of hemostasis. Its mechanism of action is as a competitive inhibitor of plasminogen activation, and as a noncompetitive inhibitor of plasmin; both plasminogen and plasmin are activators of fibrinolysis and active clot-lysing agents. Tranexamic acid thus helps to stabilize fibrin clots, which in turn maintains coagulation and helps to control bleeding.

Tranexamic acid is used to control excess bleeding, for example, excess bleeding that occurs during dental procedures in hemophiliacs and for heavy bleeding during menstruation (menorrhagia). Women suffering from menorrhagia are typically treated orally with 500 mg tranexamic acid tablets administered three or four times daily with a total daily dose ranging from 3 grams/day (two tablets every eight hours) to 6 grams/day (three tablets every six hours). However, this treatment may cause adverse gastrointestinal reactions, including nausea, vomiting, diarrhea, and cramping, etc. These gastrointestinal side effects are due to the quantity of tranexamic acid and/or rapid rate of release of tranexamic acid into the stomach with each dose, as well as the large quantity of excipients used in the tablet formulation that are introduced into the stomach. Such side effects, in addition to the cramping, bloating, pain, and other symptoms that may accompany menses, are undesirable, and a formulation of tranexamic acid is needed which will reduce or eliminate these side effects.

Menstrual Bleeding

Menstrual Bleeding disorders encompass a number of conditions including bleeding associated with uterine fibroids, endometriosis, or bleeding as a result of deficiencies in the clotting process for example, von-Willebrand's disease. Studies suggest that as many as 11% of the women who experience heavy menstrual bleeding, suffer from an inherited bleeding disorder such as von Willebrand's disease. Excessive Menstrual Bleeding is menstruation at relatively regular intervals but with excessive blood loss over the menses period which may be prolonged. Heavy Menstrual Bleeding (also referred to as "Menorrhagia") is a serious, persistent, and recurrent medical condition that is one of the most common complaints encountered by gynecologists and primary care physicians (Palep-Singh, 2007). A 2005 survey of 273 obstetrician/gynecologists found that they see an average of 18 to 25 symptomatic patients per month. Heavy Menstrual Bleeding is a hyperfibrinolytic condition defined as cyclic, normal intervals of menstruation with excessive volume. Menorrhagia is often associated with a disruption in daily routines, work, and sexual activity leading to a significant decrease in health-related quality of life and time lost from work or school. While Menorrhagia is rarely life threatening, when undiagnosed and untreated, it may over time cause iron deficiency anemia and increased fatigue, both of which affect normal life activities, relationships, social activities, and various aspects of mental well-being (irritation, anxiety). Left untreated it may be associated with subsequent morbidity including dysmenorrhea, hospitalization, red blood cell transfusions and chronic pain. Annually, approximately 10% of women of reproductive age report Menorrhagia (Rees 1991; van Eijkeren, 1992) and according to the Center for Disease Control (CDC), 3 million women of reproductive age report Menorrhagia yearly, 60% of which have no known etiology. Studies report that as many as thirty percent of premenopausal women perceive their menses to be excessive.

Women suffering from menorrhagia often have greater uterine fibrinolytic activity than women with normal cyclic menstrual blood loss (MBL). High concentrations of plasminogen activators are found in both the uterus and menstrual fluid (Albrechtsen, 1956a,b). Rybo (1966) found significantly higher concentration of endometrial plasminogen activators in women with excessive menstrual bleeding compared to women with normal menstrual loss.

Causes of Menorrhagia include pelvic diseases (myomata [fibroids], adenomyosis or uterine polyps), intrauterine contraceptive devices, and systemic disorders (coagulopathies such as thrombocytopenia or von Willebrand's disease, and hypothyroidism). In contrast to menorrhagia, the term 'dysfunctional uterine bleeding' refers to excessive, prolonged or irregular bleeding from the endometrium that is unrelated to systemic disease (Wathen, 1995), and is usually associated with anovulation. Menorrhagia is also distinguished from other ovulatory bleeding disorders, such as metrorrhagia (intermenstrual bleeding), menometrorrhagia (irregular heavy menstrual bleeding) and polymenorrhea (menstrual cycle less than 21 days).

Diagnosis of Menstrual Blood Loss

In clinical trials, menstrual blood loss (MBL) is usually determined by measuring the amount of hemoglobin recovered from sanitary products during the menstrual cycle, using the alkaline hematin method (Fraser, 1994). However, it is important to remember that blood accounts for only about 50% of total menstrual flow, with endometrial transudate accounting for the remainder (Fraser, 1994). Total menstrual flow can be estimated by weighing of sanitary products or by comparisons with a pictorial blood loss assessment chart. However, the use of these quantitative and semi-quantitative methods is not practical in non-trial settings. Rather, the diagnosis of Menorrhagia in the healthcare clinic is made by medical providers on the basis of patient's perceived and self-reported medical history, routine laboratory assessments of the patient's general health status, and gynecological examinations.

Clinically heavy menstrual bleeding is sometimes defined as total blood loss exceeding about 80 ml per cycle or menses lasting longer than seven days. The volume lost however, varies widely. Clinically losses from about 30 ml to 60 ml, 60 to 80 ml, 80 to 100 ml, to as high as 1000 ml per cycle are observed. Menstrual blood losses of 50 to 60 ml are associated with a negative iron balance and iron deficiency anemia is diagnosed in about 67% of the women who lose an excess of 80 ml per day. Other criteria for diagnosing the condition include measuring the number and size of blood clots in the meneges, or monitoring the use of pads or tampons. It is estimated that perhaps only ten percent of women who perceive their loss to be excessive actually fall within the clinical definition. The 80 ml definition has been repeatedly questioned, and alternative definitions broadened the blood loss range used for patient evaluations.

Blood loss volume assessments commonly require the collection and preservation of menstrual pads or tampons, the extraction of the pads and the accurate measurement of the blood content. Women are instructed to collect all sanitary towels and tampons during the course of the menstrual diagnosis period or the course of a clinical study period. Blood loss can be measured by extraction of the blood from the sanitary material with 5% sodium hydroxide followed with a spectrophotometric measurement of hematin at a wavelength of about 540 nm. The total blood loss can be calculated for an individual by comparison of the patients plasma blood hemoglobin measurement with the collected hemoglobin values.

The collection of the blood sample discourages the routine use of the test in the diagnosis or in the treatment of the condition. In the course of a routine visit with a physician other blood work may be appropriate but lacks a casual relation to the heavy bleeding disorder. The battery of routine laboratory tests may include patient blood hemoglobin, haematocrit, platelet count, bilirubin, serum creatinine and serum ferritin. In sum, diagnosis in the routine course of practice relies heavily on the woman's perception of the volume of blood lost during menses.

Diagnosis and Treatment of Heavy Menstrual Bleeding Disorders (Menorrhagia)

A number of medical and surgical interventions are available to treat menstrual bleeding disorders. Currently available non-surgical treatments for heavy bleeding disorders, include, hormonal treatments (e.g., oral contraceptives), high-dose progestin therapy, desmopressin acetate, ethamsylate, nonsteroidal anti-inflammatory drugs (NSAIDs), the antifibrinolytic drugs aminocaproic acid and tranexamic acid. Even with the drug treatments available, surgery remains a common treatment.

Although not approved for menorrhagia in the US, use of oral contraceptives for menorrhagia is widely accepted. Oral contraceptives may not be a preferred therapy for some women because of age (younger females), unwanted side effects (nausea and vomiting, breakthrough bleeding, weight change, migraines and depression), and safety concerns (increased risk of thromboembolism, stroke, myocardial infarction, hepatic neoplasia and gall bladder disease). High-dose progestin (synthetic versions of the hormone progesterone) may also be given to women with menorrhagia, either orally or by a progestin-releasing device inserted into the uterus (intrauterine device). Side effects include nausea, bloating, mood changes, and breast tenderness.

Although it is typically a last resort, desmopressin acetate is sometimes used to help lighten menstrual flow in women with menorrhagia. The effectiveness of desmopressin is thought to vary between individuals. Side effects include headache, tachycardia, facial flushing, and rare reports of thromboembolism.

NSAIDs are sometimes used to treat menorrhagia as they may reduce blood flow while providing analgesia for pain associated with the condition (Shaw, 1994). Side effects associated with chronic NSAID use include gastrointestinal bleeding, ulceration, and perforation; and renal effects such as hyperkalemia, hyponatremia, acute renal insufficiency, interstitial nephritis, and renal papillary necrosis.

Hysterectomy or endometrial resection are options if other forms of therapy are not effective or are unsuitable for some reason. Possible surgical complications include infection, uterine perforation, and other complications associated with major surgery.

Antifibrinolytic drugs, such as $\epsilon$-aminocaproic acid and tranexamic acid (immediate-release formulation) have been used to treat HMB in women with or without a diagnosed bleeding disorder (van Eijkeren, 1992; Bonnar, 1996; Vermylen, 1968; Nilsson, 1965). The available evidence from published literature suggests that tranexamic acid at doses of ~4 g/day (typically 1 g every 6 hours) is effective in the treatment of HMB and is associated with few side effects (Callender, 1970; Dunn, 1999; Edlund, 1995; Preston, 1995). In Sweden, the average dose of tranexamic acid to treat HMB is 3.9 g/day (Rybo, 1991). Thus, tranexamic acid is used extensively in Europe, Canada, Asia, Japan, Australia and New Zealand to treat menorrhagia, but is not approved for this indication in the US.

Tranexamic acid is a competitive inhibitor of plasminogen activation (see review by Dunn, 1999). Binding of tranexamic acid to plasminogen does not prevent conversion of plasminogen to plasmin by tissue plasminogen activator, but the resulting plasmin/tranexamic acid complex is unable to bind to fibrin. Thus, enzymatic breakdown of fibrin by plasmin (fibrinolysis) is inhibited. At higher concentrations, tranexamic acid is also a noncompetitive inhibitor of plasmin.

Before medical and surgical interventions can be initiated, diagnosis of a heavy menstrual bleeding disorder must be accomplished.

Diagnosis and treatment of disease often depends on the patient's perception and subsequent description of symptoms, the physician's evaluation of the patient's description, the physician observations of the patient and laboratory test results. Menstrual bleeding disorders do not lend themselves to physician observation or to routine laboratory testing. Patient observations and the physician's evaluation of the patient's description are subjective and thus variable. In addition a women's medical history has been found to be a poor predictor of menstrual blood loss. Neither the duration of menses nor the number of sanitary pads worn accurately corresponds to the woman's actual menstrual blood loss (Chimbira, Haynes, year). An objective assessment of blood loss using the alkaline haematin assay has been shown to be reproducible but it is not suited for routine clinical use by healthcare providers. To date no effective instrument for reliably diagnosing and/or monitoring the treatment of menstrual bleeding disorders has been developed despite the significant number of women who suffer from these conditions.

Previously, studies have focused on the impact of symptoms of bleeding disorders on patients' health related quality of life. As the effects of menstrual bleeding disorders are primarily symptomatic, the subjective outcome namely symptom alleviation, cannot be objectively measured. In research from European countries where the antifibrinolytic drug tranexamic acid is currently available, treatment with this antifibrinolytic has reduced heavy menstrual bleeding by 40-50% and improved the health-related quality of life of affected women on measures of social activity, work performance, productivity, cleanliness, overall functioning and tiredness.

Jenkinson et al, Quality in Health Care 1996; 5; 9-12 evaluated the validity and internal reliability of the short form-36 (SF36) health survey questionnaire in women presenting with menorrhagia. The study concluded that several questions on the questionnaire were difficult to answer for patients with heavy menstrual bleeding. Such problems were suggested as possible interferences with the validity of the measure. Jenkinson warns that because a subjective measure works well in one population or with one group, this cannot be taken to imply its appropriateness for all groups or conditions.

Edlund, in an abstract from a seminar on Dysfunctional Uterine Bleeding, Feb. 23, 1994, indicates that a questionnaire was used in a Swedish study of 2205 women who described their menstruation as excessive.

Winkler in a study based in part on the Edlund work, concluded that the treatment of heavy menstrual bleeding with tranexamic acid increased the quality of life of the treated patients. The Winkler study was an open label uncontrolled usage study which included 849 patients. A questionnaire was used prior to treatment and after the first and third menstruation. The study indicates that 80% of the women were satisfied with the treatment. The questionnaire used a series of eight question combined with an assessment by the patients of the change in quantity of menstrual flow.

Ruta, D. A., Quality of Life Research, 4, (33-40), 1995 finds that menorrhagia is a common problem in gynecological practice and that women seek professional help primarily because of the deleterious effect on their quality of life. Ruta recognizing the importance of evaluating the effectiveness of the treatments developed a questionnaire based on the type of questions frequently asked when taking a gynecological history. A series of questions were devised which assessed fifteen factors including the duration of the period, the regularity of the period, pain, problems with soiling/staining, interference with work, interference with leisure. Ruta concluded that the clinical questionnaire may be useful in selecting patients for hysterectomy and assessing the outcome of conservative treatment especially in combination with the SF-36 questionnaire.

Diagnostic Test for Menstrual Bleeding

The alkaline haematine test described above provides quantitative assessments of the extent of menstrual bleeding. This test allows the physician to diagnose and monitor the progress of a women's menstrual process. However the test is impractical and difficult to perform. The test requires women to capture used menstrual pads over the course of her period, preserve the samples in a condition such that the blood content within the pad may be accurately extracted and quantitated. Requesting a patient to perform menses sample collection may be practical in the course of a clinical trial where procedures are specified and monitored however, in routine medical practice, the use of such a test procedure to diagnose and monitor a women's menstrual bleeding is impractical and the data generated is unreliable.

The need remains to develop an assessment system which replaces previously studied diagnostic techniques and the alkaline haematine test and provides a reliable measure of both the occurrence of the disorder and the progress of the disorder. The present invention fills this need by providing a Heavy Menstrual Bleeding Instrument (HMBI) which is capable of diagnosing, and monitoring the treatment of a patient with a menstrual bleeding disorder.

There also remains a need to provide Heavy Menstrual Bleeding (HMB) therapy that is safe, efficacious and only administered during the monthly period of heavy menstruation, addresses the excessive fibrinolysis implicated in many causes of menorrhagia, and fills a currently recognized unmet medical need in the US. Therapy for HMB is expected to reduce the incidence and extent of iron-deficiency anemia, and to provide a nonhormonal medical therapy option in lieu of the numerous invasive procedures (e.g., transcervical endometrial resection) and major surgery (hysterectomy) performed annually.

SUMMARY OF THE INVENTION

Formulations of tranexamic acid which minimize or eliminate the undesirable gastrointestinal side effects in patients on oral tranexamic acid therapy, e.g. women treated for menorrhagia (heavy menstrual bleeding) are disclosed. The present invention is directed in part to a modified release formulation, formulated so that the release of tranexamic acid thereof from the dosage form occurs in a designed fashion to prevent a bolus of tranexamic acid being introduced into the stomach and available for dissolution in the gastric contents. Such modified release formulations reduce the concentration of tranexamic acid dissolved in the stomach contents such as e.g., preventing a large bolus of tranexamic acid being introduced in the stomach. The beneficial effect of this reduced tranexamic acid concentration is to lower the amount of tranexamic acid in the gastric contents so that there are fewer adverse effects with tranexamic acid therapy. This reduction in adverse effects preferably results in improved patient compliance with therapy, because preferably patients will not intentionally miss taking a dose to avoid these adverse side effects. Physicians will also preferably be more likely to initiate and maintain tranexamic acid treatment for their patients because of the reduced patient complaints.

It is an object of the invention to provide an oral dosage form comprising tranexamic acid which is suitable for administration on a two or three times a day basis to humans.

It is a further object of the invention to provide a modified release oral dosage form comprising tranexamic acid and a modified release material which provides for the modified release of the tranexamic acid and is suitable for administration on a two or three times a day basis.

It is a further object of certain embodiments of the present invention to provide a modified release oral dosage form comprising tranexamic acid and a modified release material which minimizes or eliminates the undesirable gastrointestinal side effects in patients on oral tranexamic acid therapy while maintaining or improving the therapeutic effect of tranexamic acid.

It is a further object of certain embodiments of the present invention to provide a method of treating a patient suffering from heavy menstrual bleeding (menorrhagia) by orally administering to the patient one or more dosage forms comprising tranexamic acid and a modified release material which provide(s) for therapeutically effective levels of tranexamic acid suitable for two or three times a day administration.

The above advantages and objects and others can be achieved by virtue of the present invention which is directed in part to a modified release oral dosage form comprising tranexamic acid or a pharmaceutically acceptable salt thereof and a modified release material which provides for the modified release of the tranexamic acid or pharmaceutically acceptable salt thereof from the dosage form such that the dosage form is suitable for administration on a two or three times a day basis; said dosage form providing an in-vitro dissolution release rate of the tranexamic acid or pharmaceutically acceptable salt thereof, when measured by a USP 27 Apparatus Type II Paddle Method @ 50 RPM in 900 ml water at 37±0.5° C., of less than about 70% by weight tranexamic acid or pharmaceutically acceptable salt thereof released at about 45 minutes and about 100% by weight of said tranexamic acid or pharmaceutically acceptable salt thereof released by about 120 minutes.

In certain embodiments, the present invention is directed to a method of treating a patient in need of tranexamic acid or pharmaceutically acceptable salt thereof therapy comprising administering to the patient about 1300 mg of tranexamic acid or pharmaceutically acceptable salt thereof in at least one oral dosage form comprising said tranexamic acid or pharmaceutically acceptable salt thereof and a modified release material which provides a mean maximum plasma concentration ($C_{max}$) of tranexamic acid of from about 5 to about 17.5 mcg/ml, preferably from about 6.5 to about 15 mcg/ml, more preferably from about 9 to about 14.5 mcg/ml after single dose oral administration to humans.

In certain embodiments, the invention is further directed to a method of treating a patient in need of tranexamic acid or pharmaceutically acceptable salt thereof therapy comprising administering to the patient about 1300 mg of tranexamic acid or pharmaceutically acceptable salt thereof in at least one oral dosage form comprising said tranexamic acid or pharmaceutically acceptable salt thereof and a modified release material which provides a mean maximum plasma concentration ($C_{max}$) of tranexamic acid of from about 5 to about 25 mcg/ml, preferably from about 10 to about 20 mcg/ml, more preferably from about 12.5 to about 17.5 mcg/ml, most preferably about 15 to about 17 mcg/ml after steady state oral administration to humans.

In certain embodiments, the modified release oral dosage form of the present invention provides a mean $T_{max}$ of tranexamic acid at from about 1 to about 5.5 hours, preferably at from about 2 to about 4 hours, more preferably at from about 2 to about 3.5 hours after oral administration of the dosage form to humans.

In certain embodiments, the invention is further directed to a modified release oral dosage form comprising tranexamic acid or pharmaceutically acceptable salt thereof and a modified release material which provides for the modified release of the tranexamic acid or pharmaceutically acceptable salt thereof from the dosage form such that the dosage form is suitable for administration on a two or three times a day basis and the dosage form provides a dissolution release rate in-vitro of the tranexamic acid or pharmaceutically acceptable salt thereof when measured by the USP 27 Apparatus Type II Paddle Method @ 50 RPM in 900 ml water at 37±0.5° C. of less than about 40% by weight tranexamic acid or pharmaceutically acceptable salt thereof released at about 15 minutes, less than about 70% by weight tranexamic acid or pharmaceutically acceptable salt thereof released at about 45 minutes, and not less than 50% by weight tranexamic acid or pharmaceutically acceptable salt thereof released at about 90 minutes.

In certain embodiments, the invention is further directed to a modified release oral dosage form comprising tranexamic acid or pharmaceutically acceptable salt thereof and a modified release material which provides for the modified release of the tranexamic acid or pharmaceutically acceptable salt thereof from the dosage form such that the dosage form is suitable for administration on a two or three times a day basis and the dosage form provides a dissolution release rate in-vitro of the tranexamic acid or pharmaceutically acceptable salt thereof when measured by the USP 27 Apparatus Type II Paddle Method @ 50 RPM in 900 ml water at 37±0.5° C. of about 0% to about 40% by weight tranexamic acid or pharmaceutically acceptable salt thereof released at about 15 minutes, from about 20% to about 60% by weight tranexamic acid or pharmaceutically acceptable salt thereof released at about 30 minutes, from about 40% to about 65% by weight tranexamic acid or pharmaceutically acceptable salt thereof released at about 45 minutes, from about 50% to about 90% by weight tranexamic acid or pharmaceutically acceptable salt thereof release at about 60 minutes, and not less than 60% by weight tranexamic acid or pharmaceutically acceptable salt thereof released at about 90 minutes.

In certain embodiments, the invention is further directed to a modified release oral dosage form comprising tranexamic acid or pharmaceutically acceptable salt thereof and a modified release material, which provides for a bioavailability of tranexamic acid of greater than 40%, from about 41% to about 60%, preferably from about 42% to about 50%, more preferably about 45% after oral administration to humans.

In certain embodiments, the present invention is further directed to a modified release oral dosage form comprising from about 585 to about 715 mg of tranexamic acid or pharmaceutically acceptable salt thereof, preferably about 650 mg of tranexamic acid or pharmaceutically acceptable salt thereof, and a modified release material which provides for the modified release of the tranexamic acid or pharmaceutically acceptable salt thereof from the dosage form such that the dosage form is suitable for administration on a two or three times a day basis.

In certain embodiments, the present invention is directed to a modified release oral dosage form comprising tranexamic acid or pharmaceutically acceptable salt thereof and a modified release material which provides for the modified release of the tranexamic acid or pharmaceutically acceptable salt thereof from the dosage form such that the dosage form is suitable for administration on a two or three times a day basis, the dosage form providing a reduction of at least one side effect selected from the group consisting of headache, nausea, vomiting, diarrhea, constipation, cramping, bloating, and combinations thereof, as compared to an equivalent amount of tranexamic acid or pharmaceutically acceptable salt thereof in an immediate release oral dosage form when administered across a patient population.

In certain embodiments, the present invention is directed to a modified release oral dosage form comprising tranexamic acid or pharmaceutically acceptable salt thereof and a modified release excipient, said dosage form providing for the release of the tranexamic acid or pharmaceutically acceptable salt thereof which is slower than an immediate release oral dosage form and faster than a controlled release oral dosage form, such that the modified release oral dosage form is suitable for administration two or three times a day.

In certain embodiments, the invention is further directed to a modified release oral dosage form comprising about 650 mg of tranexamic acid or pharmaceutically acceptable salt thereof and a modified release material, the dosage form being suitable for oral administration on a three times a day basis, and the dosage form providing a mean maximum plasma concentration ($C_{max}$) of tranexamic acid of from about 5 to about 17.5 mcg/ml, preferably from about 6.5 to about 15 mcg/ml, more preferably from about 9 to about 14.5 mcg/ml per 1300 mg tranexamic acid after single dose oral administration to humans.

In certain embodiments, the invention is further directed to a modified release oral dosage form comprising about 650 mg of tranexamic acid or pharmaceutically acceptable salt thereof and a modified release material, the dosage form being suitable for oral administration on a twice a day basis, and the dosage form providing a mean maximum plasma concentration ($C_{max}$) of tranexamic acid of from about 5 to about 40 mcg/ml, preferably from about 10 to about 30 mcg/ml per 1950 mg tranexamic acid after single dose oral administration to humans.

In certain embodiments, the invention is further directed to a modified release oral dosage form comprising about 650 mg of tranexamic acid or pharmaceutically acceptable salt thereof and a modified release material, the dosage form being suitable for oral administration on a three times a day basis, and the dosage form providing a mean plasma concentration of tranexamic acid of from about 5 to about 25 mcg/ml, preferably from about 7.5 to about 15 mcg/ml, more preferably from about 8 to about 10 mcg/ml, most preferably about 9 mcg/ml per 1300 mg tranexamic acid after steady state oral administration to humans.

In certain embodiments, the invention is further directed to a modified release oral dosage form comprising about 650 mg of tranexamic acid or pharmaceutically acceptable salt thereof and a modified release material, the dosage form being suitable for administration on a three times a day basis, and the dosage form providing a mean maximum plasma concentration ($C_{max}$) of tranexamic acid of from about 5 to about 25 mcg/ml, preferably from about 10 to about 20 mcg/ml, more preferably from about 12.5 to about 17.5 mcg/ml, most preferably about 15 to about 17 mcg/ml per 1300 mg tranexamic acid after steady state oral administration to humans.

In certain embodiments, the invention is further directed to a modified release oral dosage form comprising about 650 mg of tranexamic acid or pharmaceutically acceptable salt thereof and an modified release material, the dosage form being suitable for administration on a three times a day basis, and the dosage form providing a mean plasma trough concentration of tranexamic acid or pharmaceutically acceptable salt thereof of from about 2 to about 10 mcg/ml, preferably from about 3 to about 7.5 mcg/ml, more preferably about 4 to about 7 mcg/ml, most preferably about 5 to about 6 mcg/ml per 1300 mg tranexamic acid or after steady state oral administration to humans.

In certain embodiments, the invention is further directed to a method of treating a patient with a therapeutically effective amount of tranexamic acid or pharmaceutically acceptable salt thereof comprising administering to the patient two dosage forms of the present invention, each dosage form comprising from about 585 mg to about 715 mg of tranexamic acid or pharmaceutically acceptable salt thereof, preferably about 650 mg tranexamic acid or pharmaceutically acceptable salt thereof, and a modified release material such that the dosage form is suitable for oral administration on a three times a day basis.

In certain embodiments, the invention is further directed to a method of treating a patient with a therapeutically effective amount of tranexamic acid or pharmaceutically acceptable salt thereof comprising administering to the patient three dosage forms of the present invention, each dosage form comprising from about 585 mg to about 715 mg, preferably about 650 mg tranexamic acid or pharmaceutically acceptable salt thereof, and a modified release material such that the dosage form is suitable for oral administration on a twice a day basis.

In certain embodiments, the invention is directed to a dose of tranexamic acid or pharmaceutically acceptable salt thereof comprising two unit dosage forms of a modified release formulation, each unit dosage form of said modified release formulation comprising from about 585 mg to about 715 mg, preferably about 650 mg of tranexamic acid or pharmaceutically acceptable salt thereof, and a modified release material which provides for the release of the tranexamic acid or pharmaceutically acceptable salt thereof from the dosage form such that the dose provides a therapeutic effect when administered three times a day.

In certain embodiments, the invention is directed to a dose of tranexamic acid comprising three unit dosage forms of a modified release formulation, each unit dosage form of said modified release formulation comprising from about 585 mg to about 715 mg, preferably about 650 mg of tranexamic acid or pharmaceutically acceptable salt thereof, and a modified release material which provides for the release of the tranexamic acid or pharmaceutically acceptable salt thereof from the dosage form such that the dose provides a therapeutic effect when administered twice a day.

In certain preferred embodiments, the invention is further directed to a modified release oral dosage form including tranexamic acid or pharmaceutically acceptable salt thereof and a modified release material which provides for the modified release of the tranexamic acid or pharmaceutically acceptable salt thereof from the dosage form such that the dosage form is suitable for administration on a two or three times a day basis and the dosage form provides a dissolution release rate in-vitro of the tranexamic acid or pharmaceutically acceptable salt thereof when measured by the USP 27 Apparatus Type II Paddle Method @ 50 RPM in 900 ml water at 37±0.5° C. of about 0% to about 40% by weight tranexamic acid or pharmaceutically acceptable salt thereof released at about 15 minutes, from about 20% to about 60% by weight tranexamic acid or pharmaceutically acceptable salt thereof released at about 30 minutes, from about 40% to about 80% by weight tranexamic acid or pharmaceutically acceptable salt thereof released at about 45 minutes, from about 50% to about 95% by weight tranexamic acid or pharmaceutically acceptable salt thereof release at about 60 minutes, and not less than about 60% by weight tranexamic acid or pharmaceutically acceptable salt thereof released at about 90 minutes.

In certain preferred embodiments, the invention is further directed to a modified release oral dosage form including tranexamic acid or pharmaceutically acceptable salt thereof and a modified release material which provides for the modified release of the tranexamic acid or pharmaceutically acceptable salt thereof from the dosage form such that the dosage form is suitable for administration on a two or three times a day basis and the dosage form provides a dissolution release rate in-vitro of the tranexamic acid or pharmaceutically acceptable salt thereof when measured by the USP 27 Apparatus Type II Paddle Method @ 50 RPM in 900 ml water at 37±0.5° C. of about 14% to about 22% by weight tranexamic acid or pharmaceutically acceptable salt thereof released at about 15 minutes, from about 32% to about 50% by weight tranexamic acid or pharmaceutically acceptable salt thereof released at about 30 minutes, from about 47% to about 71% by weight tranexamic acid or pharmaceutically acceptable salt thereof released at about 45 minutes, from about 61% to about 92% by weight tranexamic acid or pharmaceutically acceptable salt thereof release at about 60 minutes, and from about 79% to about 100% by weight tranexamic acid or pharmaceutically acceptable salt thereof released at about 90 minutes.

In certain embodiments, the invention is directed to a modified release oral dosage form comprising tranexamic acid or pharmaceutically acceptable salt thereof and an effective amount of a modified release excipient such that the dosage form releases from about 10% to about 25% by weight tranexamic acid or pharmaceutically acceptable salt thereof every 15 minutes when measured in vitro utilizing the USP 27 Apparatus Type II Paddle Method @ 50 RPM in 900 ml water at 37±0.5° C. In certain preferred embodiments, the dosage form releases about 18% to about 23% by weight tranexamic acid or pharmaceutically acceptable salt thereof every 15 minutes when measured in vitro utilizing the USP 27 Apparatus Type II Paddle Method @ 50 RPM in 900 ml water at 37±0.5° C. Most preferably, the dosage form releases about 100% of said tranexamic acid or pharmaceutically acceptable salt thereof within about 120 minutes when measured in vitro utilizing the USP 27 Apparatus Type II Paddle Method @ 50 RPM in 900 ml water at 37±0.5° C. In certain embodiments, the dosage form releases about 1% of said tranexamic acid or pharmaceutically acceptable salt thereof every minute when measured in vitro utilizing the USP 27 Apparatus Type II Paddle Method @ 50 RPM in 900 ml water at 37±0.5° C.

In certain preferred embodiments, the modified release oral dosage form of the invention further provides a mean transit time of said tranexamic acid of 7.70±0.72 hours when administered across a patient population.

In certain preferred embodiments, the modified release oral dosage form of the invention further provides a mean absorption time of said tranexamic acid of 4.18±0.70 hours when administered across a patient population.

In certain further embodiments, the modified release oral dosage form of the present invention provides confidence intervals derived from ln-transformed pharmacokinetic kinetic parameters $AUC_{0-t}$, $AUC_{inf}$ and $C_{max}$ for tranexamic acid in plasma which are within a 80-125% range of an immediate release formulation including an equivalent amount of tranexamic acid when administered across a patient population under fasted conditions.

In certain embodiments, the invention is further directed to a modified release oral dosage form comprising tranexamic acid or pharmaceutically acceptable salt thereof and a modified release material which provides for the modified release of the tranexamic acid or pharmaceutically acceptable salt thereof from the dosage form such that the dosage form is suitable for administration on a two or three times a day basis and the dosage form provides less than about 20 percent incidence of headache as a side effect after single dose oral administration across a patient population.

In certain embodiments, the invention is further directed to a modified release oral dosage form comprising tranexamic acid or pharmaceutically acceptable salt thereof and a modified release material which provides for the modified release of the tranexamic acid or pharmaceutically acceptable salt thereof from the dosage form such that the dosage form is suitable for administration on a two or three times a day basis and the dosage form provides less than about 10 percent incidence of nausea as a side effect when administered across a patient population, less than about 7 percent incidence of nausea when administered across a patient population, preferable less than about 5 percent incidence of nausea as a side effect when administered across a patient population, more preferably less than about 2 percent incidence of nausea as a side effect after single dose oral administration across a patient population.

In certain embodiments, the modified release oral dosage form of the present invention provides less CNS side effects (e.g., headache), less GI side effects (e.g., nausea), or combination thereof in comparison to an equivalent amount of tranexamic acid or pharmaceutically acceptable salt thereof in an immediate release formulation when administered across a patient population. Additionally or alternatively, in certain embodiments the dosage form provides less CNS side effects (e.g., headache), less GI side effects (e.g., nausea), or combination thereof in comparison to a therapeutically equivalent amount of tranexamic acid administered intravenously in five minutes or less across a patient population.

In certain embodiments, the modified release oral dosage form of the present invention provides for the reduction of at least one side effect as compared to an immediate release oral dosage form including an equivalent amount of tranexamic acid or pharmaceutically acceptable salt thereof, when the immediate release dosage form is administered across a same or different population of patients as said modified release dosage form, and wherein said immediate release dosage form releases all of said tranexamic acid or pharmaceutically acceptable salt thereof within about 45 minutes when measured in vitro utilizing the USP 27 Apparatus Type II Paddle Method @ 50 RPM in 900 ml water at 37±0.5° C. Such side effects can be for example, headache, nausea, vomiting, diarrhea, constipation, cramping, bloating, and combinations thereof.

In certain embodiments, the modified release oral dosage form of the present invention provides a mean transit time of tranexamic acid which is at least about 20 minutes longer, preferably about 30 minutes longer, than an immediate release formulation including an equivalent amount of tranexamic acid when administered across a patient population.

In certain embodiments, the dosage form of the present invention provides a mean absorption time of tranexamic acid which is at least about 20 minutes longer, preferably about 30 minutes longer, than an immediate release formulation including an equivalent amount of tranexamic acid when administered across a patient population.

In certain preferred embodiments, the therapeutically effective dose of the tranexamic acid or pharmaceutically acceptable salt thereof is provided via the administration of two or more dosage units. For example, if the dosage unit comprises 650 mg of tranexamic acid or pharmaceutically acceptable salt thereof and the dose for administration is about 1300 mg then two dosage units would be administered to a patient in need of such treatment, or for example, when the dose for administration is 1950 mg, three dosage units would be administered.

In certain preferred embodiments, the invention is further directed to a method of treating a patient with one or more modified release oral dosage forms comprising tranexamic acid or pharmaceutically acceptable salt thereof and a modified release material, wherein the oral dosage form provides a therapeutically effective plasma level of tranexamic acid or pharmaceutically acceptable salt thereof in accordance with a three times a day (TID) dosing schedule, and the therapeutically effective dose administered comprises about 1300 mg of tranexamic acid or pharmaceutically acceptable salt thereof.

In certain preferred embodiments, the invention is further directed to a method of treating a patient with one or more modified release oral dosage forms comprising tranexamic acid or pharmaceutically acceptable salt thereof and a modified release material, wherein the oral dosage form provides a therapeutically effective plasma level of tranexamic acid or pharmaceutically acceptable salt thereof in accordance with a twice a day (BID) dosing schedule, and the therapeutically effective dose administered comprises about 1950 mg of tranexamic acid or pharmaceutically acceptable salt thereof.

In certain embodiments, the invention is directed to a method of providing a tranexamic acid plasma concentration within the range of about 5 mcg/mL to about 15 mcg/mL by administration of a modified release formulation of the present invention comprising tranexamic acid or pharmaceutically acceptable salt thereof and a modified release material on a three times a day basis to a patient in need of tranexamic acid or pharmaceutically acceptable salt thereof treatment.

In certain embodiments, the invention is further directed to a method of treating a human patient with heavy menstrual bleeding (e.g., menorrhagia) comprising administering about 1300 mg of tranexamic acid or pharmaceutically acceptable salt thereof on a three times a day basis to the human patient to provide a tranexamic acid or pharmaceutically acceptable salt thereof plasma concentration within the range of about 5 mcg/mL to about 15 mcg/mL after steady state oral administration to a human patient.

In certain embodiments, the invention is directed to a method of treating a patient suffering from menorrhagia, including patients with heavy menstrual bleeding due to fibroids, conization of the cervix, epistaxis, hyphema, hereditary angioneurotic edema, a patient with a blood coagulation disorder undergoing dental surgery, combinations thereof, and the like, by administering at least one dosage form of the present invention to the patient in need in tranexamic acid or pharmaceutically acceptable salt thereof therapy.

In certain embodiments, the invention is directed to a method of treating heavy menstrual bleeding with a therapeutically effective dose of at least one oral formulation of the present invention comprising tranexamic acid or pharmaceutically acceptable salt thereof and a modified release material wherein the menstrual blood loss per menstrual cycle is reduced by at least about 10 ml, preferably at least about 20 ml, more preferably at least about 40 ml. In a most preferred embodiment the menstrual blood loss per menstrual cycle is reduced by greater than or equal to about 50 ml.

In certain embodiments, the invention is directed to a method of treating heavy menstrual bleeding with a therapeutically effective dose of at least one oral formulation of the present invention comprising tranexamic acid or pharmaceutically acceptable salt thereof and a modified release material which upon oral administration to a human female reduces the blood loss per menstrual cycle by about 35 ml to about 200 ml, preferably about 40 ml to about 175 ml, more preferably from about 50 ml to about 150 ml.

In certain embodiments, the invention is further directed to a method of treating heavy menstrual bleeding with a therapeutically effective dose of at least one oral formulation of the present invention comprising tranexamic acid or pharmaceutically acceptable salt thereof and a modified release material which upon oral administration to a human female reduces the blood loss per menstrual cycle by about 20% to 100%, preferably from about 20% to about 70%.

In certain other embodiments, the present invention is directed to the use of the tranexamic acid formulations described herein for the treatment of heavy menstrual bleeding (menorrhagia) and the amelioration of symptoms associated with heavy menstrual bleeding, including limitations on social, leisure, and physical activities.

The menstrual blood loss can be measured by procedures known in the art. For example, in certain embodiments, the menstrual blood loss can be determined by a procedure described by (i) L. Hallbert, et al. in "Determination of Menstrual Blood Loss", *Scandinav. J. Clin. & Lab. Investigation*, 244-248, 16, 1964, wherein the procedure is performed by extracting the menstrual blood from vaginal tampons and towels with a sodium hydroxide solution, converting heme chromogens to alkaline hematin, which is determined spectrophotometrically; or (ii) the menstrual blood loss can be determined by a procedure described by J. Newton, M. D., et al., in "A Rapid Method for Measuring Menstrual Blood Loss Using Automatic Extraction.", *Contraception*, 269-282, September 1977, Vol. 16, No. 3, wherein the procedure is based upon the formation of alkaline haematin after the blood has been extracted from vaginal tampons and sanitary towels by an automatic Stomacher Lab-Blender. The disclosures of the aforementioned articles are hereby incorporated by reference in their entireties.

In certain embodiments, the modified release material may be incorporated in a coating applied onto e.g., a tablet comprising the tranexamic acid or pharmaceutically acceptable salt thereof, or may be incorporated into a matrix with the tranexamic acid or pharmaceutically acceptable salt thereof, or a combination thereof. For example, in certain preferred embodiments, the modified release material is a controlled release material such as a gel-forming or hydratable polymer which is added to e.g., a matrix composition comprising the tranexamic acid or pharmaceutically acceptable salt thereof.

In certain embodiments, the tranexamic acid for use in the methods and formulations of the present invention is in the form of a pharmaceutically acceptable salt thereof. Such salt forms include for example and without limitation the sodium salt, potassium salt, calcium salt, magnesium salt and the like; as well as the hydrochloride, hydrobromide, sulfate, phosphate, formate, acetate, trifluoroacetate, maleate, tartrate, methanesulfonate, benzenesulfonate, p-toluenesulfonate-methanesulfonate salt forms, and the like. Preferably the active ingredient for use in accordance with the present invention is tranexamic acid.

An "immediate release oral dosage form" for purposes of the present invention is a dosage form which releases all of active ingredient (e.g., tranexamic acid) included therein within about 45 minutes when measured in vitro utilizing the USP 27 Apparatus Type II Paddle Method @ 50 RPM in 900 ml water at 37±0.5° C.

A "modified release oral dosage form" for purposes of the present invention is an oral dosage form which releases the active ingredient (e.g., tranexamic acid) included therein in a manner that is slower than an immediate release oral dosage form and faster than a controlled release oral dosage form, when the dosage forms include the same amount of active as the modified release oral dosage form. One definition of the terms "slower" and "faster" as used in this application is that they are meant to represent a statistically significant difference at each measured 15 minute interval after the start of in-vitro dissolution. In certain preferred embodiments, the modified release oral dosage form of the present invention provides an in-vitro dissolution release rate of tranexamic acid or pharmaceutically acceptable salt thereof, when measured by a USP 27 Apparatus Type II Paddle Method @ 50 RPM in 900 ml water at 37±0.5° C., of less than about 70% by weight tranexamic acid or pharmaceutically acceptable salt thereof released at about 45 minutes and about 100% by weight of said tranexamic acid or pharmaceutically acceptable salt thereof released by about 120 minutes.

A "controlled release oral dosage form" for purposes of the present invention is a dosage form which releases all of the active ingredient (e.g., tranexamic acid) included therein after about 4 hours or more when measured in vitro utilizing the USP 27 Apparatus Type II Paddle Method @ 50 RPM in 900 ml water at 37±0.5° C.

The term "$C_{max}$" unless otherwise indicated is meant for purposes of the present invention to mean the maximum plasma concentration of a medicament achieved after single dose administration of a dosage form, or the maximum plasma concentration of a medicament achieved over a dosing interval from multiple-doses at steady-state in accordance with the present invention.

The term "$T_{max}$" is meant for purposes of the present invention to mean the elapsed time from administration of a dosage form to the time the $C_{max}$ of the medicament is achieved.

The term "steady state" means that the amount of the drug reaching the system is approximately the same as the amount of the drug leaving the system. Thus, at "steady-state", the patient's body eliminates the drug at approximately the same rate that the drug becomes available to the patient's system through absorption into the blood stream.

The term "mean" for purposes of the present invention, when used to define a pharmacokinetic value (e.g., $T_{max}$), unless specified otherwise, represents the arithmetic mean value measured across a patient or subject population.

The term "three times a day (TID) basis" for purposes of the present invention, means that the dosage regimen is to be administered three times a day, preferably on a schedule of every 8 hours.

The term "mean transit time" is understood by those skilled in the art and means the time-point where 63.2% of the total AUC is attained after oral administration, or 63.2% of the IV dose is eliminated, as described in *Applied Pharmacokinetics, Principles of Therapeutic Drug Monitoring*, Second Edition (1986), edited by William E. Evans, et al., the disclosure of which is hereby incorporated by reference in its entirety.

The term "mean absorption time" is understood by those skilled in the art and means a quantitative parameter which summarizes how long, on average, the drug molecule remains unabsorbed, i.e. persists in its dosage form and in the gastrointestinal tract, also as described in *Applied Pharmacokinetics, Principles of Therapeutic Drug Monitoring*, Second Edition (1986), edited by William E. Evans, et al. Unlike the absorption rate constants (ka) which can be skewed, the mean absorption time is not affected by incomplete release of drug from its dosage form, irregular absorption, lag-time, mixed zero-order dissolution rates, changing GI motility, GI blood flow, first-pass effect, etc.

"Therapy" for excessive menstrual bleeding is defined for the purpose of this invention as one or more courses of treatment with an antifibrinolytic agent such as, but not limited to, tranexamic acid, aminocaproic acid, and any pharmaceutically acceptable salts, esters, derivatives, pro-drugs, metabolites, and analogues of any of the foregoing antifibrinolytic agents.

The term "heavy menstrual bleeding" is defined for purposes of the present invention as a perceived blood loss of at least heavy to very heavy which may correspond to a periodic blood loss of at least about 30 ml per cycle to as much as 1000 ml per cycle as measured by the alkaline hematin test. The periodic blood loss perceived or as measured with the alkaline hematin test may vary depending on the severity of the condition and the physiological make up of the individual patient. Therefore, heavy menstrual bleeding may include periodic blood losses of at least about 30 ml per cycle. Losses from between about 30 ml, about 40 ml, about 50 ml, about 60 ml, about 70 ml, about 80 ml, about 90 ml to about 300 ml are contemplated as are losses greater than 300 ml, such as for example, losses between about 300 ml to about 1000 ml.

BRIEF DESCRIPTION OF THE FIGURES

FIG. 7 is a listing of the Menorrhagia Impact Measures of the present invention.

DETAILED DESCRIPTION

Figure 1:
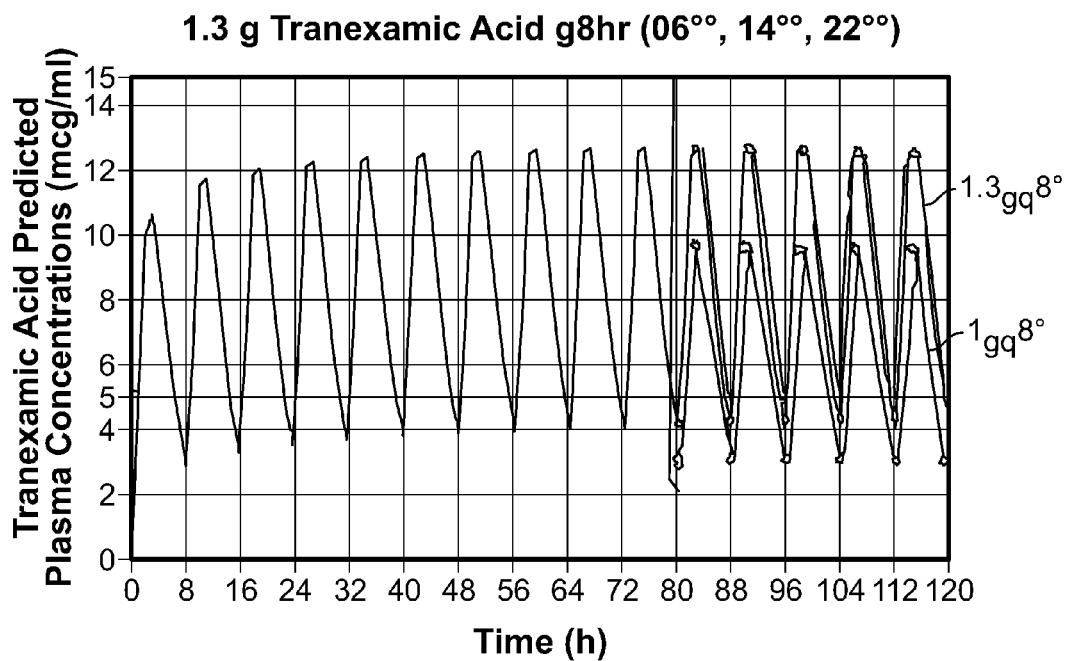
FIG. 1 depicts concentration-time profiles for simulated administration of the 1.3 g tranexamic acid modified release formulation of Example 1 at a Q8H (every 8 hours) dosing schedule of 6:00 AM, 2:00 PM, 10:00 PM comparing it with 1 g administered Q8H.

The tranexamic acid (API) utilized in the formulations of the present invention is available from various manufacturers. The tranexamic acid particles utilized in the present invention may range from about 0.1 to about 550 microns. For example, the tranexamic acid particles may have a particle size range from <about 0.5 to about 520 microns.

The tranexamic acid particles utilized in the present invention may have a $D_{25}$ particle size distribution ranging from about 5 to about 15 microns, a $D_{50}$ particle size distribution ranging from about 14 to about 73 microns, and a $D_{75}$ particle size distribution ranging from about 30 to about 205 microns.

The particle size of the tranexamic acid utilized may also have a particle size range wherein about 1% of the particles are of a size greater than about 250 microns, about 8% of the particles are of a size of about 180 microns, about 9% of the particles are of a size of about 150 microns, about 4% of the particles are of a size of about 125 microns, about 20% of the particles are of a size of about 75 microns, about 14% of the particles are of a particle size of about 45 microns, and about 44% of the particles are of a particle size less than about 45 microns.

The tranexamic acid utilized may also have a particle size range wherein about 5% of the particles are of a size greater than about 250 microns, about 12% of the particles are of a size of about 180 microns, about 14% of the particles are of a size of about 150 microns, about 14% of the particles are of a size of about 125 microns, about 29% of the particles are of a size of about 75 microns, about 12% of the particles are of a particle size of about 45 microns, and about 14% of the particles are of a particle size less than about 45 microns.

The tranexamic acid utilized may also have a particle size range wherein about 2% of the particles are of a size greater than about 250 microns, about 7% of the particles are of a size of about 180 microns, about 9% of the particles are of a size of about 150 microns, about 4% of the particles are of a size of about 125 microns, about 20.5% of the particles are of a size of about 75 microns, about 16% of the particles are of a particle size of about 45 microns, and about 41.5% of the particles are of a particle size less than about 45 microns.

The tranexamic acid utilized may also have a particle size range wherein about 0% of the particles are of a size greater than about 250 microns, about 5% of the particles are of a size of about 180 microns, about 12% of the particles are of a size of about 150 microns, about 11% of the particles are of a size of about 125 microns, about 31% of the particles are of a size of about 75 microns, about 17% of the particles are of a particle size of about 45 microns, and about 24% of the particles are of a particle size less than about 45 microns.

The tranexamic acid utilized may also have a particle size range wherein about 20% of the particles are of a size of about 125 microns, about 20% of the particles are of a size of about 75 microns, about 20% of the particles are of a particle size of about 45 microns, and about 45% of the particles are of a particle size less than about 45 microns.

The dosage regimen typically listed for tranexamic acid in HMB (Heavy Menstrual Bleeding) therapy is 1-1.5 g per dose administered three-four times a day at the onset of copious menstrual bleeding and continued for the first 3-5 days of the menstrual cycle. However, the most frequently reported dosage regimen of tranexamic acid is an immediate release oral formulation in which 1 g tranexamic acid is administered four times a day (4 g per day) for HMB therapy outside of the US. Knowledge of this common regimen is supported by a careful review of the randomized controlled trials published in the medical literature, product labeling from other countries' regulatory authorities having the product approved for HMB therapy, utilization data from Sweden (Rybo 1991), correspondence and interviews with non-US clinicians having experience with the product. That regimen is currently the dosage being studied by the US Center for Disease Control (CDC) in women with HMB associated with bleeding disorders.

The absolute bioavailability of tranexamic acid observed when administering the European commercial formulation (Cyklokapron, Kabi AB, Sweden Batch 90288; assay 499 mgm/tablet) to male subjects is approximately 35% and its elimination correlates with renal creatinine clearance. Peak serum tranexamic acid concentrations occur approximately 3 hours after the oral administration of a European immediate-release tablet formulation (>85% dissolved at 15 minutes) (Pilbrant, et al., *Eur. J. Clin. Pharmacol*, (1981)-20:65-72). By comparison, the in vivo absorption profile observed with the European immediate-release formulation is slow and very gradual over 3 hours. Specifically, tranexamic acid serum concentrations are 9, 41, 73, 88 percent (with food), and 22, 63, 85, and 98 percent (fasting) of maximal absorption at 0.5, 1, 1.5 and 2 hours after a 2 g oral dose, respectively. Although not wishing to be held to any specific theory, it is presently hypothesized that tranexamic acid oral absorption appears to be controlled by a non-dissolution rate limited process, i.e. the rate and extent of oral absorption is a function of a trans-membrane passage-limited process, in order to explain the disparity between the time of product dissolution and relatively prolonged tmax (time to achieve the peak serum concentration).

Preferably, the goal of the formulation, dose strength and dosage regimen of the invention, is to provide HMB therapy which achieves from about 20% to 100% reduction in menstrual blood loss per menstrual cycle. In accordance with certain embodiments of the present invention, the preferred tranexamic acid dose of 1.3 g every 8 hours is predicted to provide an average serum tranexamic acid concentration comparable to that produced by a 1 g every 6 hour regimen (i.e. 12.4 mcg/mL), with associated peaks and troughs falling approximately within the therapeutic antifibrinolytic range (5-15 mcg/mL; Cyklokapron NDA 19-280). In certain embodiments, a two-compartment oral absorption and elimination simulation model coupled with pharmacokinetic data (Pilbrant, et al., *Eur. J. Clin. Pharmacol*, (1981)-20:65-72), and modified-release tablet dissolution performance information were used to determine the preferred lead dosage regimen.

In immediate release formulations the entire dose and the soluble components in the dosage form dissolve in gastrointestinal fluid and present a high concentration of solutes for absorption. The most frequently reported adverse effects are primarily confined to the proximal gastrointestinal tract (nausea and vomiting). These adverse symptoms appear to be related to the drug load presented to the gastric mucosa, since this effect can be minimized by reducing the immediate-release oral formulation dose or administering the product slowly by the intravenous route. In certain embodiments, a lower incidence of proximal gastrointestinal adverse effects is obtained with the preferred oral modified release formulation (e.g., dosed 1.3 g every 8 hours) of the invention, e.g., because of the modified release properties of the drug product formulation.

In certain embodiments, the oral dosage form of the present invention provides for an increased bioavailability as compared to immediate release oral dosage forms currently available (e.g., Cyclokapron). In certain preferred embodiments the increased bioavailability allows therapeutic plasma levels of tranexamic acid to be reached with a lower dose of drug. Preferably, the increased bioavailability also decreases the amount of tranexamic acid that remains unabsorbed in the gastrointestinal which leads to decreased incidence of side effects that are typically associated with formulations that provide higher levels of unabsorbed tranexamic acid and prolonged exposure of the gastrointestinal tract to the higher tranexamic acid levels. Preferably the oral dosage form of the present invention provides for a bioavailability of tranexamic acid of greater than 40%, from about 41% to about 60%, preferably from about 42% to about 50%, more preferably about 45% after oral administration to humans.

The modified release oral formulations of tranexamic acid of the present invention provides a release of the drug which is slower than that of the immediate release 500 mg Cyklokapron product current marketed in Canada which provided a mean release rate of 100% by weight tranexamic acid released by about 15 minutes when measured utilizing USP 27 Apparatus Type II paddle method @ 50 RPM in 900 ml water at 37±0.5° C.

In certain embodiments, the modified release oral formulations may be described as providing a mean transit time through the proximal gastrointestinal mucosa which takes approximately one half hour longer than an immediate release formulation. In other preferred embodiments, the modified release formulations of the invention provide a rate of release of (dissolved) tranexamic acid from the dosage form in-vitro which is approximately 20, 40, 60, 80, and 100 percent of the total dose at 0.25, 0.5, 0.75, 1 and 1.5 hours, respectively. In certain preferred embodiments, such a release rate in-vitro demonstrates that the formulations of the present invention provide a relative reduction in the amount and rate of dissolved tranexamic acid presented to the proximal gastric mucosa to approximate 20, 40, 60, 80, and 100 percent of the total dose at 0.25, 0.5, 0.75, 1 and 1.5 hours, respectively, after oral administration.

In certain embodiments, the majority of tranexamic acid absorption appears to occur slowly distal to the stomach, and assuming linear pharmacokinetics, the modified release formulation produces an absorption profile which is comparable to that achieved with the currently available oral immediate release formulations used outside the U.S.

In accordance with the present invention a modified release tranexamic acid tablet for oral administration is disclosed. Preferably, the tablet contains at least one material (defined herein as any substance other than the active, i.e., tranexamic acid) which minimizes or eliminates the adverse gastrointestinal side effects in patients, for example, women dosed with oral tranexamic acid for treatment of menorrhagia.

The modified release oral dosage forms of tranexamic acid for purposes of the present invention include formulation ingredients and/or configurations which are typically utilized for formulations known in the art as extended, sustained and controlled release formulations, although modified to provide a desirable release rate in keeping with the teachings of the present invention. The modified release formulations preferably decrease the concentration of tranexamic acid and materials dissolved in the stomach fluids after dosing by controllably releasing tranexamic acid over a period of time, as opposed to immediate release formulations which release the entire dose of tranexamic acid all at once. The modified release formulations of the present invention thus minimize or prevent gastrointestinal reactions and side effects that occur when a dose of tranexamic acid is ingested and immediately reaches the stomach.

The modified release dosage forms of the present invention may be prepared as; tablets, capsules, granules, pellets, powders, dragees, troches, non-pariels, pills or encapsulated suspension, and may be packaged into capsules, sachets, etc. Such dosage forms may be prepared by any formulation technique where release of the active substance (tranexamic acid) from the dosage form is modified to occur at a slower rate than from an immediate release product. In these formulations, tranexamic acid release occurs in the stomach and/or intestine, but at a slower rate so that a bolus of dissolved drug does not reach the lining of the stomach and cause adverse effects, or adverse effects occur with a lower intensity or frequency because of the lower concentration of tranexamic acid. Hence, adverse effects are preferably reduced, minimized or eliminated.

Methods of preparing modified release formulations are found in Modified Release Drug Delivery Technology, Rathbone, Hadgraft, and Roberts, Eds., Drugs and the Pharmaceutical Sciences, Vol. 126, Marcel Dekker Inc., New York, 2003; Modern Pharmaceutics, Third Edition, Banker and Rhodes, Eds. Drugs and the Pharmaceutical Sciences, Vol. 72, Marcel Dekker Inc., New York, 1996; Sustained and Controlled Release Drug Delivery Systems, Robinson, Ed., Drugs and the Pharmaceutical Sciences, Vol. 6, Marcel Dekker Inc., NY 1978; Sustained Release Medications, Chemical Technology Review No. 177, Johnson, Ed., Noyes Data Corporation 1980; Controlled Drug Delivery, Fundamentals and Applications, Second Edition, Robinson and Lee, Eds., Marcel Dekker Inc., New York, 1987, and as described in U.S. Pat. No. 6,548,084, each of these references being expressly incorporated by reference herein in its entirety.

Preferably, a modified release form, makes tranexamic acid available over an extended period of time after ingestion. Modified release dosage forms coupled with the digestion process and the absorption process in the gastrointestinal tract cause a reduction in the amount of tranexamic acid in solution in the gastrointestinal tract compared to dosing tranexamic acid presented as a conventional dosage form (e.g., as a solution, or as an immediate release dosage form). The modified release formulation may be verified by in vitro dissolution testing and in vivo bioequivalence documentation, according to Food and Drug Administration standards, e.g., as set forth at www.fda.gov, 21 CFR §314, 320, and also at USP 23 NF 18 §711, 724. For example, an in vitro dissolution test such as USP 27 Apparatus Type II Paddle Method @ 50 RPM in 900 ml water at 37±0.5° C. may be used to verify the release of the tranexamic acid from the dosage form.

Tranexamic acid modified release tablets may be formulated to provide a dose of tranexamic acid, typically about 500 mg to about 2 grams from one to two tablets, within about the first one to two hours after the tablet is ingested. Thus, tranexamic acid release occurs at a designed rate over a period e.g., about 60 minutes to about 120 minutes. The rate of tranexamic acid release over this period of time is designed to provide a reduced concentration of tranexamic acid in the stomach while allowing the absorption of tranexamic acid to occur throughout the gastrointestinal tract. Absorption of tranexamic acid typically begins as soon as tranexamic acid is released from the dosage form and is dissolved in the gastrointestinal fluids contacting the membranes which line the gastrointestinal tract. The rate of release of tranexamic acid from the dosage form and the absorption of drug by the gastrointestinal mucosa help to maintain low concentrations of drug in the gastrointestinal fluids. The lowered concentrations preferably result in lower intensity, frequency, and/or severity of gastrointestinal adverse side effects. The designed rate of release of tranexamic acid from the dosage form in the stomach and the upper small intestine, the natural emptying of gastric juice containing any dissolved tranexamic acid from the stomach, and the absorption of tranexamic acid from a larger segment of the gastrointestinal tract (i.e., both the stomach and the small intestine, rather than the stomach only or the lower portion of the small intestine if any modified release dosage form with a longer release time was used), preferably results in reduced levels of dissolved tranexamic acid in the region of the gastrointestinal tract proximal or distal to the dosage form. Reduced concentrations of tranexamic acid along the gastrointestinal tract preferably provide a reduction in adverse gastrointestinal effects associated with oral tranexamic acid therapy.

As used herein, alleviation of adverse effects using these formulations indicates any relief in one or more symptoms, such as decrease in incidence, severity, or duration of symptoms, and is not limited to absence of symptoms or elimination of symptoms. Thus, treatment includes any decrease in incidence, duration, intensity, frequency, etc. of adverse gastrointestinal symptoms including, but not limited to, headache, nausea, vomiting, diarrhea, constipation, cramping, bloating, and combinations thereof. The formulations may reduce symptoms at any time during tranexamic acid therapy, but minimized adverse effects are particularly noted immediately or shortly after dosing, that is, within the first few hours after dosing. As used herein, adverse gastrointestinal effects and side effects are used interchangeably to indicate nontherapeutic effects (i.e., not relating to any possible beneficial effects due to tranexamic acid), ranging from unpleasant but tolerable sensations to severe gastrointestinal symptoms. As used herein, the terms oral formulations, ingestable formulations, and orally administered formulations are used interchangeably and include any dosage forms which are ingested by mouth, including, but not limited to, tablets, pills, liquids, gelcaps, softgels, dragees, capsules, powders, granules, pellets, etc.

Modified release formulations of tranexamic acid include tablets, pellets, granules, capsules, or other oral dosage forms prepared in such a way to release tranexamic acid in a designed manner. In certain embodiments, the modified release material is a gel-forming polymer, a hydratable polymer, a water soluble polymer, a water swellable polymer, or mixtures thereof.

In certain embodiments, modified release tranexamic acid tablets are prepared by adding a modified release material comprising a gel-forming or hydratable polymer to a tranexamic tablet composition. Suitable gel-forming or hydratable polymers include, but are not limited to, hydroxyproplycellulose, hydroxypropylmethylcellulose or hypromellose, carboxymethylcellulose, polyvinyl alcohol, etc. This provides a compressed tablet that may or may not be film coated. The tablet releases tranexamic acid by diffusion of tranexamic acid through the tablet matrix, or by erosion of the tablet matrix, or by a combination of diffusion from and erosion of the tablet matrix. Tablets formed with water swellable polymers release tranexamic acid by diffusion of tranexamic acid through the tablet matrix, or by erosion of the tablet matrix, or by a combination of diffusion from and erosion of the tablet matrix. One or more water-soluble hydrophilic polymer(s) may also be used. These include polyvinyl pyrrolidine, hydroxypropyl cellulose, hydroxypropylmethylcellulose, now referred to as hypromellose (e.g., Methocel™, Dow Chemical Company), methyl cellulose, vinyl acetate/crotonic acid copolymers, methacrylic acid copolymers, maleic anhydride/methyl vinyl ether copolymers, derivatives thereof and mixtures thereof. In various embodiments, the polymer is hydroxypropyl cellulose or hydroxypropylmethylcellulose. The polymer may be hydroxypropyl-methyl cellulose with a viscosity ranging from about 50 cps to about 200 cps. The polymer may be hydroxypropyl-methyl cellulose with a viscosity of 100 cps, commercially available as Methocel™ K 100 LV (Dow Chemical Company). The amount of polymer in the composition may be in the range of about 5% by weight to about 50% by weight of the composition. In various embodiments, the polymer is in the range of about 10% by weight to about 35% by weight of the composition, or about 10% by weight to about 30% by weight of the composition.

In certain embodiments the modified release material comprises a vinyl polymer, phthalic acid derivative of vinyl copolymer, hydroxyalkylcellulose, alkylcellulose (e.g., ethylcellulose), cellulose acetate, hydroxyalkylcellulose acetate, cellulose ether, alkylcellulose acetate and partial esters thereof, and polymers and copolymers of lower alkyl acrylic acids and lower alkyl acrylates and partial esters thereof, or combination thereof. In preferred embodiments the modified release material comprises hydroxypropylcellulose, hydryoxpropylmethylcellulose, carboxymethylcellulose, polyvinyl alcohol, polyvinylpyrrolidone, methylcellulose, vinyl acetate/crotonic acid copolymers, methacrylic acid copolymers, maleic anhydride/methyl vinyl ether copolymers, derivatives thereof, and mixtures thereof. In further preferred embodiments the modified release material comprises a polymer such as a methacrylic acid copolymer. These are copolymers of methacrylic acid with neutral acrylate or methacrylate esters such as ethyl acrylate or methyl methacrylate.

In certain embodiments the modified release material comprises a pH independent binder or film-forming agent such as hydroxypropyl methycellulose, hydroxypropyl cellulose, methylcellulose, polyvinylpyrrolidone, neutral poly(meth) acrylate esters (e.g., the methyl methacrylate/ethyl acrylate copolymers sold as Eudragit® (Rohm Pharma), starches, gelatin, sugars such as glucose, sucrose, and mannitol, silicic acid, carboxymethylcellulose, and the like, diluents such as lactose, mannitol, dry starch, microcrystalline cellulose and the like, surface active agents such as polyoxyethylene sorbitan esters, sorbitan ethers, and the like, coloring agents, flavoring agents, lubricants such as talc, calcium stearate, and magnesium stearate, solid polyethylene glycols, sodium lauryl sulfate, and other tableting aids. Any combination of the aforementioned binders or film-forming agents may be included in the modified release material. The modified release material may be combined with tranexamic acid to form modified release dosage forms.

In certain embodiments, the formulation includes tranexamic acid in the range of about 50% by weight to about 95% or more by weight of the formulation. In other embodiments, tranexamic acid is in the range of about 60% by weight to about 90% by weight, or about 60% by weight to about 80% by weight of the formulation. The remaining weight may be made up of the modified release material and additional excipients.

To prepare modified release tablet formulations, the agent or modified release material to slow the release of tranexamic acid may be incorporated into the tablet matrix or coated onto the tablet surface or both. In certain embodiments, tablet formulations prepared are formulated by granulating a blend of powders of the modified release material. The powder blend is formed by combining portions of the powdered components that make up the tablet. These powders are intimately mixed by dry-blending. The dry blended mixture is granulated by wet mixing of a solution of a binding agent with the powder blend. The time for such wet mixing may be controlled to influence the dissolution rate of the formulation. For example, the total powder mix time, that is, the time during which the powder is granulated, may range from about 1 min to about 10 min, or from about 2 min to about 5 min. Following granulation, the particles are removed from the granulator and placed in a fluid bed dryer, a vacuum dryer, a microwave dryer, or a tray dryer for drying. Drying conditions are sufficient to remove unwanted granulating solvent, typically water, or to reduce the amount of granulating solvent to an acceptable level. Drying conditions in a fluid bed dryer or tray dryer are typically about 50 to 70° C. The granulate is dried, screened, mixed with additional excipients such as disintegrating agents, flow agents, or compression aids and lubricants such as talc, stearic acid, or magnesium stearate, and compressed into tablets.

In certain embodiments, the tablet that contains a modified release material within the tablet matrix may be coated with an optional film-forming agent. This applied film may aid in identification, mask an unpleasant taste, allow desired colors and surface appearance, provide enhanced elegance, aid in swallowing, aid in enteric coating, etc. The amount of film-forming agent may be in the range of about 2% tablet weight to about 4% tablet weight. Suitable film-forming agents are known to one skilled in the art and include hydroxypropyl cellulose, cellulose ester, cellulose ether, one or more acrylic polymer(s), hydroxypropyl methylcellulose, cationic methacrylate copolymers (diethylaminoethyl)methacrylate/methyl-butyl-methacrylate copolymers such as Eudragit E® (Rohm Pharma) and the like. The film-forming agents may optionally contain colorants, plasticizers, fillers, etc. including, but not limited to, propylene glycol, sorbitan monooleate, sorbic acid, titanium dioxide, and one or more pharmaceutically acceptable dye(s).

In certain embodiments, the tranexamic acid tablets of the invention are coated with a modified release material. In certain embodiments, tranexamic acid tablets are formulated by dry blending, rotary compacting, or wet granulating powders composed of tranexamic acid and tablet excipients. These powders are compressed into an immediate release tablet. Coating this immediate release tablet with a modified release material as described herein renders this tranexamic acid tablet as a modified release tablet.

In addition to the modified release material, the formulations of the invention may also contain suitable quantities of other materials, e.g. preservatives, diluents (e.g., microcrystalline cellulose), lubricants (e.g., stearic acid, magnesium stearate, and the like), binders (e.g., povidone, starch, and the like), disintegrants (e.g, croscarmellose sodium, corn starch, and the like), glidants (e.g., talc, colloidal silicon dioxide, and the like), granulating aids, colorants, and flavorants that are conventional in the pharmaceutical art. Specific examples of pharmaceutically acceptable excipients that may be used to formulate oral dosage forms are described in the Handbook of Pharmaceutical Excipients, American Pharmaceutical Association (2003), incorporated by reference herein.

The release process may be adjusted by varying the type, amount, and the ratio of the ingredients to produce the desired dissolution profile, as known to one skilled in the art. A coating may be a partially neutralized pH-dependent binder that controls the rate of tranexamic acid dissolution in aqueous media across the range of pH in the stomach, which has a pH of about 2, and the intestine, which has a pH of about 5.5 in its upper region. In certain embodiments, one or more pH dependent binders may be used to modify the dissolution profile so that tranexamic acid is released slowly and continuously as the formulation passes through the stomach and/or intestines.

In one embodiment, compressed modified release tablets are formulated to comply with USP criteria and to be of such a size and shape to be easy to swallow. The size of the tablet will depend upon the dose of tranexamic acid that is needed to provide adequate therapy and the particular formulation and excipients that are selected to provide the physical properties necessary for tableting and for modified release. In various embodiments, a compressed modified release tablet contains from about 500 mg to about 1 gram of tranexamic acid, or from about 600 mg to about 750 mg of tranexamic acid. The daily dose of tranexamic acid may be achieved by taking one or two tablets at each dosing time.

In certain embodiments, the tranexamic acid included in the dosage form is from about 375 mg to about 1500 mg, preferably from about 375 mg to about 1000 mg. In one embodiment, the dose of tranexamic acid per tablet is in the range of about 500 mg to about 1000 mg for tablets and from about 500 mg to about 1500 mg for a sachet filled with granules. In another embodiment, the dose of tranexamic acid is in the range of about 3 grams/day to about 6 grams/day in three or four divided doses. As an example, a total daily dose of 3 grams tranexamic acid may be divided into three doses of one tablet each with each tablet containing 1 gram tranexamic acid, or may be divided into four doses of one tablet each with each tablet containing 0.75 gram tranexamic acid. As another example, a total daily dose of 4 gram tranexamic acid may be divided into three doses of two tablets at each dose with each tablet containing 0.666 gram tranexamic acid, or may be divided into four doses of one tablet each with each tablet containing 1 gram tranexamic acid. As another example, a total daily dose of 5 gram tranexamic acid may be divided into three doses of one tablet each with each tablet containing 1.66 gram tranexamic acid, or may be divided into four doses of two tablets each with each tablet containing 0.625 gram tranexamic acid. As another example, a total daily dose of 6 gram tranexamic acid may be divided into three doses of two tablets each with each tablet containing 1 gram tranexamic acid, or may be divided into four doses of two tablets each with each tablet containing 0.75 gram tranexamic acid. For ease of swallowing, the dose of tranexamic acid taken at each dosing time may be delivered by taking multiple tablets. For example, the 4 gram daily dose may be delivered by taking two 666.67 mg tablets three times a day or two 500 mg tablets four times a day. Similarly, the 3 gram daily dose may be achieved by taking two 550 mg tablets three times a day or two 375 mg tablets four times a day. Alternatively, for ease of reference, a dose of 600 mg, 650 mg, or 700 mg of tranexamic acid per tablet may be used. In a preferred embodiment, a total daily dose of 3900 mg/day is administered in three divided doses of 1300 mg of two tablets at each dose with each tablet containing 650 mg of tranexamic acid. Alternatively, each dose may be delivered by taking granules containing the prescribed amount of tranexamic acid presented in a convenient unit dose package. Such examples are not limiting and other doses within these ranges will be appreciated by those skilled in the art.

Since tranexamic acid is primarily eliminated via the kidneys by glomerular filtration with more than 95% excreted unchanged drug in the urine, dosage adjustment may be recommended. The table below lists some recommended dosage adjustments for renal impairment:

| Dose Adjustment Table | | | |
|---|---|---|---|
| Serum Creatinine (mg/dl) | Estimated GFR* (ml/min) | Adjusted dose | Total daily dose |
| 1.4 to 2.8 | 30-60 | 1.3 g (two 650 mg tablets) BID | 2.6 g |
| 2.8 to 5.7 | 15-30 | 1.3 g (two 650 mg tablets) QD | 1.3 g |
| >5.7 | <15 | 1.3 g (two 650 mg tablets) every 48 hours or 650 mg (one tablet) every 24 hours | 0.65 g |

Alternatively, modified release tranexamic acid formulations may be administered by pellets or granules in e.g., a sachet or capsule. Modified release tranexamic acid pellets or granules may be prepared by using materials to modify the release of tranexamic acid from the granule or pellet matrix. Modified release preparations may also be formulated using coatings to modify the release of tranexamic acid from the granule or pellet. U.S. Pat. Nos. 5,650,174; and 5,229,135 each of which is expressly incorporated by reference herein in its entirety, disclose variations on fabricating a pellet or nonpareil dosage form. Spheres are filled into packets, termed sachets, or capsules which are filled by weight to contain the prescribed dose of drug. Multiparticulates may be coated with an modified release coating, as disclosed in U.S. Pat. No. 6,066,339, which is expressly incorporated by reference herein its entirety. Coated multiparticulates may be packaged in capsules or sachets. The formulation of granules or pellets for modified release is described in Multiparticulate Oral Drug Delivery, Ghebre-Sellassie, Ed. in Drugs and the Pharmaceutical Sciences, Vol. 65 Marcel Dekker Inc. NY, 1994 and in the relevant parts of the references for modified release formulations previously cited and the relevant portions incorporated herein by reference.

Additional tranexamic acid formulations are disclosed in U.S. patent application Ser. Nos. 10/631,371, filed Jul. 31, 2003; 12/220,241, filed Jul. 23, 2008; and 11/346,710, filed Feb. 3, 2006, the disclosures of which are hereby incorporated by reference in their entirety.

In certain embodiments, the inventive tranexamic acid formulations may be used for additional indications other than menorrhagia, such as conization of the cervix, epistaxis, hyphema, hereditary angioneurotic edema, a patient with a blood coagulation disorder undergoing dental surgery, combinations thereof, and the like.

Menorrhagia Instrument

With regard to the treatment of menorrhagia (Heavy Menstrual Bleeding) studies of the safety and efficacy of the antifibrinolytic tranexamic acid were conducted. As part of these studies a diagnosis and treatment instrument (Mnorrhagia Instrument; MI) was designed. The instrument reliably identifies and monitors heavy menstrual bleeding patients and can be used in conjunction with an antifibrinolytic agent to diagnose and monitor the treatment of heavy menstrual bleeding.

A Menorrhagia Instrument (MI) of the invention reliably captures the diagnosis and treatment of the disease by measuring the impact of treatment on the symptoms associated with heavy menstrual bleeding. The information obtained from individual patient responses to the measures described in the methods of the present invention correlates to blood loss as measured by the alkaline hematin test. For example, data from the measures of social, leisure and/or physical activity symptoms, correlate with the volume of blood loss, and the change in the intensity of these symptoms correlates with the change in volume of blood lost, thus providing a measurement for the successful diagnosis and evaluation of treatment of bleeding disorders.

The instrument of the present invention measures specific aspects of the patient's monthly menstrual period. The measures correlate with the diagnosis of heavy menstrual bleeding and with the course of antifibrinolytic treatment. Further each of the measures individually correlate with quantity of blood loss as measured by the alkaline Hematin test. The symptomatic measures include: 1) a functional assessment measure; and ii) a pharmacology (or therapy assessment) measure.

The functional assessment measure of symptoms is further factored into segments which include 1) a measure of functional impairment generally; 2) impairment of necessary activities; and 3) impairment of discretionary activities.

The pharmacology domain provides an assessment of the severity of the menstrual period.

Specific symptomatic measures may be directed to an initial patient assessment and to the treatment period (pharmacology measure). Examples of specific measures would include examples of initial patient assessment measures (measures 1-4 listed in the Menorrhagia Instrument of FIG. 7); and therapy assessment measures (measures 1-4 together with measures 6, 6a, 6b and 6c contained in the Menorrhagia Instrument of FIG. 7).

In certain embodiments, the present invention is directed to a method of diagnosing and treating heavy menstrual bleeding, wherein the initial diagnoses of heavy menstrual bleeding is accomplished by evaluation of the most recent menstrual period on the basis of one, some or all of the prescribed symptomatic measures of FIG. 7. Measures which may be used as part of the initial patient assessment include, for example: a) determining a patient's perceived blood loss during their most recent menstrual period; b) determining how much the patient's blood loss limited their work outside and inside the home; c) determining how much the patient's blood loss limited their physical activities; d) determining how much the patient's blood loss limited their social and leisure activities; and e) determining the specific activities that were limited by the patient's blood loss.

The assessment of the patient's perceived blood loss during their most recent menstrual period may include an inquiry such as "during your most recent menstrual period, your blood loss was". The assessment may then quantify the patient response as a blood loss that was: i) light, ii) moderate, iii) heavy, or iv) very heavy. Alternatively, the measure may be quantified in terms of a scale of from one to four where one represents light, two represents moderate, three represents heavy and four represents very heavy.

The assessment of a patient's limitation due to the blood loss may include and evaluation of the patient's blood loss limitation on physical activities and/or how much the patient's blood loss limited their social and leisure activities. Assessment of the limitations on work, physical, social and leisure activities may be quantitated as: i) not at all, ii) slightly, iii) moderately, iv) quite a bit, or v) extremely. Alternatively the measure may be quantified in terms of a scale of from one to five where one represents not at all, two represents slightly, three represents moderately, four represents quite a bit, and five represents extremely.

Activities limited may include, but are not limited to, walking, standing, climbing stairs, squatting or bending down, playing with children and attending school activities. Home management activities include, but are not limited to, cooking, cleaning, yard work, and laundry. Leisure activities may include, but are not limited to, dancing, dinner, and movies. Sports activities may include, but are not limited to, tennis, golf, running, swimming, hiking, biking, boating, baseball, softball, basketball, soccer, fencing, volleyball, and other sports related activities.

Once the initial patient assessment measures have been completed and the patient has been identified as in need of treatment, the patient is administered a therapeutically effective treatment regimen of an antifibrinolytic agent. Suitable antifibrinolytic agents contemplated for use in the present invention include, but are not limited to tranexamic acid, aminocaproic acid, pharmaceutically acceptable salts, esters, derivatives, pro-drugs, metabolites, and analogues of any of the foregoing antifibrinolytic agents.

In certain embodiments the preferred antifibrinolytic agent is tranexamic acid. The tranexamic acid utilized in the present invention can be formulated into any suitable dosage form. Preferably, the tranexamic acid is in the form of a release modified tranexamic acid formulation.

When the preferred antifibrinolytic is tranexamic acid, the therapeutically effective treatment regimen contemplated by the present invention includes administration of a single dose of a tranexamic acid ranging from about 650 mg to about 1300 mg three (3) times a day for at least one day of menstruation, but not more than five days (or 15 single doses). The treatment regimen may be administered for at least one day; for at least the first two days, for at least the first three days, for days two through three, for days two to three, for the duration of menstruation.

In certain embodiments the tranexamic acid treatment regimen for treating the heavy menstrual bleeding includes administration of a single dose of about 650 mg to about 1.3 gm of a modified release formulation three (3) times a day, wherein the modified release formulation contains the tranexamic acid in combination with a modified release material In certain other embodiments, the present invention is directed to a method of evaluating the effectiveness of a treatment regimen administered for heavy menstrual bleeding.

Evaluation of the effectiveness of the treatment regimen can be initiated at the end of the patient's menstrual period, but prior to completion of the menstrual cycle. The post-menstruation measures provide in part the pharmacology (or therapy assessment) measure described above.

The pharmacology assessment may begin with one or more of the same series of measures utilized during the initial patient assessment, which include: a) determining a patient's perceived blood loss volume during their most recent menstrual period; b) determining how much the patient's blood loss limited their work outside and inside the home; c) determining how much the patient's blood loss limited their physical activities; d) determining how much the patient's blood loss limited their social and leisure activities; e) determining the specific activities that were limited by the patient's blood loss.

Alternatively, an evaluation of the effectiveness of the treatment regimen may require determining the change in the patient's perceived blood loss during the most recent menstrual period in comparison to the blood loss during the patient's previous menstrual period, measure 1 of FIG. 7 and/or an assessment of the improvement achieved, measure 6 of FIG. 7.

For example, a change in the patients perceived blood loss of about one unit for example from "heavy" to "moderate" or from a score of 3 ("heavy") to a score of 2 ("moderate") would provide the basis for continued treatment. While a perceived loss of less than one unit would suggest either a discontinuation of treatment or a second course after which the evaluation would be reconsidered. Alternatively, or in addition to the blood loss assessment, the practitioner may rely on the assessment in which the comparison of perceived loss is assessed as: i) "about the same", ii) "better", and iii) "worse", as prescribed in measure 6 in FIG. 1. When a patient's response is "about the same", an alternative treatment regimen may be considered for the next menstrual period. The practitioner may also reconsider re-administering the same treatment regimen for an additional menstrual period and later re-evaluate. When a patient's response is "better", the assessment may continue by requiring the patient to provide further information about the improvement in menstrual bleeding. For example, the assessment may include "if your menstrual bleeding improved since your last period, please indicate how much" (measure 6b of the MI of FIG. 7). Answers to this inquiry about an improvement in menstrual bleeding may require the patient to provide an answer such as: i) a very great deal better; ii) a great deal better; iii) a good deal better; iv) an average amount better; v) somewhat better; vi) a little better; or vii) almost the same, hardly better at all. Alternatively the answers can be scaled on a seven unit scale where "a very great deal better" is assigned a value of 7 and "almost the same" is valued as 7.

When a patient's response to measure 6 is "worse", the inquiry continues by requiring the patient to provide further data characterizing the change in menstrual bleeding. For example, the inquiry may determine "if your menstrual period worsened since your last period, please indicate how much" (measure 6c of MI of FIG. 7). Data for this measure to a worsening in menstrual bleeding may require the patient to provide a ranking such as: i) "a very great deal worse"; ii) "a great deal worse"; iii) "a good deal worse"; iv) "an average amount worse"; v) "somewhat worse"; vi) "a little worse"; or vii) "almost the same, hardly worse at all". As before the answers may be scaled on a seven unit scale where −1 is "almost the same" and −7 is "a very great deal worse".

The comparison of perceived blood loss which results in an improvement of at least one unit as measured by measure 1 of FIG. 7 and/or an assessment of a perceived blood loss which is "better" as provided in measure six of FIG. 1 may proceed by assessing whether the improvement "was a meaningful or an important change" to the patient (measure 6c of MI of FIG. 7).

The information obtained about the "improvement" or "worsening" in menstrual bleeding allows the practitioner to make an evaluation of the effectiveness of the treatment regimen which correlates with the change in blood loss as measured by the alkaline hematin test and demonstrated with clinical trial data.

The method for evaluating the effectiveness of a treatment regimen of the present invention may be repeated after each menstrual period. The data obtained from the initial patient assessment and the subsequent pharmacology (therapy assessment) can be stored into a computer database and utilized for future diagnostic and/or evaluation purposes.

In certain other embodiments, the present invention is directed to a method of treating heavy menstrual bleeding. The method involving, evaluating symtomatic data gathered from the measures individually or collectively as described in FIG. 1. (items one through four and six as discussed above) to determine the need for therapy and then administering, to a patient in need, a therapeutically effective treatment regimen of an antifibrinolytic agent, e.g., a release modified tranexamic acid formulation, wherein the treatment regimen is to be administered for part or for the duration of menstruation, but no longer than 5 days during the patient's menstrual cycle.

The present invention is further described with regard to the following examples.

DETAILED DESCRIPTION OF PREFERRED EMBODIMENTS

The invention will be further appreciated with respect to the following non-limiting examples. Other variations or embodiments of the invention will also be apparent to one of ordinary skill in the art from the above descriptions and examples. Thus, the forgoing embodiments are not to be construed as limiting the scope of this invention.

Example 1

Modified release 650 mg tranexamic acid tablets were prepared having the ingredients listed in the Table 1 below:

TABLE 1

| Ingredient | Quantity per batch (kg) | Quantity per tablet (mg) |
|---|---|---|
| Active Ingredient | | |
| Tranexamic Acid, EP | 84.50 | 650.0 |
| Inactive Ingredients | | |
| Microcrystalline Cellulose NF (Avicel PH 101) | 5.753 | 44.25 |
| Colloidal Silicon Dioxide NF | 0.0975 | 0.75 |
| Pregelatinized Corn Starch, NF | 6.435 | 49.50 |
| Hypromellose, USP (Methocel K3 Premium LV) | 19.110 | 147.00 |
| Povidone, USP (K value range 29-32) | 4.680 | 36.00 |
| Stearic Acid, NF (powder) | 2.340 | 18.00 |
| Magnesium Stearate, NF (powder) | 0.585 | 4.50 |
| Purified Water USP* | 17.550 | 135.00 |

*Purified water is removed during processing

The formulation of Example 1 was prepared as follows:
1. Weigh all ingredients and keep in moisture resistant containers until ready for use.
2. Measure water into a container. Mix povidone at medium speed until completely dissolved.
3. Add tranexamic acid, microcrystalline cellulose (MCC), pregelatinized corn starch, and colloidal silicon dioxide to the high shear mixer.
4. Mix using impeller only.
5. Mix for an additional time (impeller only). Add all of the povidone solution during this mixing step.
6. Mix until adequately granulated (impeller and chopper). Proceed only when desired granulation has been achieved. Add additional water if necessary.
7. Dry the granulation to moisture content of NMT 1.2%.
8. Pass the granulation through the oscillating granulator equipped with a #30 mesh screen. Weigh the granulation. Add granulation to the V-Blender.
9. Add the hypromellose USP Methocel K3 Premium to the V-blender. Blend.
10. Pass magnesium stearate and stearic acid through oscillating granulator equipped with a #40 mesh screen. Add magnesium stearate and stearic acid to the V-blender and blend.

11. Perform specified physical property testing. Proceed to compression.
12: Compress tablets to desired weight.

Example 2

In Example 2, immediate release 650 mg tranexamic acid tablets were prepared having the ingredients listed in Table 2 below:

TABLE 2

| Ingredient | Quantity per batch (kg) | Quantity per tablet (mg) |
|---|---|---|
| Active Ingredient | | |
| Tranexamic Acid, EP (650 mg/tab) | 84.50 | 650.0 |
| Inactive Ingredients | | |
| Microcrystalline Cellulose, NF (Avicel PH 101) | 5.753 | 44.25 |
| Microcrystalline Cellulose, NF (Avicel PH 102) | 10.660 | 82.00 |
| Colloidal Silicon Dioxide, NF | 0.0975 | 0.75 |
| Pregelatinized Corn Starch, NF | 6.435 | 49.50 |
| Croscarmellose Sodium, NF | 19.50 | 15.00 |
| Povidone, USP (K value range 29-32) | 4.680 | 36.00 |
| Stearic Acid, NF (powder) | 2.340 | 18.00 |
| Magnesium Stearate, NF (powder) | 0.585 | 4.50 |
| Purified Water, USP* | 17.550 | 135.00 |
| Film Coating (Inactive Ingredients)** | | |
| Opadry White YS-1-7003 | 4.110 | — |
| Purified Water, USP | 36.990 | — |

*Purified water is removed during processing
**6 kg excess prepared to account for losses during transfer The formulation of Example 2 was prepared as follows:
1. Weigh all ingredients and keep in moisture resistant containers until ready for use.
2. Measure water into a container. Mix povidone at medium speed until completely dissolved.
3. Add tranexamic acid, microcrystalline cellulose (MCC), pregelatinized corn starch, and colloidal silicon dioxide to the high shear mixer.
4. Mix using impeller only.
5. Mix for an additional time (impeller only). Add all of the povidone solution during this mixing step.
6. Mix until adequately granulated (impeller and chopper). Proceed only when desired granulation has been achieved. Add additional water if necessary.
7. Dry the granulation to moisture content of NMT 1.2%.
8. Pass the granulation through the oscillating granulator equipped with a #30 mesh screen. Weigh the granulation. Add granulation to the V-Blender.
9. Add the croscarmellose sodium and MCC to the V-Blender and blend.
10. Pass magnesium stearate and stearic acid through oscillating granulator equipped with a #40 mesh screen. Add magnesium stearate and stearic acid to the V-blender and blend.
11. Perform specified physical property testing. Proceed to compression.
12. Compress tablets.
12. After compression, spray coat the compressed dosage forms with the Opadry White in water.

Example 3

In Example 3, modified release 650 mg tranexamic acid tablets were prepared as in Example 1 and coated with a film coating similar to the immediate release tablets of Example 2. The ingredients are listed in Table 3 below:

TABLE 3

| Ingredient | Quantity per batch (kg) | Quantity per tablet (mg) |
|---|---|---|
| Active Ingredient | | |
| Tranexamic Acid, EP | 84.50 | 650.0 |
| Inactive Ingredients | | |
| Microcrystalline Cellulose NF (Avicel PH 101) | 5.753 | 44.25 |
| Colloidal Silicon Dioxide NF | 0.0975 | 0.75 |
| Pregelatinized Corn Starch, NF | 6.435 | 49.50 |
| Hypromellose, USP (Methocel K3 Premium LV) | 19.110 | 147.00 |
| Povidone, USP (K value range 29-32) | 4.680 | 36.00 |
| Stearic Acid, NF (powder) | 2.340 | 18.00 |
| Magnesium Stearate, NF (powder) | 0.585 | 4.50 |
| Purified Water USP* | 17.550 | 135.00 |
| Film Coating (Inactive Ingredients)** | | |
| Opadry White YS-1-7003 | 4.305 | — |
| Purified Water, USP | 38.750 | — |

*Purified water is removed during processing
**6 kg excess prepared to account for losses during transfer

Example 3a

Example 3A, delayed release 650 mg tranexamic acid tablets were prepared having the ingredients listed in Table 3A below:

TABLE 3A

| Ingredient | Quantity per batch (kg) | Quantity per tablet (mg) |
|---|---|---|
| Active Ingredient | | |
| Tranexamic Acid, EP | 84.50 | 650.0 |
| Inactive Ingredients | | |
| Microcrystalline Cellulose NF (Avicel PH 101) | 5.753 | 44.25 |
| Microcrystalline Cellulose NF (Avivel PH 102) | 10.660 | 82.00 |
| Colloidal Silicon Dioxide NF | 0.0975 | 0.75 |
| Pregelatinized Corn Starch, NF | 6.435 | 49.50 |
| Croscarmellose Sodium NF | 19.50 | 15.00 |
| Povidone, USP (K value range 29-32) | 4.680 | 36.00 |
| Stearic Acid, NF (powder) | 2.340 | 18.00 |
| Magnesium Stearate, NF (powder) | 0.585 | 4.50 |
| Purified Water USP* | 17.550 | 135.00 |
| Film Coating (Inactive Ingredients)** | | |
| Acryl-Eze (930185359) | 12.90 | — |
| Silicone Emulsion, 30% | 0.323 | — |
| Purified Water, USP | 51.271 | — |

*Purified water is removed during processing; mg per tablet is based on theoretical specific gravity of 1.0 g/ml
**6 kg excess prepared to account for losses during transfer The formulation of Example 3A was prepared as follows:
1. Weigh all ingredients and keep in moisture resistant containers until ready for use.
2. Measure water into a container. Mix povidone at medium speed until completely dissolved.
3. Add tranexamic acid, microcrystalline cellulose (MCC), pregelatinized corn starch, and colloidal silicon dioxide to the high shear mixer.
4. Mix using impeller only.
5. Mix for an additional time (impeller only). Add all of the povidone solution during this mixing step.

6. Mix until adequately granulated (impeller and chopper). Proceed only when desired granulation has been achieved. Add additional water if necessary.
7. Dry the granulation to moisture content of NMT 1.2%.
8. Pass the granulation through the oscillating granulator equipped with a #30 mesh screen. Weigh the granulation. Add granulation to the V-Blender.
9. Add the croscarmellose sodium and MCC to the V-Blender and blend.
10. Pass magnesium stearate and stearic acid through oscillating granulator equipped with a #40 mesh screen. Add magnesium stearate and stearic acid to the V-blender and blend.
11. Perform specified physical property testing. Proceed to compression.
12. Compress tablets.
13. After compression, spray coat the compressed dosage forms with the film coating.

Dissolution results for the delayed release formulation of Example 3A (in base stage) are listed below in Table 3B.

Dissolution Results for the Delayed Release Formulation (in Base Stage)

TABLE 3B

| Time (min.) | Dissolution (%) | Standard Deviation |
| --- | --- | --- |
| 15 | 16% | ±6.013873 |
| 30 | 89% | ±14.06769 |
| 45 | 95% | ±2.810694 |
| 60 | 97% | ±2.345208 |

Example 4

Bioavailability and Bioequivalence Evaluation

In Example 4, a comparative, randomized, single dose, 4-way Crossover Absolute Bioavailability (BA) and Bioequivalence (BE) study of Tranexamic Acid Tablet Formulations prepared in accordance with Examples 1 and 2 in Healthy Adult Women Volunteers under Fasting Conditions was performed. The objective was to assess the bioequivalence of a 650 mg modified release tablet formulation prepared in accordance with Example 1 compared to the immediate release reference tablet formulation of tranexamic acid prepared in accordance with Example 2, and to determine the bioavailability of the modified tablet formulation to the approved IV (1 g) formulation Cyklokapron® by Pharmacia & Upjohn. The design was a randomized, 4-way crossover, comparative BE and BA determination. All oral doses administered were 1.3 g. Twenty-eight (28) healthy non-smoking adult female volunteer subjects were enrolled in the study. A total of 26 subjects completed the study. Sample size was calculated assuming a 25% CV in $AUC_{inf}$. The study endpoints were the 90% confidence intervals of the ratio of least-squares means of the pharmacokinetic parameters $AUC_{0-t}$, $AUC_{inf}$ and $C_{max}$ of the modified release formulation to the immediate-release formulation from serum concentration-time data drawn up to 36 hours after a single dose of drug. In addition, the bioavailability of the tablet formulations were calculated. Smokers, oral contraceptive users, those with a previous history of thromboembolic events and altered vision were excluded from the study. ECG monitoring was performed before, during and after the estimated times of peak serum tranexamic acid concentrations exposure. Adverse events were captured and recorded throughout the trial period.

In the study, subjects were randomized to receive single oral 1.3 g (2×650 mg tablets) dose of tranexamic acid in tablet forms which included a modified release dosage form and an immediate release dosage form. Subjects were also administered a single 1 g (10 ml) IV solution of tranexamic acid (100 mg/ml concentration).

A summary of the pharmacokinetic results from the study of Example 4 are listed in the tables below.

TABLE 4

Summary of Results - Tranexamic Acid in Plasma Pharmacokinetic Parameters (N = 26)

| | ln AUC 0-t* (mcg · h/mL) | ln AUCinf* (mcg · h/mL) | ln Cmax* (mcg/mL) |
| --- | --- | --- | --- |
| Modified Release formulation | | | |
| Mean | 66.703 | 69.642 | 11.251088 |
| CV | 26.8 | 27.2 | 29.1 |
| N | 26 | 24 | 26 |
| Immediate Release formulation | | | |
| Mean | 70.157 | 72.656 | 12.260414 |
| CV | 16.2 | 16.4 | 23.0 |
| N | 26 | 24 | 26 |
| Least-Squares Mean: | | | |
| Modified Release | 66.935 | 68.891 | 11.321919 |
| Immediate Release | 70.051 | 72.411 | 12.258222 |
| Ratio of Least-Squares Mean (modified release/immediate release) % | 95.6 | 95.1 | 92.4 |

*For ln-transformed parameters, the antilog of the mean (i.e. the geometric mean) is reported.
AUCinf, kel, half-life and F could not be estimated for some subjects.
AUC 0-t is the area under the plasma concentration versus time curve, from time 0 to the last measurable concentration, as calculated by the linear trapezoidal method.

TABLE 5

Summary of Results - Tranexamic Acid in Plasma Pharmacokinetic Parameters (N = 26)

| | Tmax (h) | Half-life (h) | kel (1/h) | F (%) |
| --- | --- | --- | --- | --- |
| Modified Release formulation | | | | |
| Mean | 2.942 | 11.370 | 0.06300 | 44.93 |
| CV | 22.7 | 17.6 | 19.4 | 25.3 |
| n | 26 | 26 | 26 | 24 |
| Immediate Release formulation | | | | |
| Mean | 2.808 | 11.013 | 0.06438 | 46.04 |
| CV | 20.8 | 15.5 | 15.3 | 16.1 |
| n | 26 | 24 | 24 | 24 |

TABLE 6

Summary of Results - Tranexamic Acid in Plasma Pharmacokinetic Parameters (N = 26)

|  | Ln AUC 0-t* (mcg · h/mL) | ln AUCinf* (mcg · h/mL) | ln Cmax* (mcg/mL) |
|---|---|---|---|
| 90% Confidence Intervals (Modified release/Immediate release) % | | | |
| lower limit: | 87.8% | 87.4% | 84.0% |
| upper limit: | 104.0% | 103.5% | 101.6% |
| p-Value (ANOVA) | | | |
| Modified vs Immediate | 0.3721 | 0.3259 | 0.1676 |
| Period | 0.0704 | 0.0499 | 0.0356 |
| Sequence | 0.7734 | 0.7978 | 0.8207 |
| Intrasubject CV % | 18.3 | 17.4 | 20.6 |

*For ln-transformed parameters, the antilog of the mean (i.e. the geometric mean) is reported.
AUCinf, kel, half-life and F could not be estimated for some subjects.

Figure 3:
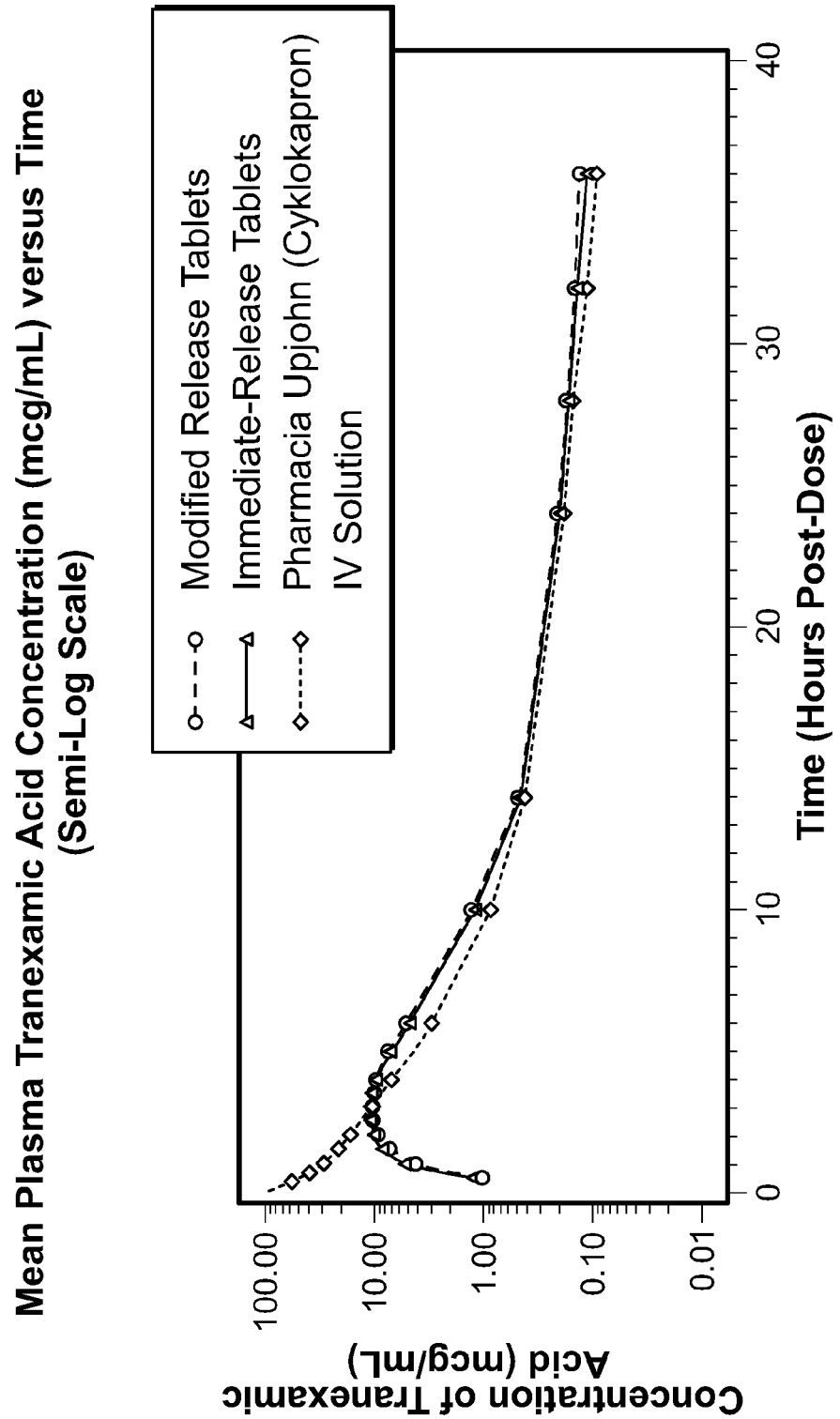
FIG. 3 depicts mean plasma concentration-time profiles on a semi-log scale over 36 hours for the study of Example 4.
Figure 4:
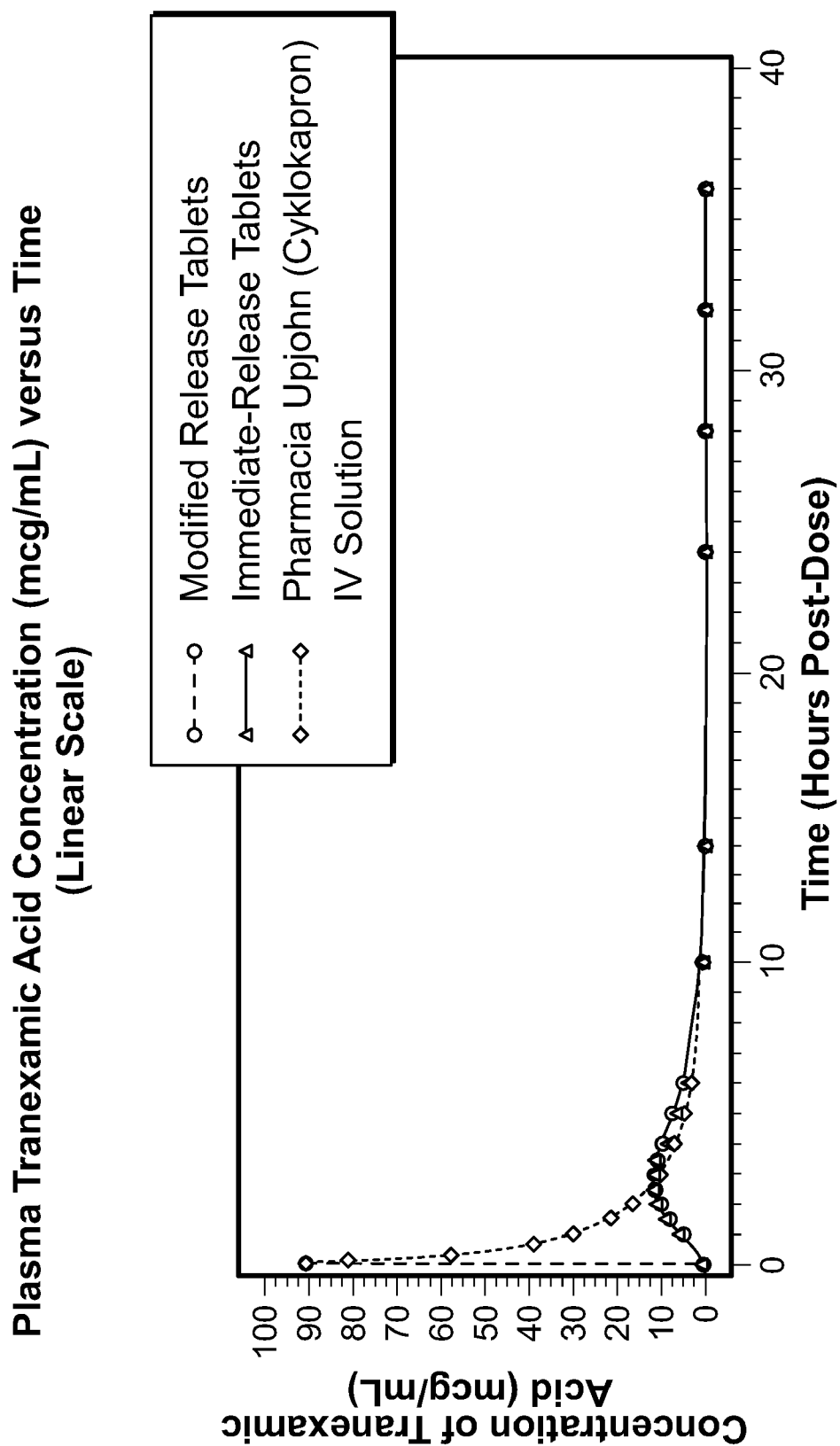
FIG. 4 depicts mean plasma concentration-time profiles on a linear scale over 36 hours for the study of Example 4.
Figure 5:
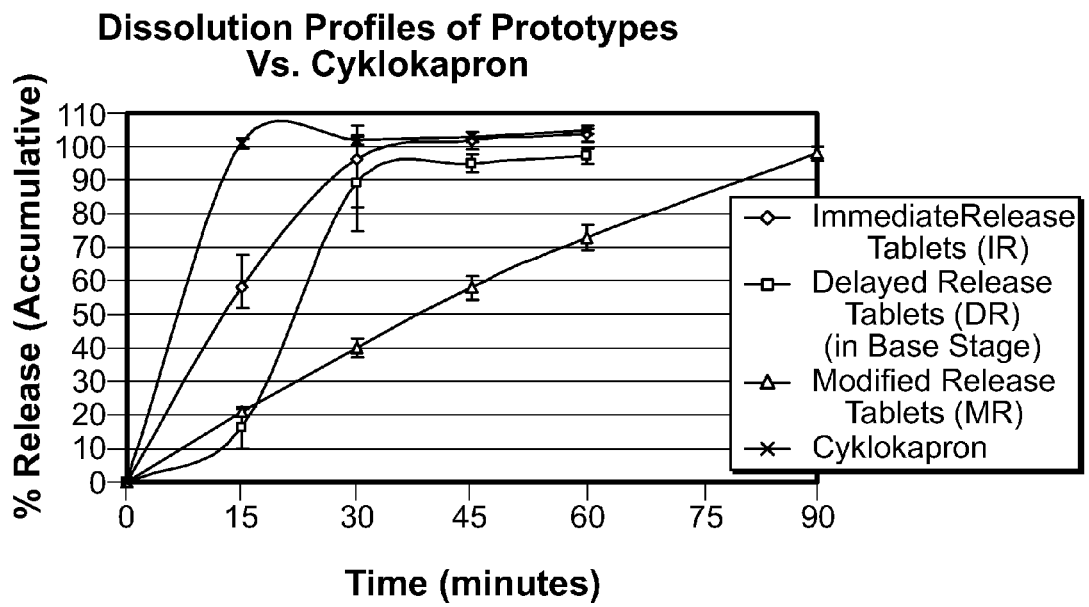
FIG. 5 depicts the dissolution profiles of the modified release tranexamic acid formulation of Example 1; the immediate release tranexamic acid formulation of Example 2; the delayed release tranexamic acid formulation of Example 3A, and the commercial Cyklokapron immediate release formulation of Example 4A.
Figure 6:
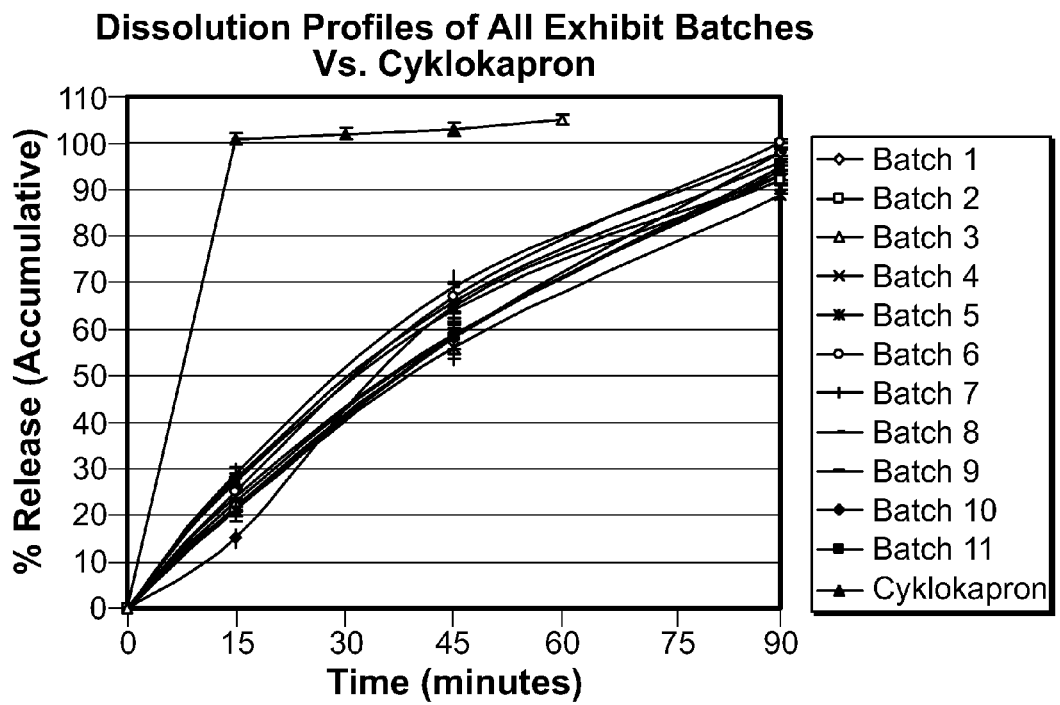
FIG. 6 depicts the dissolution profile of all of the exhibit batches of the modified release tranexamic acid formulations of the present invention and the commercial Cyklokapron immediate release formulation of Example 4A.

Concentration-time profiles for the study of Example 4 are presented on semi-log and linear scale over 36 hours and are depicted in FIGS. 3 and 4.

The following pharmacokinetic parameters in the table below were calculated for tranexamic acid in plasma for the study of Example 4.

MRT: The mean residence time (MRT) after intravenous administration of tranexamic acid was determined using the equation, AUMC/AUC+infusion time/2, where the AUMC is the area under the moment-time curve.

MTT: Following oral administration of the Modified Release and Immediate Release formulations, the mean transit time (MTT) of tranexamic acid was calculated by dividing the AUMC by the AUC.

MAT: The mean absorption time (MAT) for the two formulations was derived by subtracting the MRT from the MTT.

Mean (±SD) results are presented in the table below:

TABLE 7

|  | IV | Modified Release | Immediate Release |
|---|---|---|---|
| MRT (hours) | 3.51 ± 0.38 | N/A | N/A |
| MTT (hours) | N/A | 7.70 ± 0.72 | 7.21 ± 1.01 |
| MAT (hours) | N/A | 4.18 ± 0.70 | 3.70 ± 0.94 |

The mean transit time (MTT) and mean absorption time (MAT) of the Modified Release formulation of tranexamic acid was approximately 30 minutes longer than that observed for the Immediate Release formulation.

The most frequently reported adverse events from the study of Example 4 are listed in the table below. The table lists the number of subjects reporting adverse events, and the percentage of subjects is in parentheses.

TABLE 8

| Adverse Events | Treatment | | |
|---|---|---|---|
|  | Modified Release (2 × 650 mg) (n = 27) | Immediate Release (2 × 650 mg) (n = 27) | IV solution (10 × 100 mg/ml) (n = 27) |
| Headache | 4 (15%) | 7 (26%) | 7 (26%) |
| Nausea | 0 (0%) | 2 (7%) | 10 (37%) |
| Dizziness | 0 (0%) | 0 (0%) | 11 (41%) |
| Feeling Hot | 0 (0%) | 0 (0%) | 6 (22%) |
| Nasal Congestion | 2 (7%) | 1 (4%) | 1 (4%) |
| Cough | 0 (0%) | 0 (0%) | 2 (7%) |
| Urine odor abnormal | 2 (7%) | 0 (0%) | 1 (4%) |

Dissolution Results for Immediate Release and Modified Release Formulations prepared in accordance with Examples 2 and 1 respectively used in the study of Example 4 tested under USP 27 Apparatus Type II Paddle Method @ 50 RPM in 900 ml water at 37±0.5° C. are listed in the tables below.

TABLE 9

Dissolution Results for the Immediate Release Formulation in Table 2.

| Time (min.) | Dissolution (%) | Standard Deviation |
|---|---|---|
| 15 | 58.0% | ±9.521905 |
| 30 | 96.0% | ±10.2697 |
| 45 | 102.0% | ±0.408248 |
| 60 | 104.0% | ±1.032796 |

TABLE 10

Dissolution Results for the Modified Release Formulation in Table 1

| Time (min.) | Dissolution (%) | Standard Deviation |
|---|---|---|
| 15 | 21.0% | ±1.414214 |
| 30 | 40.0% | ±2.810694 |
| 45 | 58.0% | ±3.600926 |
| 60 | 73.0% | ±3.81663 |
| 90 | 98.0% | ±2.097618 |

TABLE 10A

Dissolution Results for the Various Batches of the Modified Release Formulation Table 1

| Batch # | 0 min | 15 min | 45 min | 90 min |  | Standard Deviation | | |
|---|---|---|---|---|---|---|---|---|
| Batch 1 | 0 | 21 | 58 | 98 | 0 | ±1.386 | ±3.48 | ±2.254 |
| Batch 2 | 0 | 21 | 58 | 95 | 0 | ±1.134 | ±3.074 | ±2.47 |
| Batch 3 | 0 | 23 | 59 | 93 | 0 | ±2.323 | ±4.366 | ±3.627 |
| Batch 4 | 0 | 21 | 56 | 89 | 0 | ±1.575 | ±3.808 | ±2.492 |
| Batch 5 | 0 | 24 | 59 | 93 | 0 | ±2.016 | ±3.422 | ±2.139 |
| Batch 6 | 0 | 25 | 67 | 100 | 0 | ±1.45 | ±3.149 | ±0.9 |
| Batch 7 | 0 | 22 | 58 | 94 | 0 | ±0.968 | ±2.32 | ±2.068 |
| Batch 8 | 0 | 29 | 69 | 98 | 0 | ±2.03 | ±3.726 | ±1.666 |
| Batch 9 | 0 | 28 | 66 | 96 | 0 | ±2.268 | ±3.762 | ±2.688 |
| Batch 10 | 0 | 15 | 65 | 93 | 0 | ±1.904 | ±2.47 | ±2.604 |
| Batch 11 | 0 | 27 | 64 | 92 | 0 | ±1.836 | ±2.368 | ±2.024 |

CONCLUSIONS

The ratios of least-squares means and the 90% confidence intervals derived from the analyses of the ln-transformed pharmacokinetic parameters $AUC_{0-t}$, $AUC_{inf}$ and $C_{max}$ for tranexamic acid in plasma were within the 80-125% Food and Drug Administration (FDA) acceptance range for the modified release formulation versus the immediate release formulation under fasting conditions.

The absolute bioavailability of the modified release and immediate release tablet formulations were 44.93% and 46.04% respectively.

Based on these results, the modified release tranexamic acid tablet formulation and the immediate release tranexamic acid formulation are bioequivalent under fasting conditions.

Example 4a

Comparative Example

In Comparative Example 4A, a 500 mg immediate release tranexamic acid tablet, approved and marketed in Canada under the name Cyklokapron was obtained and dissolution tested under USP 27 Apparatus Type II Paddle Method @ 50 RPM in 900 ml water at 37±0.5° C. The dissolution results are listed in Table 10A below:

TABLE 10A

| Sample # | % dissolved in 15 min. | % dissolved in 30 min. | % dissolve in 45 min. | % dissolved in 60 min. |
|---|---|---|---|---|
| 1 | 102 | 104 | 105 | 106 |
| 2 | 102 | 104 | 105 | 106 |
| 3 | 101 | 102 | 102 | 105 |
| 4 | 99 | 101 | 102 | 103 |
| 5 | 100 | 102 | 103 | 104 |
| 6 | 99 | 101 | 102 | 104 |
| Average | 101 | 102 | 103 | 105 |
| % RSD | 1.4 | 1.3 | 1.4 | 1.1 |

Example 5

In Example 5, based on single dose pharmacokinetic parameters, pharmacokinetic simulations of serum concentrations were performed to compare dosing the modified release formulation of Example 4 at every 8 hours (Q8H: at 6:00 AM, 2:00 PM, 10:00 PM) and dosing three times a day, other than every 8 hours (TID: at 8:00 AM, 2:00 PM, and 10:00 PM). The results are provided in Tables 11-14 below.

TABLE 11

Tranexamic Acid - Modified Release Formulation
Dosage Regimen Simulation - ORAL
1.3 g q8 hr

| Time (h) | Dose (mcg) | Conc. (mcg/mL) |
|---|---|---|
| 0 | 1.30E+06 | 0 |
| 1 | 0 | 4.0594 |
| 2 | 0 | 10.0551 |
| 3 | 0 | 10.6433 |
| 4 | 0 | 9.20306 |
| 5 | 0 | 7.26932 |
| 6 | 0 | 5.4699 |
| 8 | 1.30E+06 | 2.89909 |
| 9 | 0 | 6.15391 |
| 10 | 0 | 11.5813 |
| 11 | 0 | 11.7752 |
| 12 | 0 | 10.0646 |
| 13 | 0 | 7.94622 |
| 14 | 0 | 6.02067 |
| 15 | 0 | 4.4712 |
| 16 | 1.30E+06 | 3.30248 |
| 17 | 0 | 6.51406 |
| 18 | 0 | 11.9097 |

TABLE 11-continued

Tranexamic Acid - Modified Release Formulation
Dosage Regimen Simulation - ORAL
1.3 g q8 hr

| Time (h) | Dose (mcg) | Conc. (mcg/mL) |
|---|---|---|
| 19 | 0 | 12.0794 |
| 20 | 0 | 10.3495 |
| 21 | 0 | 8.21523 |
| 22 | 0 | 6.2761 |
| 23 | 0 | 4.71463 |
| 24 | 1.30E+06 | 3.53505 |
| 25 | 0 | 6.73663 |
| 26 | 0 | 12.1229 |
| 27 | 0 | 12.2838 |
| 28 | 0 | 10.5455 |
| 29 | 0 | 8.40336 |
| 30 | 0 | 6.45664 |
| 31 | 0 | 4.88791 |
| 32 | 1.30E+06 | 3.70138 |
| 33 | 0 | 6.89628 |
| 34 | 0 | 12.2762 |
| 35 | 0 | 12.4309 |
| 36 | 0 | 10.6868 |
| 37 | 0 | 8.53894 |
| 38 | 0 | 6.5868 |
| 39 | 0 | 5.01286 |
| 40 | 1.30E+06 | 3.82133 |
| 41 | 0 | 7.01144 |
| 42 | 0 | 12.3867 |
| 43 | 0 | 12.537 |
| 44 | 0 | 10.7887 |
| 45 | 0 | 8.63675 |
| 46 | 0 | 6.68069 |
| 47 | 0 | 5.103 |
| 48 | 1.30E+06 | 3.90786 |
| 49 | 0 | 7.09451 |
| 50 | 0 | 12.4665 |
| 51 | 0 | 12.6136 |
| 52 | 0 | 10.8621 |
| 53 | 0 | 8.70731 |
| 54 | 0 | 6.74842 |
| 55 | 0 | 5.16802 |
| 56 | 1.30E+06 | 3.97028 |
| 57 | 0 | 7.15443 |
| 58 | 0 | 12.524 |
| 59 | 0 | 12.6688 |
| 60 | 0 | 10.9152 |
| 61 | 0 | 8.7582 |
| 62 | 0 | 6.79728 |
| 63 | 0 | 5.21493 |
| 64 | 1.30E+06 | 4.01531 |
| 65 | 0 | 7.19766 |
| 66 | 0 | 12.5655 |
| 67 | 0 | 12.7087 |
| 68 | 0 | 10.9534 |
| 69 | 0 | 8.79492 |
| 70 | 0 | 6.83253 |
| 71 | 0 | 5.24877 |
| 72 | 1.30E+06 | 4.0478 |
| 73 | 0 | 7.22885 |
| 74 | 0 | 12.5954 |
| 75 | 0 | 12.7374 |
| 76 | 0 | 10.981 |
| 77 | 0 | 8.82141 |
| 78 | 0 | 6.85796 |
| 79 | 0 | 5.27318 |
| 80 | 1.30E+06 | 4.07124 |
| 81 | 0 | 7.25135 |
| 82 | 0 | 12.617 |
| 83 | 0 | 12.7581 |
| 84 | 0 | 11.0009 |
| 85 | 0 | 8.84052 |
| 86 | 0 | 6.87631 |
| 87 | 0 | 5.29079 |
| 88 | 1.30E+06 | 4.08814 |
| 89 | 0 | 7.26758 |
| 90 | 0 | 12.6326 |
| 91 | 0 | 12.7731 |
| 92 | 0 | 11.0153 |

TABLE 11-continued

Tranexamic Acid - Modified Release Formulation
Dosage Regimen Simulation - ORAL
1.3 g q8 hr

| Time (h) | Dose (mcg) | Conc. (mcg/mL) |
|---|---|---|
| 93 | 0 | 8.8543 |
| 94 | 0 | 6.88954 |
| 95 | 0 | 5.3035 |
| 96 | 1.30E+06 | 4.10034 |
| 97 | 0 | 7.27929 |
| 98 | 0 | 12.6439 |
| 99 | 0 | 12.7839 |
| 100 | 0 | 11.0256 |
| 101 | 0 | 8.86425 |
| 102 | 0 | 6.89909 |
| 103 | 0 | 5.31266 |
| 104 | 1.30E+06 | 4.10913 |
| 105 | 0 | 7.28773 |
| 106 | 0 | 12.652 |
| 107 | 0 | 12.7917 |
| 108 | 0 | 11.0331 |
| 109 | 0 | 8.87142 |
| 110 | 0 | 6.90597 |
| 111 | 0 | 5.31927 |
| 112 | 1.30E+06 | 4.11548 |
| 113 | 0 | 7.29382 |
| 114 | 0 | 12.6578 |
| 115 | 0 | 12.7973 |
| 116 | 0 | 11.0385 |
| 117 | 0 | 8.8766 |
| 118 | 0 | 6.91094 |
| 119 | 0 | 5.32404 |
| 120 | 0 | 4.12006 |

Concentration-time profiles are presented over 120 hours for the modified release formulation in Table 12 and are depicted in FIG. 1. A 1 g formulation administered q8h is also depicted for comparison purposes.

TABLE 12

Cmax, Cmin and Cavg for 1.3 g q8 hr simulation
Simulation at 120 hours

| Pharmacokinetic Parameter | Concentration |
|---|---|
| Cmax | 12.8 mcg/mL |
| Cmin | 4.1 mcg/mL |
| Cavg | 8.4 mcg/ml |

TABLE 13

Tranexamic Acid - Modified Release Formulation
Dosage Regimen Simulation - ORAL
1.3 g TID (8:00 AM, 2:00 PM, and 10:00 PM)

| Time (h) | Dose (mcg) | Conc. (mcg/mL) |
|---|---|---|
| 0 | 1.30E+06 | 0 |
| 1 | 0 | 4.0594 |
| 2 | 0 | 10.0551 |
| 3 | 0 | 10.6433 |
| 4 | 0 | 9.20306 |
| 5 | 0 | 7.26932 |
| 6 | 1.30E+06 | 5.4699 |
| 8 | 0 | 12.9542 |
| 9 | 0 | 12.7378 |
| 10 | 0 | 10.7293 |
| 11 | 0 | 8.40129 |
| 12 | 1.30E+06 | 6.33141 |
| 13 | 0 | 8.74352 |
| 14 | 0 | 13.505 |
| 15 | 0 | 13.2018 |
| 16 | 0 | 11.1327 |
| 17 | 0 | 8.76144 |
| 18 | 0 | 6.65976 |
| 19 | 0 | 4.98823 |
| 20 | 0 | 3.73474 |
| 21 | 0 | 2.8275 |
| 22 | 0 | 2.18502 |
| 23 | 0 | 1.73555 |
| 24 | 1.30E+06 | 1.42243 |
| 25 | 0 | 5.26298 |
| 26 | 0 | 11.104 |
| 27 | 0 | 11.5807 |
| 28 | 0 | 10.058 |
| 29 | 0 | 8.06103 |
| 30 | 1.30E+06 | 6.21137 |
| 31 | 0 | 8.76659 |
| 32 | 0 | 13.6187 |
| 33 | 0 | 13.3709 |
| 34 | 0 | 11.334 |
| 35 | 0 | 8.97998 |
| 36 | 1.30E+06 | 6.88576 |
| 37 | 0 | 9.27495 |
| 38 | 0 | 14.0147 |
| 39 | 0 | 13.6908 |
| 40 | 0 | 11.6019 |
| 41 | 0 | 9.21185 |
| 42 | 0 | 7.09208 |
| 43 | 0 | 5.40321 |
| 44 | 0 | 4.1331 |
| 45 | 0 | 3.20991 |
| 46 | 0 | 2.55212 |
| 47 | 0 | 2.08796 |
| 48 | 1.30E+06 | 1.76074 |
| 49 | 0 | 5.58776 |
| 50 | 0 | 11.4158 |
| 51 | 0 | 11.88 |
| 52 | 0 | 10.3453 |
| 53 | 0 | 8.33688 |
| 54 | 1.30E+06 | 6.47618 |
| 55 | 0 | 9.02081 |
| 56 | 0 | 13.8627 |
| 57 | 0 | 13.6052 |
| 58 | 0 | 11.5589 |
| 59 | 0 | 9.1959 |
| 60 | 1.30E+06 | 7.09304 |
| 61 | 0 | 9.47395 |
| 62 | 0 | 14.2057 |
| 63 | 0 | 13.8742 |
| 64 | 0 | 11.778 |
| 65 | 0 | 9.38036 |
| 66 | 0 | 7.25433 |
| 67 | 0 | 5.55898 |
| 68 | 0 | 4.28264 |
| 69 | 0 | 3.35346 |
| 70 | 0 | 2.68993 |
| 71 | 0 | 2.22026 |
| 72 | 1.30E+06 | 1.88775 |
| 73 | 0 | 5.70968 |
| 74 | 0 | 11.5329 |
| 75 | 0 | 11.9924 |
| 76 | 0 | 10.4532 |
| 77 | 0 | 8.44044 |
| 78 | 1.30E+06 | 6.57559 |
| 79 | 0 | 9.11625 |
| 80 | 0 | 13.9543 |
| 81 | 0 | 13.6931 |
| 82 | 0 | 11.6434 |
| 83 | 0 | 9.27696 |
| 84 | 1.30E+06 | 7.17086 |
| 85 | 0 | 9.54865 |
| 86 | 0 | 14.2775 |
| 87 | 0 | 13.943 |
| 88 | 0 | 11.8441 |
| 89 | 0 | 9.44431 |

TABLE 13-continued

Tranexamic Acid - Modified Release Formulation
Dosage Regimen Simulation - ORAL
1.3 g TID (8:00 AM, 2:00 PM, and 10:00 PM)

| Time (h) | Dose (mcg) | Conc. (mcg/mL) |
|---|---|---|
| 90 | 0 | 7.31525 |
| 91 | 0 | 5.61745 |
| 92 | 0 | 4.33877 |
| 93 | 0 | 3.40735 |
| 94 | 0 | 2.74167 |
| 95 | 0 | 2.26992 |
| 96 | 1.30E+06 | 1.93543 |
| 97 | 0 | 5.75546 |
| 98 | 0 | 11.5768 |
| 99 | 0 | 12.0346 |
| 100 | 0 | 10.4937 |
| 101 | 0 | 8.47931 |
| 102 | 1.30E+06 | 6.61292 |
| 103 | 0 | 9.15208 |
| 104 | 0 | 13.9887 |
| 105 | 0 | 13.7261 |
| 106 | 0 | 11.6751 |
| 107 | 0 | 9.30739 |
| 108 | 1.30E+06 | 7.20008 |
| 109 | 0 | 9.5767 |
| 110 | 0 | 14.3044 |
| 111 | 0 | 13.9689 |
| 112 | 0 | 11.8689 |
| 113 | 0 | 9.46813 |
| 114 | 0 | 7.33811 |
| 115 | 0 | 5.63941 |
| 116 | 0 | 4.35985 |
| 117 | 0 | 3.42759 |
| 118 | 0 | 2.76109 |
| 119 | 0 | 2.28857 |
| 120 | 0 | 1.95333 |

Figure 2:
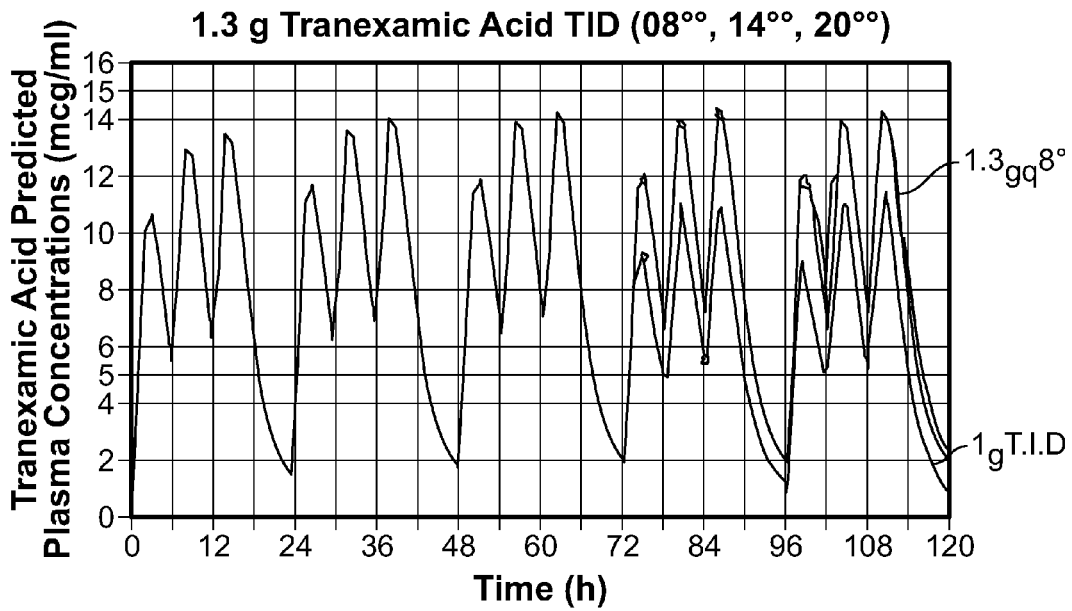
FIG. 2 depicts concentration-time profiles for simulated administration of the 1.3 g tranexamic acid modified release formulation of Example 1 at a TID (three times a day) dosing schedule of 8:00 AM, 2:00 PM, 8:00 PM comparing it with 1 g administered TID.

Concentration-time profiles are presented over 120 hours for the modified release formulation in Table 14 and are depicted in FIG. 2. A 1 g formulation administered TID is also depicted for comparison purposes.

TABLE 14

Cmax, Cmin and Cavg for 1.3 g TID
(8:00 AM, 2:00 PM, and 10:00 PM)
Simulation at 120 hours

| Pharmacokinetic Parameter | Conc. |
|---|---|
| Cmax | 12.0, 14.0, 14.3 mcg/mL |
| Cmin | 1.9, 6.6, 7.2 mcg/mL |
| Cavg | 8.4 mcg/mL |

Example 6

In Example 6, a study of a single dose followed by multiple doses, was performed on 20 healthy non-smoking adult female volunteers using a modified release formulation prepared in accordance with Example 1. After an overnight fast, subjects received a single oral dose of tranexamic acid (1.3 g) on Day 1. Blood samples were taken before dosing and up to 36 hours post-dose. Subjects received another single oral dose of tranexamic acid (1.3 g) on the evening of Day 2, and 3 times a day (every 8 hours) starting on the morning of Day 3 until the last dose on the morning of Day 7. Blood samples were taken before the 6th, 9th, 12th and 15th dose (the last dose) for the determination of $C_{min}$, and up to 8 hours after the last dose, for the determination of drug concentration at steady-state. Subjects were housed from at least 10 hours before the 1st dose on Day 1 until after the 8-hour blood draw following the 15th dose (on Day 7).

Tranexamic acid is minimally bound (approximately 3%) to plasma proteins (mainly plasminogen) at "typical" therapeutic plasma concentrations of approximately 5-15 mg/L. The main route of elimination of tranexamic acid is renal glomerular filtration. After oral administration of tranexamic acid (250 or 500 mg) to healthy adults, between 40-70% of the administered dose is excreted unchanged in the urine within 24 hours. After IV administration (1 g) 30% of the dose is excreted unchanged in the urine within one hour, 45-55% within 2-3 hours and 90% within 24 hours.

The beta elimination half-life of tranexamic acid is 2 hours. Based on published data, the mean $C_{max}$ and $AUC_{0-6}$ pharmacokinetic parameters after a single 1.3 g oral dose of tranexamic acid are expected to be approximately 65% of those achieved with a 2 g dose (i.e. ~10 mg/L and ~40 mg-h/L, $C_{max}$ and $AUC_{0-6}$ under fasting conditions, respectively).

However, the pharmacokinetics of tranexamic acid were not adequately characterized in Pilbrant, et al., *Eur. J. Clin. Pharmacol*, (1981)-20:65-72, since blood samples were collected for up to only 6 hours post-dose. In addition, the plasma concentration-time curves after IV administration showed three exponential phases, with a gamma elimination half-life of approximately 7 hours. For this reason, the concentration-time profile of tranexamic acid was estimated by simulating the data over 36 hours, after oral administration of a 1.3 g dose under fasting conditions, using NONMEM. Based on the simulation results, it would be appropriate to collect blood samples until 36 hours in order to characterize the AUC, Cmax, tmax, t½ and F.

The objective of this study of Example 6 was to assess the pharmacokinetic linearity of the test tablet formulation of tranexamic acid (modified release), after a single oral dose (Day 1) compared to a daily (1.3 g every 8 hours) dosage regimen (Days 2 to 7), under fasting conditions.

In the study of Example 6, blood samples (1×5 mL) were collected in blood collection tubes containing lithium heparin at Hour 0 (pre-dose) on Day 1, and at 0.5, 1, 1.5, 2, 2.5, 3, 3.5, 4, 5, 6, 8, 10, 14, 24, 28, 32, and 36 hours post-dose. Blood samples for Cmin determinations were also collected immediately before the 6th, 9th, 12th, and 15th doses on Days 4, 5, 6, and 7, respectively, and at the following times after the 15th dose: 0.5, 1, 1.5, 2, 2.5, 3, 3.5, 4, 5, 6, and 8 hours. Plasma samples were separated by centrifugation, then frozen at −20° C.±10° C. and kept frozen until assayed at AAI Development Services in New-Ulm, Germany.

Noncompartmental Pharmacokinetic Parameters

Calculations for plasma tranexamic acid were calculated by noncompartmental methods using the following pharmacokinetic parameters in Tables 15 and 16:

Day 1:

TABLE 15

| | |
|---|---|
| AUC 0-t: | The area under the plasma concentration versus time curve, from time 0 to the last measurable concentration, as calculated by the linear trapezoidal method. |
| AUCinf: | The area under the plasma concentration versus time curve from time 0 to infinity. AUCinf was calculated as the sum of AUC 0-t plus the ratio of the last measurable plasma concentration to the elimination rate constant. |
| AUC/AUCinf: | The ratio of AUC 0-t to AUCinf. |
| Cmax: | Maximum measured plasma concentration over the time span specified. |
| tmax: | Time of the maximum measured plasma concentration. If the maximum value occured at more than one time point, tmax was defined as the first time point with this value. |

TABLE 15-continued

| | |
|---|---|
| kel: | Apparent first-order terminal elimination rate constant calculated from a semi-log plot of the plasma concentration versus time curve. This parameter was calculated by linear least squares regression analysis using the maximum number of points in the terminal log-linear phase (e.g. three or more non-zero plasma concentrations). |
| t½: | The apparent first-order terminal elimination half-life was calculated as 0.693/kel. |

No value for kel, AUCinf or t½ were reported for cases that did not exhibit a terminal log-linear phase in the concentration versus time profile.

Day 7:

TABLE 16

| | |
|---|---|
| AUCτ: | The area under the plasma concentration versus time curve over the final dosing interval, as calculated by the linear trapezoidal method. |
| Cmax: | Maximum measured plasma concentration over the final dosing interval. |
| Cmin: | Measured plasma concentration prior to the morning dose. |
| tmax: | Time of the maximum measured plasma concentration over the final dosing interval. If the maximum value occurred at more than one time point, tmax was defined as the first time point with this value. |
| Flux: | Percent fluctuation was calculated as follows:<br>Flux 1:<br>$$\frac{Cmax - Cmin}{Cssav} \times 100$$<br>where Cssav was calculated as the ratio of AUC 0-τ to the dosing interval, τ.<br>Flux 2:<br>$$\frac{Cmax - Cmin}{Cmin} \times 100$$ |

Compartmental Pharmacokinetic Parameters

Compartmental analysis was performed on tranexamic acid data following single and multiple oral administrations of the modified release (MR) tablet formulation. Multiple compartmental models were constructed and their ability to fit plasma concentrations of tranexamic acid were evaluated using a standard two-stage (STS) approach with ADAPT-II (maximum likelihood analysis). The discrimination process was performed by computing the Akaike Information Criterion Test (AIC), the minimum value of the objective function (OBJ) and by looking at pertinent graphical representations of goodness of fit (e.g. fitted and observed concentrations versus time).

The final analysis was performed using an iterative two-stage approach with the IT2S® software. This software uses a population methodology which allows one to provide robust PK parameter estimates on an individual subject and population basis. All relevant pharmacokinetic parameters were calculated and reported. Concentrations were modeled using a weighting procedure of $W_j=1/S_j^2$ where the variance $\sigma j^2$ was calculated for each observation using the equation $\sigma j^2 = (a+b*Y_j)^2$ where a and b are the intercept and slope of each variance model. The slope is the residual variability associated with each concentration (includes the intra-individual variability and the sum of all experimental errors), and the intercept is related to the limit of detection of the analytical assay. All PK parameter estimates were updated iteratively during the population PK analysis (VARUP, IT2S®) until stable values were found. The analysis included the quantitative estimation of population PK parameters and interindividual variability of tranexamic acid in plasma.

Individual profiles of observed vs fitted plasma concentrations of tranexamic acid were provided for the MR formulation.

Statistical Analyses

Descriptive Statistics

Descriptive statistics including arithmetic means, standard deviations and coefficients of variation were calculated on the individual concentration and pharmacokinetic data. Additionally, geometric means were calculated for the parameters $AUC_{0-t}$, $AUC_{inf}$ and $C_{max}$ for Day 1 and AUCτ, $C_{max}$ and $C_{min}$ for Day 7.

Time Dependence Pharmacokinetic Linearity

The pharmacokinetic parameter AUCτ (Day 7) was compared against $AUC_{inf}$ (Day 1) using an analysis of variance (ANOVA) on the ln-transformed values for tranexamic acid. The ANOVA model included Group, Day (1 ($AUC_{inf}$) and 7 (AUCτ)) and the interaction Day*Group as fixed effects. All the interaction terms were not statistically significant, at a level of 5%, and were dropped from the final model. The ANOVA included calculation of least-squares means (LSM), the difference between Day LSM and the standard error associated with this difference. The above statistical analysis was done using the SAS® GLM procedure.

The ratio of LSM was calculated using the exponentiation of the Day LSM from the analysis on the ln-transformed response. The ratio was expressed as a percentage relative to $AUC_{inf}$(Day 1).

A ninety percent confidence interval for the ratio was derived by exponentiation of the confidence interval obtained for the difference between Day LSM resulting from the analysis on the ln-transformed response. The confidence interval was expressed as a percentage relative to $AUC_{inf}$(Day 1).

Steady-State Analysis

A steady-state analysis was performed, on the ln-transformed pre-dose Cmin concentrations at −72, −48, −24 and 0-hour time points, using Helmert's contrasts. The ANOVA model included Group, Time and the interaction Time*Group as fixed effects. In order to model the correlations within every subject, an appropriate variance-covariance matrix was chosen among the following: unstructured (UN), compound symmetry (CS), compound symmetry heterogeneous (CSH), variance component (VC), autoregressive (AR(1)), autoregressive heterogeneous (ARH(1)) and autoregressive moving average (ARMA(1,1)), using the Akaike's Burnham and Anderson criterion (AICC). All the interaction terms were not statistically significant, at a level of 5%, and were dropped from the final model. The ANOVA included also calculation of least-squares means (LSM) for each pre-dose $C_{min}$ concentrations. Helmert's contrasts were constructed such that each time point is compared to the mean of subsequent time points. There are 3 contrasts associated to the 4 pre-dose concentration timepoints. They are listed in Table 17 below:

TABLE 17

| Contrast | Tests |
|---|---|
| Compar. 1 | Predose Day 4 compared to (mean predose of Day 5, 6 and 7) |
| Compar. 2 | Predose Day 5 compared to (mean predose of Day 6 and 7) |
| Compar. 3 | Predose Day 6 compared to predose Day 7 (0-hour) |

The above statistical analyses were done using the SAS® Mixed procedure.

Formula

The following formulae in Table 18 were used for the ratio of least-squares means and 90% confidence interval calculations derived from the ANOVA on the ln transformed pharmacokinetic parameters.

TABLE 18

| | |
|---|---|
| Ratio of Least-squares Means: | $100 \times e^{(LSM_{Day7}-LSM_{Day1})}$ |
| 90% Confidence Interval: | $100 \times e^{(LSM_{Day7}-LSM_{Day1} \pm t_{df,0.05} \times SE_{Day7-Day1})}$ |

Note:
$LSM_{Day7}$ and $LSM_{Day1}$ are the least-squares means of Day 7 and Day 1, as computed by the LSMEANS statement of the SAS ® GLM procedure.
$t_{df,\alpha}$ is the value of the Student's t distribution with df degrees of freedom (i.e. degrees of freedom for the error term from the analysis of variance) and a right-tail fractional area of α ($\alpha = 0.05$).
$SE_{Day7-Day1}$ is the standard error of the difference between the adjusted Day means, as computed by the ESTIMATE statement in the SAS ® GLM procedure.

Discussion of Pharmacokinetic Results

Time Dependence Pharmacokinetic Linearity

The ANOVA model included Group, Day (1 ($AUC_{inf}$) and 7 ($AUC\tau$)) and the interaction Day*Group as the fixed effect. All the interaction terms were not statistically significant, at a level of 5%, and were dropped from the final model. Pharmacokinetic linearity was calculated for the formulation using the same approach as above, but the ANOVA model included Group, Day 1 (AUCinf) and Day 7 ($AUC\tau$)) and the interactions Group*Day as fixed effects and Subject nested within Group as a random effect.

The pharmacokinetic linearity results are summarized in the table below.

TABLE 19

| | | 90% Confidence Interval | |
|---|---|---|---|
| Formulation | Ratio AUCτ/AUCinf | Lower Limit | Upper Limit |
| MR | 97.3 | 86.5 | 109.5 |

The pharmacokinetic linearity results indicate that the ratios of least-squares means of $AUC\tau$ (Day 7) to $AUC_{inf}$ (Day 1) and the 90% confidence interval for the MR formulation were within the 80-125% acceptance range. Based on these results, the 650 mg tranexamic acid modified release tablets exhibited linear pharmacokinetics following repeated administration (7 days) of a 1.3 g dose under fasting conditions.

Steady-State Analysis

For the steady-state analysis, the CS variance-covariance matrix was chosen to model the correlations within every subject. Overall, the interaction term (i.e. Time*Group) was not statistically significant and was removed from the final ANOVA model. For each formulation, the same approach as above was used, but the ANOVA models included Group, Time and the interactions Time*Group as fixed effects.

A summary of LSM results for the steady-state analysis are summarized in Table 20A below.

TABLE 20A

| Formulation | Days | Times (hour) | LSM derived from the ANOVA |
|---|---|---|---|
| MR | 4 | −72 | 4.90536 |
| | 5 | −48 | 4.77323 |
| | 6 | −24 | 5.23678 |
| | 7 | 0 | 5.15389 |

Summary of statistical comparisons for the steady-state analysis are summarized in Table 20B below

TABLE 20B

| Formulation | Helmert's contrasts | P-value |
|---|---|---|
| MR | Predose Day 4 compared to (mean predose of Day 5, 6 and 7) | 0.4438 |
| | Predose Day 5 compared to (mean predose of Day 6 and 7) | 0.0393 |
| | Predose Day 6 compared to predose Day 7 | 0.7318 |

Based on the results above, steady-state plasma concentration of tranexamic acid were reached on Day 4 (−72-hour), since the p value for the first contrast was not statistically significant at a 5% alpha error. It should be noted that the second comparison [Predose Day 5 compared to (mean of Day 6 and 7)] was found to be statistically significant.

The largest difference observed in predose plasma concentrations of tranexamic acid between the LSM of predose Day 5 compared to Day 6 and 7 was less than 10%, which is not considered clinically relevant. Moreover, the last contrast was not statistically significant and the observed difference between the LSM of predose Day 6 and 7 was less than 2%.

Compartmental Pharmacokinetic Analysis

The mean apparent oral clearance (CL/F) of the MR formulation calculated with compartmental methods was 17.7 L/h (295 mL/min). Based on previous data reported in the literature, the group of Pilbrant, et al., have determined that the urinary recovery of tranexamic acid exceeded 95% of the dose administered. Considering the bioavailability of the MR formulation (Mean F: 44.9%, See Table 5), the systemic clearance (CL) of tranexamic acid (295 mL/min×0.449=123 mL/min) would be close to the glomerular filtration rate in healthy subjects (125 mL/min)5.

Using compartmental methods, the mean T½γ for the MR formulation was 16.6 hours. Similar values of terminal elimination half-life were previously reported in the literature. Pilbrant A., et al., Eur. J. Clin. Pharmacol (1981), 20: 65-72.

Following a single oral dose of 1.3 g of the MR formulation, the mean plasma concentrations of tranexamic acid observed at 28, 32, and 36 hours were 0.19724, 0.15672, and 0.13624 mcg/mL, respectively. Considering the therapeutic window of tranexamic acid (5-15 mcg/mL) and the very low plasma concentration levels observed at these timepoints, the terminal elimination half-life (T½γ) characterizing the slow decline of plasma concentrations should not play a clinically significant role in the frequency of drug administration.

Pharmacokinetic Conclusions

The pharmacokinetic linearity results indicate that the ratios of least-squares means of AUCτ (Day 7) to AUCinf (Day 1) and the 90% confidence interval for the MR formulation were within the 80-125% acceptance range. Based on these results, the 650 mg tranexamic acid modified release tablets exhibited linear pharmacokinetics following repeated administration (7 days) of a 1.3 g dose under fasting conditions.

Steady-state plasma concentrations of tranexamic acid for the modified-release tablets were reached on Day 4 (−72-hour), since the p-value for the first contrast was not statistically significant at a 5% alpha error The pharmacokinetics of tranexamic acid was properly described using a three compartment PK model with linear elimination. The absorption kinetic of the single-dose (Day 1) data of tranexamic acid for the MR formulation was best described using a mixed-order rate constant of absorption.

Plasma Pharmacokinetic Parameters for the modified release (MR) formulation of Tranexamic Acid on day 1 are listed in Table 21 below.

TABLE 21

|  | ln $AUC_{0-t}$* (mcg·h/ml) | ln $AUC_{inf}$* (mcg·h/ml) | ln $C_{max}$* (mcg/ml) | $T_{max}$ (h) | Half-life (h) | $K_{el}$ (1/h) |
|---|---|---|---|---|---|---|
| Mean | 74.571 | 76.875 | 13.176041 | 3.079 | 11.078 | 0.06443 |
| CV % | 31.3 | 30.4 | 33.1 | 25.0 | 16.9 | 18.3 |
| N | 19 | 19 | 19 | 19 | 19 | 19 |

*For ln-transformed parameters, the antilog of the mean (i.e. the geometric mean) is reported;
$AUC_{0-\tau}$ = AUC post dose (0-36 hours)

Plasma Pharmacokinetic Parameters for the modified release (MR) formulation of Tranexamic Acid on day 7 are listed in Table 22 below.

TABLE 22

|  | ln $AUC_\tau$* (mcg·h/ml) | ln $C_{max}$* (mcg/mL) | ln $C_{min}$* (mcg/ml) | $T_{max}$ (h) | Flux 1** (%) | Flux 2** (%) |
|---|---|---|---|---|---|---|
| Mean | 74.791 | 15.803509 | 5.157681 | 2.553 | 113.16 | 219.21 |
| CV % | 29.0 | 30.1 | 31.2 | 14.4 | 21.6 | 44.6 |
| N | 19 | 19 | 19 | 19 | 19 | 19 |

*For ln-transformed parameters, the antilog of the mean (i.e. the geometric mean) is reported; $AUC_\tau$ = AUC dosing interval (8 hours)
**Defined in Table 16

Menorrhagia Instrument

In clinical trials the primary goal is to obtain definitive evidence regarding the benefit to risk profile of the pharmacotherapy. One of the most challenging design tasks in studies of heavy menstrual bleeding which is a subjective complaint is the choice of efficacy endpoints or outcome measures. The Applicants have established two criteria for assessing the clinical relevance of the reduction in menstrual blood loss in the clinical efficacy studies. The first criterion was that the mean reduction in menstrual blood loss should be greater than 50 mL. The second criterion was based on the correlation between the reduction in menstrual blood loss and the subjects' perception of a meaningful symptomatic change, derived from blinded data from the measures of the Menorrhagia Instrument (MI) in the first treated menstrual period in the menstrual cycle during a controlled clinical study for safety and efficacy of tranexamic acid in heavy menstrual Bleeding. Analysis of the data for the symptomatic measures of the Menorrhagia Instrument (MI, measure six, FIG. 1) established that a menstrual blood loss reduction of at least 36 mL as defined by the alkaline hematin test was regarded as meaningful by the clinical patients. The mean reduction in menstrual blood loss in patients treated with a tranexamic acid formulation at 1.9 and at 3.9 g/day met both criteria for a clinically meaningful result. Data from Menorrhagia Instrument (MI, measure six, FIG. 1, which establishes that the treatment was meaningful to the patient provides the treating practitioner with an assessment of patient response to tranexamic acid therapy.

Example 7

Mennoraghia Impact Measure Validation

Objective measurements of menstrual blood loss are not practical in the healthcare setting, and they correlate poorly with a woman's subjective assessment of blood loss and its impact on quality of life [Warner 2004; National Collaborating Centre for Women's and Children's Health, 2007]. Menorrhagia is a subjective condition and may be practically defined as menstrual loss that is greater than the woman feels that she can reasonably manage. The amelioration of symptoms of heavy menstrual loss are practical efficacy benefits of the treatment are therefore important to measure and validate in a controlled clinical environment.

The MI was evaluated in a sub population of patients enrolled in a clinical trial designed to assess the safety and efficacy of modified release tranexamic acid formulations (Example 1) at an oral dose of 3.9 g administered daily for up to 5 days during each menstrual period. Two groups of patients were used to assess the MI, one group of patients were those diagnosed with menorrhagia and undergoing treatment. The second group was an age matched normal group. The sub-study was designed: to collect sufficient quantitative data to support the construct-related validation of the MI measures; to collect sufficient quantitative data to support the assessment of meaningful/important change in blood loss to the women; to conduct a test/retest evaluation of the instrument, and to address the reliability of the MI measures.

Study Methods

Development of the MI began with a review of the literature focusing on the methods used to collect qualitative data from menorrhagia patients. Qualitative interviews with patients determined which symptomatic concepts were most important to women and could be included in a draft Impact Measure. Cognitive debriefing interviews to evaluate patient understanding of items led to the synthesis of a patient-based instrument for assessing the impact of limitations caused by heavy menstrual bleeding. Published measures were used in the evaluation of the psychometric properties of the Menorrhagia Instrument to assess Construct-Related Validity. The reference measures include, the Ruta Menorrhagia Questionnaire [Ruta 1995] and the Medical Outcomes Study Short-Form 36 Item Health Status Instrument (SF-36) [Ware 1992]. Scoring of the standardized measures followed published algorithms, Table 23.

TABLE 23

Descriptions of Instruments used in this study

| Measure | Score Generated | Score Ranges |
| --- | --- | --- |
| Menorrhagia Impact Measure (MI) | Blood Loss Severity (Q1) | 1 (light) thru 4 (very heavy) |
| | Limitation | |
| | Work outside or inside the home (Q2) | 1 (not at all) thru 5 (extremely) |
| | Physical activities (Q3) | 1 (not at all) thru 5 (extremely) |
| | Social or leisure activities (Q4) | 1 (not at all) thru 5 (extremely) |
| | Activity list (Q5) | [Descriptive] |
| | Change in blood loss (follow-up) (Q6, 6a, 6b) | [15-pt scale: 0 = no change, 1-7 improve, 1-7 worse] |
| | Meaningful/important change (Q6c) | Y/N |
| Ruta Menorrhagia Questionnaire | Global | 0 (asymptomatic) - 42 (severe) |
| | Specific | |
| | Physical Function: Impact on work and daily activities (Q9 and Q10) | 0 (asymptomatic) - 6 (severe) |
| | Social Function: Impact on social and leisure activities and sex-life (Q11 and Q12) | 0 (asymptomatic) - 8 (severe) |
| SF-36 | Physical Functioning, Role-Physical, Bodily Pain General Health (can be combined to form Physical Health Component Score); Vitality, Social Functioning, Role-Emotional, Mental Health (can be combined to form Mental Health Component Score) | 0-100 (100 = minimal impairment) |

Study Design

A total of 262 women completed the MI. The MI measures 1 through 5 were administered after subject's baseline period and after the subsequent first, second, third and sixth treatment periods. The MI measure 6 was administered after the first treatment period only. For this validation study, only the data collected through Month 1 of treatment was included in the analyses for the treatment cohort. The MI measures 1-5 were administered at baseline and at the subsequent first and second non-treatment periods for the subjects in the normal cohort The MI measure 6 was administered and data collected, at Month 1 and Month 2. The Ruta Menorrhagia Questionnaire, SF-36 Health Survey and the MIQ were completed by the subject before visit procedures were performed. A subset of at least 50 subjects were asked to return to the study site 7 to 10 days after the baseline Visit but before the next menstrual period starts to complete the MI a second time.

Treatment Group

A total of 177 patients were enrolled into the sub-study. During this time period 28 patients withdrew consent, dropped-out, or did not properly complete MI and were non-evaluable. The 149 patients remaining were intended to be age matched. The majority of patients in the study were in their late 30's or early 40's. Because of the difficulty of enrolling sufficient numbers of women with normal menstrual periods in this age bracket 18 evaluable patients were not age matched. A total of 131 evaluable patients were age matched. A sub-set of 80 evaluable patients participated in the test/retest segment of the validation. Of these patients 11 were evaluable but not age matched. Data from all 80 patients were used for statistical evaluation of the test/re-test correlations.

Normal Group

A group of women with self reported normal menstrual bleeding comprised the pool of normal women eligible for age matching in the study. A normal was defined as all of the following: a menstrual cycle between 26 and 32 days long, and their last (most recently completed) menstrual period was seven days or less in duration, the heaviest bleeding was three days or less, and the woman classified the bleeding overall as "light" or "moderate" as opposed to "heavy" or "very heavy. Women with normal periods who were enrolled into the study served as age-match controls for women recruited into the treatment group. Un-matching and re-matching occurred throughout the enrollment period if participants in either group dropped out of the study, if better re-matching increased the total number of matched pairs, or if the age-matched woman with normal periods did not enroll in the study.

Five women enrolled in the study did not complete the study through Visit 3. Another five women who did complete the study became 'unmatched' as the Treatment Group participant they had been matched to became non-evaluable. The 131 women who completed the study and remained matched are the Validation Sample Normal Group. A total of 51 women completed the Retest.

The following Measures were summarized and statistically analyzed:

MI measure 1—Blood Loss Rating

MI measure 2—Limitation of Work Outside or Inside the Home

MI measure 3—Limitation of Physical Activities

MI measure 4—Limitation of Social or Leisure Activities

MI measure 6/6a/6b—Menstrual Blood Loss During Last Period

MI measure 6c—Meaningfulness of Change in Menstrual Blood Loss

The statistics include the counts (missing data), mean, standard deviation, median, inter-quartile range, and minimum/maximum values. Differences in these variables between the treatment and normal cohorts were assessed using analysis of variance.

A p-value <0.05 was required for significance using two-sided hypothesis tests; no p-value adjustments were made for the analysis of multiple endpoints. All analyses were performed under SPSS version 11.5 for Windows, and the Stuart-Maxwell test for homogeneity was performed using Stata version 9.0 for Windows.

Validation of the MI was conducted using standardized analytic procedures found in the FDA Draft Guidance on Patient Reported Outcomes for Use in Evaluating Medical Products for Labeling Claims and instrument review criteria developed by the Scientific Advisory Committee of the Medical Outcomes Trust.[1]

[1] Scientific Advisory Committee of the Medical Outcomes Trust. Assessing health status and quality-of-life instruments: attributes and review criteria. Qual Life Res. 2002; 11: 193-205

Evaluation of the Menorrhagia Instrument

The MI consisted of 4 individual measures (1-4) that were analyzed separately for validation. No summative scale was derived. Measure 5, served as descriptive of variables and did not undergo standard validation analyses. Measures 6, 6a and 6b dealt with menstrual blood loss relative to the previous menstrual period. The answers to the measures in the subparts of measure 6, were combined to produce a 15 point rating scale. The scale values range from −7 to +7 with −7 representing a very great deal worse menstrual blood loss than the previous period, and +7 representing a very great deal better menstrual blood loss than the previous period. The midpoint (0) represents the perception of about the same menstrual blood loss as the previous period.

Test-retest reliability assessed if items produced stable, reliable scores under similar conditions (Guttman, 1945). Reproducibility was evaluated in a subset of at least 50 from the treatment group and at least 50 from the normal group 7 to 10 days after the baseline visit using the intra-class correlation coefficient (ICC, see formula below). Values above 0.70 indicated the stability of an instrument over time. The following formula was used to compute the Intraclass Correlation Coefficient (ICC):

$$ICC = \frac{A^2 + B^2 + C^2}{A^2 + B^2 + D^2 - \left(\frac{C^2}{n}\right)}$$

where:
A=Standard deviation of baseline score
B=Standard deviation of Time 2 score
C=Standard deviation of change in score
D=mean of change in score
n=number of respondents The data for each of the measures was above 0.70. In the test population, n=88, values of 0.72 (0.60-0.81), 0.75 (0.64-0.83), 0.77 (0.67-0.84) and 0.76 (0.66-0.84) for measures 1 to 4 respectively. The aged matched normal values where n=51 were 0.77 (0.63-0.86), 0.67 (0.49-0.80), 0.75 (0.60-0.85) and 0.86 (0.77-0.92) respectively.

Construct-Related Validity was established when relationships among items, domains, and concepts conform to what was predicted by the conceptual framework for the instrument. This includes convergent, discriminant, and known-groups validity. Convergent and discriminant validity was present where measures of the same construct are more highly related and measures of different constructs were less related. To assess convergent and discriminant validity, Pearson's correlation coefficients were computed between each MI measure and items and scales from the SF-36 and the Ruta Menorrhagia Questionnaire included in the study design and administered at the same visit. The following hypotheses were tested:

The MI Blood Loss Measure (#1) will have a stronger association with the Ruta Menorrhagia Questionnaire (RMQ) than to the SF-36 subscales.

The MI Physical Activity Limitation Measure (#3) will have a stronger association with the RMQ Physical Function scale, the SF-36 Physical domain, the SF-36 Role-Physical domain, and SF-36 Physical Component Summary score than the Ruta Social, SF-36 Social, and SF-36 Vitality domains.

The MI Social/Leisure Activity Limitation will have a have stronger associations with the RMQ Social Function scale and the SF-36 Social Function domain than the RMQ Physical, the SF-36 Physical and SF-36 Bodily Pain domains.

For convergent validity, the correlations of MI measures with Ruta subscales, SF-36 subscales, and diary data are shown in Table 24. The Ruta global score was highly correlated with each MI measures (range 0.757-0.809). The correlations of items with the SF-36 subscales were low to moderate, which is to be expected since the SF-36 is not a disease-specific measure, but rather a more generic health status measure unable to detect differences between a normal population and a population of women with menorrhagia. The MI measures were more strongly correlated with the SF-36 Physical and Role Physical subscales than other SF-36 subscales.

TABLE 24

Correlations Between Menorrhagia Insrtument Patient Reported Outcome (PRO) Measures and Ruta/SF-36/Diary

| | MI measure 1 Blood Loss | MI measure 2 Limit work outside or inside home | MI measure 3 Limit physical activity | MI measure 4 Limit social or leisure activity |
|---|---|---|---|---|
| Ruta - Global | 0.767 (0.000) | 0.785 (0.000) | 0.807 (0.000) | 0.809 (0.000) |
| Ruta - Physical Fx | 0.512 (0.000) | 0.682 (0.000) | 0.646 (0.000) | 0.664 (0.000) |
| Ruta - Social Fx | 0.606 (0.000) | 0.634 (0.000) | 0.659 (0.000) | 0.683 (0.000) |
| SF-36 - Physical Fx | −0.229 (0.000) | −0.234 (0.000) | −0.264 (0.000) | −0.273 (0.000) |
| SF-36 - Social Fx | −0.118 (0.057) | −0.194 (0.002) | −0.200 (0.001) | −0.261 (0.000) |
| SF-36 - Role Physical | −0.200 (0.001) | −0.279 (0.000) | −0.258 (0.000) | −0.303 (0.000) |
| SF-36 - Vitality | −0.143 (0.021) | −0.193 (0.002) | −0.248 (0.000) | −0.250 (0.000) |
| SF-36 - Bodily Pain | −0.087 (0.163) | −0.168 (0.006) | −0.192 (0.002) | −0.205 (0.001) |
| SF-36 - PCS | −0.190 (0.002) | −0.271 (0.000) | −0.285 (0.000) | −0.275 (0.000) |

The data supported the hypothesis that the MI Blood Loss measure (#1) had a stronger association with the Ruta global score than to the SF-36 subscales. While the hypothesis that MI measure #3 (Physical Activity Limitation) would be strongly associated to the physical domains of the RMQ (r=0.65) and SF-36 (r=−0.26) was confirmed, this measure was also strongly correlated to the RMQ Social Functioning (r=0.66). MI measure #4 (Social or Leisure Activity Limitation) was highly correlated to the RMQ Social (r=0.68) and moderately associated with the SF-36 Social Functioning domain.

Known-groups validity determined the ability of the instrument to discriminate between groups of subjects known to be distinct. The ability of the MI items to discriminate among known groups was assessed by comparing the 4 items (1 thru 4) to responses from the two groups (treatment and normal) at baseline. Differences in these variables, between the treatment and normal groups, were assessed using analysis of variance. A p-value <0.05 was required for significance using two-sided hypothesis tests; no p-value adjustments was made for the analysis of multiple endpoints.

For each MI measure, the mean score for the treatment group was significantly different than the mean score for the normal group (p<0.001). The treatment group scores were higher for each individual measure, indicating greater limitation as a result of their excessive menstrual blood loss (see Table 25).

changed. In order to measure the MI items ability to detect change, longitudinal data were evaluated focusing primarily on the changes from baseline to month 1. Differences in proportions and comparisons between treatment and normal groups were compared using chi-square statistics (the Stuart-Maxwell test testing marginal homogeneity for all categories simultaneously). Cohen Effect Size statistics were also compared between the treatment and normal groups. The Cohen Effect Size was computed by taking the mean change in measure score (baseline to month 1) and dividing that by the standard deviation of mean baseline score[2].

[2] Cohen, J. J. (1988). Statistical power analysis for the behavioral sciences (p. 8). Erlbaum: Hillsdale, N.J.

Figure 8:
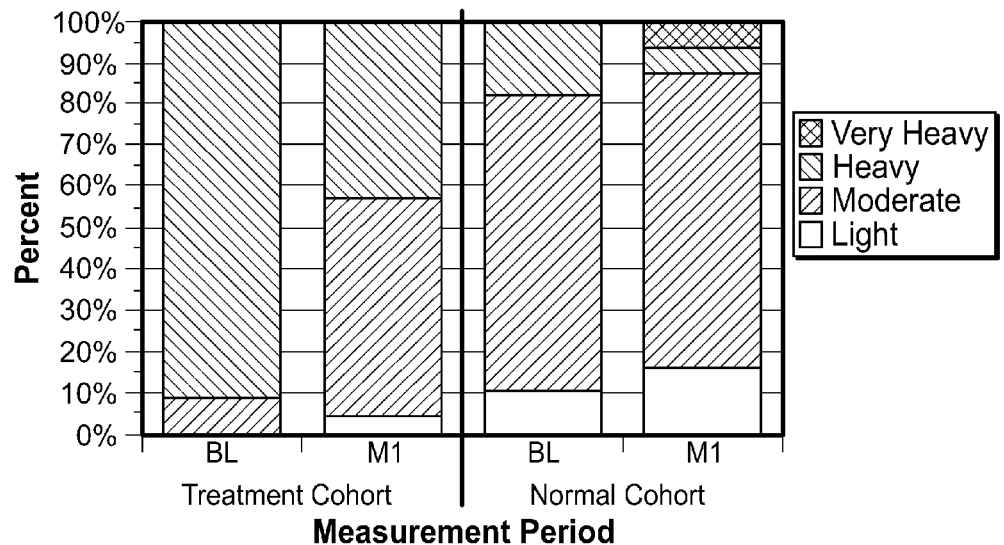
FIG. 8 is a graph of Menorrhagia Instrument measure #1 percentage of patients and normals indicating each response at baseline (BL) and at one (1) month (M1).
Figure 9:
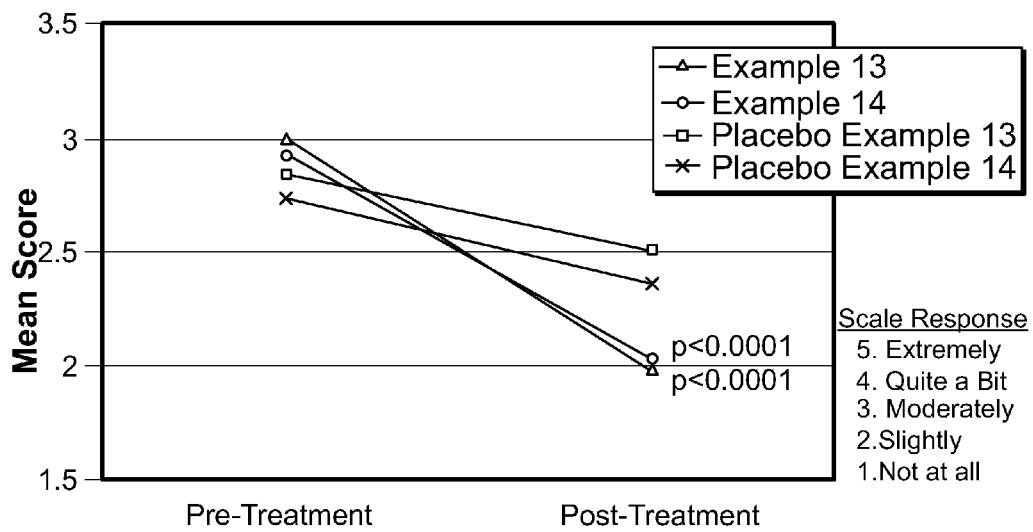
FIG. 9 is a graph of the limitations of social and leisure activities (LSLA) in women with Heavy Menstrual Bleeding (HMB) in accordance with the treatment regimens administered in Examples 8 and 9.
Figure 10:
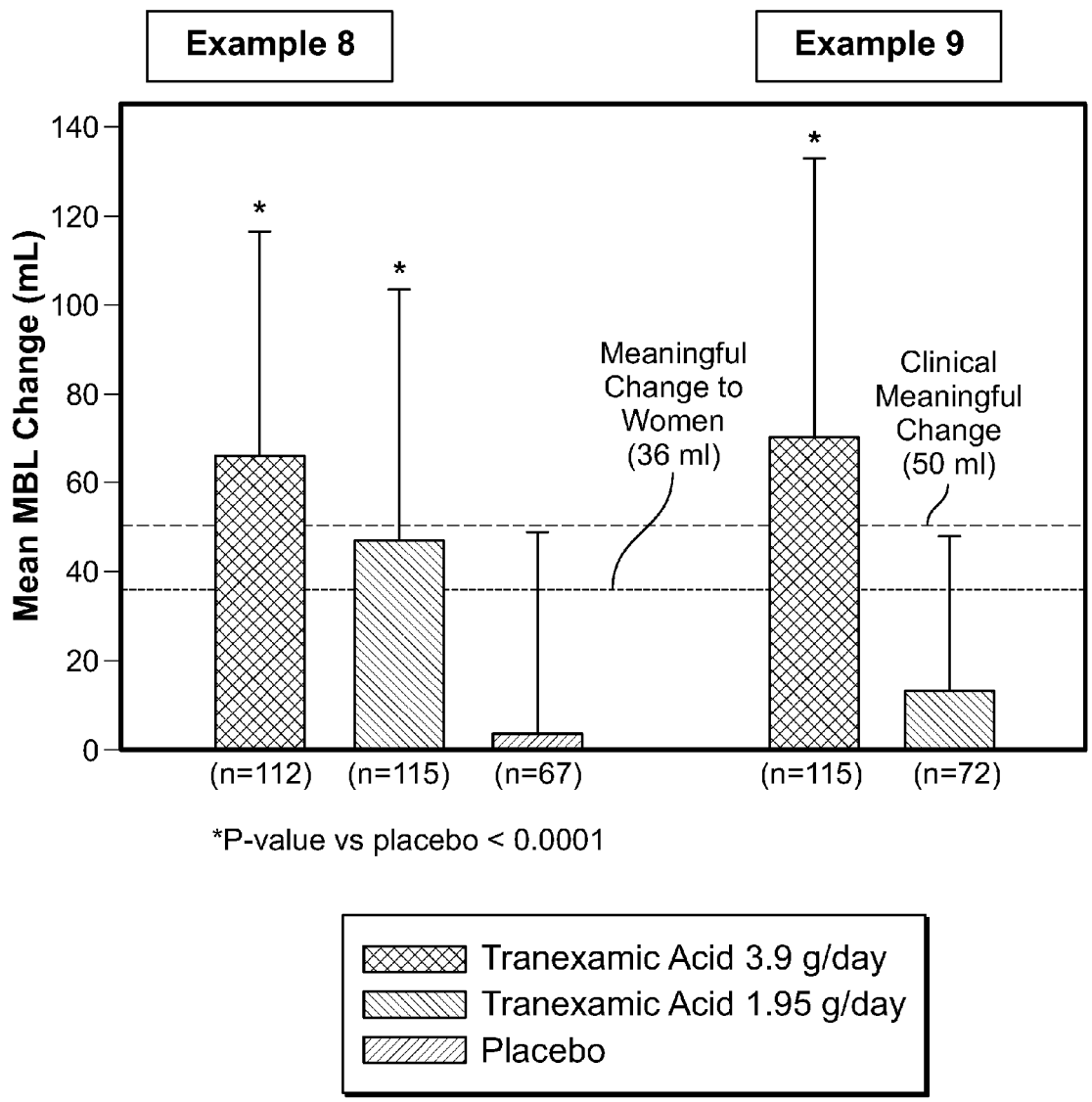
FIG. 10 is a graph of the mean menstrual blood loss change from the clinical studies of Examples 8 and 9.

Ability to detect change was described for each item in Tables 26A-D by indicating the distribution of baseline and month 1 response option pairs for all patients. Change in responses from baseline to month 1 was tested using the Stuart-Maxwell test. For the treatment group, there was significant change in responses to each measure from baseline to month one (p<0.001). For the normal group, none of the items had significant changes in responses from baseline to month one. FIG. 8 illustrates the distribution of responses to measure 1 at baseline and at month one. In the treatment group, the proportion reporting light or moderate bleeding as measured with item 1, increased from baseline to month 1, and in the normal group this proportion changed very little.

TABLE 25

Known-Groups Validity of the MIQ

| | | Treatment Cohort | | | AGE MATCH NORMAL Cohort | | | |
|---|---|---|---|---|---|---|---|---|
| | | N | Mean | St. Dev. | N | Mean | St. Dev. | F (sig.)[1] |
| MI measure 1 | Self-perceived blood loss | 131 | 3.25 | 0.61 | 131 | 2.10 | 0.61 | 234.727 (<0.001) |
| MI measure 2 | Limit you in your work | 131 | 3.04 | 0.99 | 131 | 1.34 | 0.59 | 286.864 (<0.001) |
| MI measure 3 | Limit you in your physical activities | 131 | 3.28 | 0.95 | 131 | 1.49 | 0.72 | 299.011 (<0.001) |
| MI measure 4 | Limit you in your social/leisure activities | 131 | 3.05 | 1.06 | 131 | 1.37 | 0.72 | 227.312 (<0.001) |

The ability to detect change required that values for the item or instrument change when the concept it measures

TABLE 26A

Sensitivity to change of the MI Measure 1

| | | | Month 1 | | | | |
|---|---|---|---|---|---|---|---|
| Cohort | | Response category | Light | Moderate | Heavy | Very Heavy | Stuart-Maxwell test of association |
| Treatment | Baseline | Light | 0 (0.0%) | 0 (0.0%) | 0 (0.0%) | 0 (0.0%) | 59.09 (p < 0.001) |
| | | Moderate | 0 (0.0%) | 8 (6.3%) | 4 (3.2%) | 0 (0.0%) | |
| | | Heavy | 3 (2.4%) | 41 (32.5%) | 24 (19.0%) | 2 (1.6%) | |
| | | Very Heavy | 2 (1.6%) | 18 (14.3%) | 13 (10.3%) | 11 (8.7%) | |
| Normal | Baseline | Light | 9 (6.9%) | 5 (3.8%) | 0 (0.0%) | 0 (0.0%) | 6.35 (p = 0.130) |
| | | Moderate | 12 (9.2%) | 77 (59.2%) | 4 (3.1%) | 0 (0.0%) | |

TABLE 26A-continued

Sensitivity to change of the MI Measure 1

| Cohort | Response category | Month 1 | | | | Stuart-Maxwell test of association |
|---|---|---|---|---|---|---|
| | | Light | Moderate | Heavy | Very Heavy | |
| | Heavy | 0 (0.0%) | 9 (6.9%) | 8 (6.2%) | 2 (1.5%) | |
| | Very Heavy | 0 (0.0%) | 2 (1.5%) | 2 (1.5%) | 0 (0.0%) | |

TABLE 26B

Sensitivity to change of the MI Measure 2

| Cohort | | Response category | Month 1 | | | | | Stuart-Maxwell test of association |
|---|---|---|---|---|---|---|---|---|
| | | | Not at all | Slightly | Moderately | Quite a bit | Extremely | |
| Treatment | Baseline | Not at all | 5 (4.0%) | 0 (0.0%) | 1 (0.8%) | 1 (0.8%) | 0 (0.0%) | 53.33 (p < 0.001) |
| | | Slightly | 12 (9.5%) | 11 (8.7%) | 2 (1.6%) | 1 (0.8%) | 0 (0.0%) | |
| | | Moderately | 17 (13.5%) | 26 (20.6%) | 14 (11.1%) | 1 (0.8%) | 0 (0.0%) | |
| | | Quite a bit | 2 (1.6%) | 8 (6.3%) | 5 (4.0%) | 9 (7.1%) | 0 (0.0%) | |
| | | Extremely | 3 (2.4%) | 3 (2.4%) | 3 (2.4%) | 1 (0.8%) | 1 (0.8%) | |
| Normal | Baseline | Not at all | 89 (69.0%) | 5 (3.9%) | 1 (0.8%) | 0 (0.0%) | 0 (0.0%) | 2.86 (p = 0.517) |
| | | Slightly | 8 (6.2%) | 13 (10.1%) | 4 (3.1%) | 2 (1.6%) | 0 (0.0%) | |
| | | Moderately | 0 (0.0%) | 3 (2.3%) | 4 (3.1%) | 0 (0.0%) | 0 (0.0%) | |
| | | Quite a bit | 0 (0.0%) | 0 (0.0%) | 0 (0.0%) | 0 (0.0%) | 0 (0.0%) | |
| | | Extremely | 0 (0.0%) | 0 (0.0%) | 0 (0.0%) | 0 (0.0%) | 0 (0.0%) | |

TABLE 26C

Sensitivity to change of the MI Measure 3

| Cohort | | Response category | Month 1 | | | | | Stuart-Maxwell test of association |
|---|---|---|---|---|---|---|---|---|
| | | | Not at all | Slightly | Moderately | Quite a bit | Extremely | |
| Treatment | Baseline | Not at all | 0 (0.0%) | 0 (0.0%) | 1 (0.8%) | 0 (0.0%) | 0 (0.0%) | 64.58 (p < 0.001) |
| | | Slightly | 12 (9.5%) | 12 (9.5%) | 1 (0.8%) | 1 (0.8%) | 0 (0.0%) | |
| | | Moderately | 14 (11.1%) | 20 (15.9%) | 11 (8.7%) | 3 (2.4%) | 0 (0.0%) | |
| | | Quite a bit | 6 (4.8%) | 17 (13.5%) | 9 (7.1%) | 5 (4.0%) | 0 (0.0%) | |
| | | Extremely | 5 (4.0%) | 2 (1.6%) | 2 (1.6%) | 3 (2.4%) | 2 (1.6%) | |
| Normal | Baseline | Not at all | 72 (55.4%) | 9 (6.9%) | 0 (0.0%) | 0 (0.0%) | 0 (0.0%) | 1.99 (p = 0.708) |
| | | Slightly | 14 (10.8%) | 18 (13.8%) | 3 (2.3%) | 1 (0.8%) | 0 (0.0%) | |
| | | Moderately | 0 (0.0%) | 6 (4.6%) | 4 (3.1%) | 1 (0.8%) | 0 (0.0%) | |
| | | Quite a bit | 0 (0.0%) | 1 (0.8%) | 1 (0.8%) | 0 (0.0%) | 0 (0.0%) | |
| | | Extremely | 0 (0.0%) | 0 (0.0%) | 0 (0.0%) | 0 (0.0%) | 0 (0.0%) | |

TABLE 26D

Sensitivity to change of the MI Measure 4

| Cohort | | Response category | Month 1 | | | | | Stuart-Maxwell test of association |
|---|---|---|---|---|---|---|---|---|
| | | | Not at all | Slightly | Moderately | Quite a bit | Extremely | |
| Treatment | Baseline | Not at all | 6 (4.8%) | 3 (2.4%) | 0 (0.0%) | 0 (0.0%) | 0 (0.0%) | 60.77 (p < 0.001) |
| | | Slightly | 16 (12.7%) | 10 (7.9%) | 0 (0.0%) | 2 (1.6%) | 0 (0.0%) | |
| | | Moderately | 19 (15.1%) | 14 (11.1%) | 12 (9.5%) | 2 (1.6%) | 1 (0.8%) | |
| | | Quite a bit | 5 (4.0%) | 14 (11.1%) | 4 (3.2%) | 6 (4.8%) | 0 (0.0%) | |
| | | Extremely | 3 (2.4%) | 4 (3.2%) | 1 (0.8%) | 3 (2.4%) | 1 (0.8%) | |
| Normal | Baseline | Not at all | 84 (64.6%) | 11 (8.5%) | 0 (0.0%) | 0 (0.0%) | 0 (0.0%) | 1.71 (p = 0.807) |
| | | Slightly | 10 (7.7%) | 14 (10.8%) | 2 (1.5%) | 0 (0.0%) | 0 (0.0%) | |
| | | Moderately | 0 (0.0%) | 4 (3.1%) | 2 (1.5%) | 0 (0.0%) | 0 (0.0%) | |
| | | Quite a bit | 0 (0.0%) | 0 (0.0%) | 0 (0.0%) | 2 (1.5%) | 0 (0.0%) | |
| | | Extremely | 1 (0.8%) | 0 (0.0%) | 0 (0.0%) | 0 (0.0%) | 0 (0.0%) | |

The amount of change in each item from baseline to month 1 is shown in Table 27. For the treatment group, the mean change in response from baseline to month 1 ranged from −0.76 to −1.16 for the four items. The calculated effect size shows this amount of change for each item ranged from −0.9 to −1.2. For the normal group, the mean change in response from baseline to month 1 ranged from 0.03 to −0.12 for the four items. The effect size for each item ranged from 0.053 to −0.197. This analysis shows a large response in patients undergoing treatment and little to no response in normal women who have received no treatment. This instrument is capable of identifying the perceived improvement in menstrual blood loss.

Responses from treatment group participants were divided based on two separate responder definitions. In the first definition, a responder was a patient indicating a one-category change in MI measure 1. In the second definition, a responder was a patient who entered the study as "Very heavy" or "Heavy" (MI measure 1) and then, following treatment (month 1), indicated being "Moderate" or "Light". When the treatment group was analyzed using the first responder definition, 69 (90%) of the 77 responders reported improvement and 63 (91%) of these rated this improvement as "a meaningful change". Thirty-five (71%) of the 49 non-responders reported improvement and 35 (92%) rated their change as "a meaningful change".

TABLE 27

Sensitivity to Change of MI Effect Size

| | | BASELINE | | | MONTH 1 | | | CHANGE | | | Effect Size[1] |
|---|---|---|---|---|---|---|---|---|---|---|---|
| | Menorrhagia Item | n | Mean | St Dev | n | Mean | St Dev | n | Mean | St Dev | |
| Item 1 | Self-perceived blood loss | 126 | 3.25 | 0.62 | 126 | 2.49 | 0.73 | 126 | −0.76 | 0.84 | −1.226 |
| Item 2 | Limit you in your work | 126 | 3.05 | 0.99 | 126 | 2.12 | 0.99 | 126 | −0.93 | 1.13 | −0.939 |
| Item 3 | Limit you in your physical activities | 126 | 3.29 | 0.95 | 126 | 2.13 | 1.00 | 126 | −1.16 | 1.17 | −1.221 |
| Item 4 | Limit you in your social/leisure activities | 126 | 3.06 | 1.06 | 126 | 2.00 | 1.04 | 126 | −1.06 | 1.19 | −1.000 |

| | | BASELINE | | | CHANGE | | | | | | Effect Size |
|---|---|---|---|---|---|---|---|---|---|---|---|
| | Menorrhagia Item | n | Mean | St Dev | n | Mean | n | Mean | St Dev | | |
| Item 1 | Self-perceived blood loss | 130 | 2.10 | 0.61 | 130 | 1.98 | 130 | −0.12 | 0.56 | | −0.197 |
| Item 2 | Limit you in your work | 129 | 1.32 | 0.57 | 129 | 1.35 | 129 | 0.03 | 0.50 | | 0.053 |
| Item 3 | Limit you in your physical activities | 130 | 1.49 | 0.72 | 130 | 1.43 | 130 | −0.06 | 0.57 | | −0.083 |
| Item 4 | Limit you in your social/leisure activities | 130 | 1.37 | 0.72 | 130 | 1.33 | 130 | −0.04 | 0.58 | | −0.056 |

When the treatment group was analyzed using the second responder definition, 57 (89%) of the 64 responders reported improvement, and 52 (91%) reported their change to be meaningful. Forty-seven (76%) of the 62 non-responders reported improvement, and 45 (90%) reported their change to be meaningful. Among the normal group, 96 (73%) of 130 patients reported no change. Twenty-one (16%) reported improvement, and 13 (10%) reported worsening. Of the patients reporting change, 15 (44%) rated the change as "a meaningful change".

For those women on treatment who reported a meaningful improvement (78.6%), MI items 3 and 4 showed the greatest treatment effect with improvements of 1.29 and 1.17, respectively. As expected, the majority of the Normal cohort (73.3%) reported no change in their menstrual period.

Example 8

The following clinical study was carried out in order to evaluate the efficacy and safety of tranexamic acid provided as an oral modified release formulation of Example 1 to reduce menstrual blood loss (MBL) in women with menorrhagia when administered during menstruation compared to placebo.

This was a multi-center, double-blind, placebo-controlled, parallel-group study. The study consisted of a screening phase of two (2) menstrual periods (no treatment) to determine eligibility, followed by a treatment phase spanning three (3) menstrual periods to assess the efficacy and safety of tranexamic acid during menstruation.

The primary objective of the study was to determine the efficacy of a 1.95 gm/day of tranexamic acid (650 mg orally three times daily, TID) and 3.9 gm/day of tranexamic acid (1.3 gm orally three times daily, TID) administered during menstruation for up to 5 days (maximum of 15 doses) to reduce menstrual blood loss in women with objective evidence of heavy menstrual bleeding.

The secondary objective of the study was to determine the improvement with administration of 1.95 gm/day or 3.9 gm/day of tranexamic acid in women with heavy menstrual bleeding in their symptoms including, Limitation in Social Leisure Activities (LSLA) and Limitation in Physical Activities (LPA) scores from the Menorrhagia Instrument Measures (FIG. 7). Further the objective was to determine the safety of the 1.95 gm/day and 3.9 gm/day of the modified release tranexamic acid formulation administered during menstruation.

Three treatment periods were averaged for the menstrual blood loss (MBL) primary efficacy evaluation (first, second, and third periods on treatment). All periods were evaluated for the secondary endpoints, and for safety of tranexamic acid at an oral dose of 1.3 gm or placebo administered three (3) times daily for up to five consecutive (5) days (maximum of 15 doses) during menstruation.

Criteria for Evaluation (Safety and Efficacy Assessments)

Efficacy Assessment

Menstrual blood loss (MBL) was assessed during the entire menstrual period by the alkaline hematin test (AHT) method. The Menorrhagia Instrument Measures (FIG. 7) were also administered immediately after each menstrual period under investigation. For the Primary Endpoint, the objective reduction in menstrual blood loss (MBL) during the entire menstrual period as assessed by the AHT Method was assessed.

For the Secondary Endpoints, the scores for Limitation in Social Leisure Activities (LSLA) and the scores for Limitation in Physical Activities (LPA) from the Menorrhagia Instrument Measures (MI), measures #4 and #3, respectively) were assessed.

For the Secondary Endpoints the data collected included at least; Menstrual Blood Loss (MBL) assessment score (MI measure 1), Limitation in Work Outside or Inside the Home (LWH) score (MI item 2), and subject assessment of meaningfulness score from the MI (measure 6) (used for the MBL responder analysis).

Efficacy Results

The efficacy results were based on the modified ITT (mITT) populations. Results from the analysis of other populations were very similar to those derived from the analysis of the mITT population, and do not alter the general conclusions presented below. The numbers of subjects in the mITT populations in the efficacy study are summarized in Table 28 below:

TABLE 28

Numbers of Subjects in mITT Populations in Pivotal Efficacy Studies

| Treatment | N |
| --- | --- |
| Placebo | 67 |
| Tranexamic acid (1.95 g/day) | 115 |
| Tranexamic acid (3.9 g/day) | 112 |

Primary Efficacy Endpoint

Subjects in both treatment groups experienced a significant reduction from baseline in mean MBL The mean reduction in MBL in subjects treated with the higher dose (3.9 g/day) was 65.3 mL, or 38.6% compared with the baseline value ($p<0.0001$). A smaller reduction was observed in subjects at the lower dose of 1.95 g/day (46.5 mL, 26.1%, $p<0.0001$). The reductions in both groups were statistically significant ($p<0.0001$) when compared with that in the placebo control group (2.98 mL).

Key Secondary Efficacy Endpoints

Significant treatment-related reductions from baseline in mean LSLA score and mean LPA score were observed. Other secondary efficacy endpoints provided supportive evidence of the efficacy of tranexamic acid. Specifically, subjects' assessments of MBL (MI item 1) and LWH (MI measure 2), were both significantly reduced for subjects in the 3.9 g/day tranexamic acid group compared with placebo. The number of patients responding to treatment was assessed. A responder was defined as a subject with a reduction in MBL and a subjective "meaningful" improvement according to the MI (measure 6c) after the first menstrual cycle during the treatment period. The proportion of responders in this study was 58.3% and 71.0% in the 1.95 and 3.9 g/day tranexamic acid groups respectively, compared with placebo response rate of 23.4% ($p<0.0001$ for both dose levels).

These results demonstrate that tranexamic acid at doses of 1.9 and 3.9 g/day ameliorates the symptoms associated with HMB, including at least limitations in social, leisure, and physical functioning. In addition, these results provide converging evidence that tranexamic acid modified-release tablets are efficacious in the treatment of HMB.

Heavy Menstrual Bleeding in Patients with Fibroids Included in Clinical Study of this Example Analyses was initiated to assess tranexaminc acid modified release tablets treatment effect stratified by the presence of fibroids at baseline. The primary goal of this analysis was to evaluate treatment-by-fibroids effect across variety of endpoints. The results of the analysis is found in the following Tables:

TABLE 29.1

Treatment-Induced Changes in MBL (mL) over Three Cycles of Therapy
Stratified by the Presence of Fibroids
MITT Population

| Treatment | Statistics | Baseline MBL (mL) | | Change in MBL from Baseline (mL) | | Percent Change in MBL from Baseline (mL) | |
|---|---|---|---|---|---|---|---|
| | | With Fibroids | Without Fibroids | With Fibroids | Without Fibroids | With Fibroids | Without Fibroids |
| Lysteda 3.9 | N Mean | 50 | 64 | 49 | 63 | 49 | 63 |
| | (SD) | 192 (93) | 149 (68) | −80 (57) | −54 (43) | −41 (18) | −38 (25) |
| | Median | 172 | 129 | −67 | −51 | −37 | −43 |
| Lysteda 1.95 | N Mean | 44 | 72 | 44 | 71 | 44 | 71 |
| | (SD) | 211 (151) | 157 (73) | −45 (69) | −47 (49) | −22 (31) | −27 (23) |
| | Median | 157 | 126 | −38 | −43 | −26 | −31 |
| Placebo | N Mean | 24 | 43 | 24 | 43 | 24 | 43 |
| | (SD) | 180 (93) | 139 (43) | −5 (66) | −2 (31) | +2 (25) | 0 (25) |
| | Median | 147 | 128 | 0 | −2 | 0 | −1 |

NOTE:
MEAN values for baseline cycles and in-treatment cycles are used in these calculations

TABLE 29.2

Treatment-Induced Changes in MBL (mL) over Three Cycles of Therapy
Stratified by the Presence of Fibroids
MITT Population

| Treatment | Statistics | Baseline MBL (mL) | | Change in MBL from Baseline (mL) | | Percent Change in MBL from Baseline (mL) | |
|---|---|---|---|---|---|---|---|
| | | With Fibroids | Without Fibroids | With Fibroids | Without Fibroids | With Fibroids | Without Fibroids |
| Lysteda 3.9 | N Mean | 50 | 64 | 142 | 179 | 142 | 179 |
| | (SD) | 192 (93) | 149 (68) | −79 (59) | −54 (49) | −41 (21) | −38 (29) |
| | Median | 172 | 129 | −68 | −55 | −41 | −43 |
| Lysteda 1.95 | N Mean | 44 | 72 | 125 | 209 | 125 | 209 |
| | (SD) | 211 (151) | 157 (73) | −50 (79) | −48 (56) | −25 (34) | −27 (30) |
| | Median | 157 | 126 | −45 | −45 | −29 | −33 |
| Placebo | N Mean | 24 | 43 | 70 | 124 | 70 | 124 |
| | (SD) | 180 (93) | 139 (43) | −1 (74) | −3 (42) | +3 (34) | −1 (32) |
| | Median | 147 | 128 | +3 | 0 | +1 | 0 |

NOTE:
MEAN baseline values are compared to the individual in-treatment cycles

TABLE 29.3

Percent of Subjects Reaching Specified MBL Reduction Targets over
Three Cycles of Therapy Stratified by the Presence of Fibroids
MITT Population

| Treatment | Statistics | Percent of subjects with >36 mL reduction in MBL | | Percent of subjects with >50 mL reduction in MBL | | Percent of subjects reaching normal range (<=80 mL) | |
|---|---|---|---|---|---|---|---|
| | | With Fibroids | Without Fibroids | With Fibroids | Without Fibroids | With Fibroids | Without Fibroids |
| Lysteda 3.9 | n/N (%) | 45/53 (84.9%) | 48/67 (71.6%) | 35/53 (66.0%) | 37/67 (55.2%) | 20/53 (37.7%) | 39/67 (58.2%)* |
| Lysteda 1.95 | n/N (%) | 24/45 (53.3%) | 41/73 (56.2%) | 19/45 (42.2%) | 30/73 (41.1%) | 9/45 (20.0%) | 24/73 (32.9%) |

TABLE 29.3-continued

Percent of Subjects Reaching Specified MBL Reduction Targets over
Three Cycles of Therapy Stratified by the Presence of Fibroids
MITT Population

| Treatment | Statistics | Percent of subjects with >36 mL reduction in MBL | | Percent of subjects with >50 mL reduction in MBL | | Percent of subjects reaching normal range (<=80 mL) | |
|---|---|---|---|---|---|---|---|
| | | With Fibroids | Without Fibroids | With Fibroids | Without Fibroids | With Fibroids | Without Fibroids |
| Placebo | n/N (%) | 1/24 (4.2%) | 8/45 (17.8%) | 1/24 (4.2%) | 5/45 (11.1%) | 4/24 (16.7%) | 8/45 (17.8%) |

NOTE:
MEAN values for baseline cycles and in-treatment cycles are used in these calculations

TABLE 29.4

Percent of Subjects Reaching Specified MBL Reduction Targets for
All Cycles of Therapy Stratified by the Presence of Fibroids
MITT Population

| Treatment | Statistics | Percent of subjects with >36 mL reduction in MBL | | | Percent of subjects with >50 mL reduction in MBL | | | Percent of subjects reaching normal range (<=80 mL) | | |
|---|---|---|---|---|---|---|---|---|---|---|
| | | With Fibroids | Without Fibroids | Total | With Fibroids | Without Fibroids | Total | With Fibroids | Without Fibroids | Total |
| Lysteda 3.9 | n/N (%) | 115/147 (78.2%) | 129/189 (68.3%) | 244/336 (72.6%) | 94/147 (64.0%) | 105/189 (55.6%) | 199/336 (59.2%) | 59/147 (40.1%) | 106/189 (56.1%) | 165/336 (49.1%) |
| Lysteda 1.95 | n/N (%) | 81/132 (61.4%) | 127/213 (59.6%) | 208/345 (60.3%) | 65/132 (49.2%) | 91/213 (42.7%) | 156/345 (45.2%) | 37/132 (28.0%) | 79/213 (37.1%) | 116/345 (33.6%) |
| Placebo | n/N (%) | 13/72 (18.1%) | 29/129 (22.5%) | 42/201 (20.9%) | 10/72 (13.9%) | 21/129 (16.3%) | 31/201 (15.4%) | 13/72 (18.1%) | 26/129 (20.2%) | 39/201 (19.4%) |

NOTE:
MEAN baseline values are compared to the individual in-treatment cycles

TABLE 30

Treatment-Induced Changes in MIQ Q1 over Three Cycles of Therapy
Stratified by the Presence of Fibroids
MITT Population

| Treatment | Statistics | Baseline Q1 | | Post-Baseline Q1 | | Change in Q1 from Baseline | |
|---|---|---|---|---|---|---|---|
| | | With Fibroids | Without Fibroids | With Fibroids | Without Fibroids | With Fibroids | Without Fibroids |
| Lysteda 3.9 | N Mean (SD) Median | 49 2.92 (0.61) 3.0 | 63 2.71 (0.63) 2.5 | 49 2.27 (0.57) 2.33 | 63 2.19 (0.71) 2.0 | 49 −0.65 (0.70) −0.67 | 63 −0.53 (0.80) −0.5 |
| Lysteda 1.95 | N Mean (SD) Median | 44 2.80 (0.63) 3.0 | 71 2.82 (0.56) 3.0 | 44 2.40 (0.67) 2.33 | 71 2.39 (0.62) 2.33 | 44 −0.39 (0.60) −0.33 | 71 −42 (0.65) −0.5 |
| Placebo | N Mean (SD) Median | 24 2.85 (0.52) 3.0 | 42 2.79 (0.61) 3.0 | 24 2.67 (0.54) 2.67 | 42 2.74 (0.53) 2.67 | 24 −0.18 (0.53) +0.25 | 42 −0.05 (0.84) 0.0 |

TABLE 30.1

Treatment-Induced Changes in MIQ Q2 over Three Cycles of Therapy
Stratified by the Presence of Fibroids
MITT Population

| Treatment | Statistics | Baseline Q2 | | Post-Baseline Q2 | | Change in Q2 from Baseline | |
|---|---|---|---|---|---|---|---|
| | | With Fibroids | Without Fibroids | With Fibroids | Without Fibroids | With Fibroids | Without Fibroids |
| Lysteda 3.9 | N Mean | 49 | 63 | 49 | 63 | 49 | 63 |
| | (SD) | 3.15 | 2.99 | 2.17 | 2.07 | −0.99 | −0.92 |
| | Median | (0.90) | (1.01) | (0.94) | (0.96) | (0.87) | (1.08) |
| | | 3.0 | 3.0 | 2.0 | 2.0 | −1.0 | −0.83 |
| Lysteda 1.95 | N Mean | 44 | 71 | 44 | 71 | 44 | 71 |
| | (SD) | 2.98 | 2.82 | 2.38 | 2.27 | −0.59 | −0.56 |
| | Median | (1.05) | (0.56) | (0.86) | (0.94) | (0.80) | (0.97) |
| | | 3.0 | 3.0 | 2.33 | 2.33 | −0.67 | −0.67 |
| Placebo | N Mean | 24 | 42 | 24 | 42 | 24 | 42 |
| | (SD) | 2.98 | 2.69 | 2.78 | 2.49 | −0.19 | −0.20 |
| | Median | (0.85) | (0.92) | (0.84) | (0.92) | (0.85) | (0.76) |
| | | 3.0 | 2.75 | 2.67 | 2.42 | 0.0 | −0.17 |

TABLE 30.2

Treatment-Induced Changes in MIQ Q3 over Three Cycles of Therapy
Stratified by the Presence of Fibroids
MITT Population

| Treatment | Statistics | Baseline Q3 | | Post-Baseline Q3 | | Change in Q3 from Baseline | |
|---|---|---|---|---|---|---|---|
| | | With Fibroids | Without Fibroids | With Fibroids | Without Fibroids | With Fibroids | Without Fibroids |
| Lysteda 3.9 | N Mean | 49 | 63 | 49 | 63 | 49 | 63 |
| | (SD) | 3.17 | 2.98 | 2.13 | 2.07 | −1.05 | −0.92 |
| | Median | (1.06) | (1.02) | (0.93) | (0.96) | (0.93) | (1.10) |
| | | 3.0 | 3.0 | 2.0 | 2.0 | −1.0 | −0.67 |
| Lysteda 1.95 | N Mean | 44 | 71 | 44 | 71 | 44 | 71 |
| | (SD) | 2.92 | 3.01 | 2.36 | 2.24 | −0.56 | −0.77 |
| | Median | (1.09) | (0.90) | (0.81) | (0.97) | (0.80) | (0.94) |
| | | 3.0 | 3.0 | 2.33 | 2.00 | −0.58 | −0.83 |
| Placebo | N Mean | 24 | 42 | 24 | 42 | 24 | 42 |
| | (SD) | 3.15 | 2.86 | 2.72 | 2.60 | −0.42 | −0.26 |
| | Median | (0.88) | (0.85) | (0.90) | (0.90) | (0.78) | (0.81) |
| | | 3.0 | 3.0 | 2.67 | 2.67 | −0.42 | 0.0 |

TABLE 30.3

Treatment-Induced Changes in MIQ Q4 over Three Cycles of Therapy
Stratified by the Presence of Fibroids
MITT Population

| Treatment | Statistics | Baseline Q3 | | Post-Baseline Q3 | | Change in Q3 from Baseline | |
|---|---|---|---|---|---|---|---|
| | | With Fibroids | Without Fibroids | With Fibroids | Without Fibroids | With Fibroids | Without Fibroids |
| Lysteda 3.9 | N Mean | 49 | 63 | 49 | 63 | 49 | 63 |
| | (SD) | 3.08 | 2.93 | 2.00 | 1.97 | −1.08 | −0.96 |
| | Median | (1.11) | (1.05) | (0.92) | (1.05) | (1.10) | (1.13) |
| | | 3.0 | 3.0 | 2.0 | 1.67 | −1.0 | −0.83 |
| Lysteda 1.95 | N Mean | 44 | 71 | 44 | 71 | 44 | 71 |
| | (SD) | 2.98 | 2.89 | 2.28 | 2.13 | −0.70 | −0.76 |
| | Median | (1.05) | (0.97) | (0.82) | (0.94) | (0.83) | (0.98) |
| | | 3.0 | 3.0 | 2.33 | 2.00 | −0.67 | −0.83 |
| Placebo | N Mean | 24 | 42 | 24 | 42 | 24 | 42 |
| | (SD) | 3.06 | 2.73 | 2.68 | 2.40 | −0.38 | −0.32 |
| | Median | (0.95) | (0.98) | (0.83) | (0.91) | (0.83) | (0.86) |
| | | 3.5 | 2.75 | 2.67 | 2.33 | −0.33 | −0.17 |

TABLE 30.5

Treatment-Induced Changes in MIQ Q6A-B at Cycle 1
Stratified by the Presence of Fibroids
MITT Population

| Treatment | Statistics | Change in Q6A-B from Baseline | | |
|---|---|---|---|---|
| | | With Fibroids | Without Fibroids | Total |
| Lysteda 3.9 | N | 46 | 59 | 105 |
| | Mean(SD) | 4.1 (2.4) | 3.1 (3.5) | 3.5 (3.1) |
| | Median | 5.0 | 3.0 | 4.0 |
| Lysteda 1.95 | N | 42 | 67 | 109 |
| | Mean(SD) | 2.8 (2.4) | 2.7 (3.2) | 2.7 (2.9) |
| | Median | 3.0 | 3.0 | 3.0 |
| Placebo | N | 24 | 40 | 64 |
| | Mean(SD) | −0.3 (3.6) | 0.8 (3.8) | 0.4 (3.8) |
| | Median | 0 | 0 | 0 |

NOTE:
MIQ items 6, 6a and 6b are combined into one scale ranging from −7 to +7. There are very strong reasons for this approach.

Example 9

The following clinical study was carried out in order to evaluate the efficacy and safety of the modified release (MR) oral formulation of tranexamic acid of Example 1 to reduce menstrual blood loss (MBL) in women with menorrhagia when administered during menstruation compared to placebo.

This was a multi-center, double-blind, placebo-controlled, parallel-group study. The study consisted of a screening phase of two (2) menstrual periods (no treatment) to determine eligibility, followed by a treatment phase spanning six (6) menstrual periods to assess the efficacy and safety of tranexamic acid during menstruation.

The primary objective of the study was to determine the efficacy of a 3.9 gm/day (1.3 gm orally three times daily, TID) administered during menstruation for up to 5 days (maximum of 15 doses) to reduce menstrual blood loss in women with objective evidence of heavy menstrual bleeding.

The secondary objective of the study included an evaluation of the improvement observed from 3.9 gm/day of the modified release tranexamic acid formulation administered during menstruation in women with heavy menstrual bleeding on Limitation in Social Leisure Activities (LSLA)(item 4) and Limitation in Physical Activities (LPA) (MI measure #3) scores from the Menorrhagia Instruments (FIG. 7). Four treatment periods were averaged for the menstrual blood loss (MBL) primary efficacy evaluation (first, second, third and sixth periods). All periods were evaluated for the secondary endpoints, the secondary endpoints, and for safety of tranexamic acid at an oral dose of 1.3 gm or placebo administered three (3) times daily for up to five consecutive (5) days (maximum of 15 doses) during menstruation.

Criteria for Evaluation

Menstrual blood loss (MBL) was assessed during the entire menstrual period by the alkaline hematin test (AHT) method. Measures from the Menorrhagia Instrument (FIG. 7) were also administered immediately after each menstrual period under investigation. Subjects reported large stains exceeding the capacity of sanitary protection (and other patient reported outcome [PRO] items) during the menstrual period in daily diaries.

For the Primary Endpoint, the objective reduction in menstrual blood loss (MBL) during the entire menstrual period as assessed by the AHT Method was assessed.

For the Secondary Endpoints, the Limitation in Social Leisure Activities (LSLA) and the Limitation in Physical Activities (LPA) scores from the Menorrhagia Instrument (MI measures #4 and #3, respectively) and the total number of large stains responder analysis during the menstrual period from subject diaries were assessed.

For the Secondary Endpoints, assessment of the following were included, Menstrual Blood Loss (MBL) assessment score (MI measure #1), Limitation in Work Outside or Inside the Home (LWH) score (MI measure #2), and subject assessment of meaningfulness score from the MI (Measure #6) (used for the MBL responder analysis).

Efficacy Results

The efficacy results were based on the modified ITT (mITT) populations. The numbers of subjects in the mITT populations in the efficacy study are summarized in the Table below:

TABLE 31

Numbers of Subjects in mITT Populations in Pivotal Efficacy Studies

| Treatment | N |
|---|---|
| Placebo | 72 |
| Tranexamic acid (3.9 g/day) | 115 |

Primary Efficacy Endpoint

Subjects experienced a significant reduction from baseline in mean MBL. The mean reduction in MBL in the tranexamic acid-treated subjects was 69.6 mL, or 40.4% compared with the baseline value ($p<0.0001$). The reduction in MBL was also statistically significant ($p<0.0001$) when compared with that in the placebo control group (12.6 mL, 8.2%).

Secondary Efficacy Endpoints

For the secondary efficacy endpoints, significant treatment-related reductions from baseline in mean LSLA score and mean LPA score were observed. Subjects' assessments of MBL (MI measure #1) and LWH (MI measure #2), were both significantly reduced for subjects in the 3.9 g/day tranexamic acid group compared with placebo.

The number of patients responding to treatment was assessed as described in the previous example. A responder was defined as a subject with a reduction in MBL and a subjective "meaningful" improvement according to the MI (measure #6c) after the first menstrual cycle during the treatment period. The proportion of responders increased in the 3.9 g/day tranexamic acid treatment group (65.4%) compared with the placebo group (31.8%, $p<0.0001$). These results demonstrate that 3.9 g/day tranexamic acid ameliorates the symptoms associated with HMB, including improvement in limitations in social, leisure, and physical functioning. In addition, these results provide converging evidence that tranexamic acid modified-release tablets are efficacious in the treatment of HMB.

In both the Example 9 and Example 10 studies, the reduction in menstrual blood loss (MBL) was evident in the first menstrual period after commencing treatment with 3.9 g/day tranexamic acid. The response to treatment was maintained for the duration of the study (three and six menstrual cycles in Example 9 and Example 10 respectively; Regression analysis in the study of Example VIII confirmed that the response to tranexamic acid was durable over the six menstrual cycles (regression slope of −0.90 mL/cycle, p=0.615).

Summary of Clinical Findings from the Studies of Examples 8 and 9

The efficacy and safety of the tranexamic acid (TXA MR) modified release tablets in the treatment of HMB was demonstrated in one 3-cycle treatment and one 6-cycle treatment, randomized, double-blind, placebo-controlled study. In these studies, the primary outcome measure was menstrual blood loss (MBL), measured using a validated menstrual blood loss method. The key secondary outcome measures were based on responses to items on the Menorrhagia Instrument (MI), a validated disease-specific patient-reported outcome instrument that measured Limitations in Social or Leisure activities and Limitations in Physical Activities. Large stains (soiling beyond the undergarment) and sanitary product use were also included as secondary outcome measures. In these studies, subjects were 18 to 49 years of age with a mean age of approximately 40 years and a BMI of approximately 32 kg/m2. On average, subjects had an HMB history of approximately 10 years and 40% had fibroids as determined by transvaginal ultrasound. About 20% were smokers and approximately 50% reported using alcohol. Approximately 70% were Caucasian, 25% were Black, and 5% were Asian, Native American, Pacific Islander, or Other. Seven percent (7%) of subjects were of Hispanic origin. In addition, approximately 18% of subjects were taking multivitamins and 7% of subjects were taking iron supplements.

Three-Cycle Treatment Study

This study compared the effects of two doses of tranexamic acid modified release tablets (1.95 g and 3.9 g given daily for up to 5 days during each menstrual period) versus placebo on MBL over a 3-cycle treatment duration. A total of 304 patients (117 TXA MR 1.95 g/day, 118 TXA MR 3.9 g/day, 69 Placebo) were randomized. MBL was significantly reduced in patients treated with 3.9 g/day TXA MR compared to placebo (mean 3.9 g/day TXA MR=65.31 mL [percent MBL reduction=38.6%]; placebo mean=2.98 mL [percent MBL reduction=1.9%]; p<0.0001). This reduction met the criteria for being a clinically meaningful improvement (MBL≧50 mL) and a meaningful improvement to women who participated in the trial (MBL≧36 mL). The 1.95 g/day dose did not meet the clinically meaningful improvement criteria for efficacy thereby establishing 3.9 g/day TXA MR as the minimally effective dose.

Tranexamic acid modified release tablets also significantly reduced limitations on social, leisure, and physical activities as measured by questions on the MI, and sanitary products used in the 3.9 g/day dose group compared to placebo (see Table 32). No significant treatment differences were observed in response rates on the number of large stains.

TABLE 32

Secondary Outcomes in 3-Cycle Study

| Outcome Measure | N | Mean (SD) Reduction* | P-value vs. Placebo |
|---|---|---|---|
| Social and Leisure Activities (MI) | | | |
| 3.9 gm/day TXA MR | 112 | 1.10 (1.12) | <0.0001 |
| Placebo | 66 | 0.34 (0.85) | |
| Physical Activities (MI) | | | |
| 3.9 gm/day TXA MR | 112 | 0.97 (1.03) | <0.0001 |
| Placebo | 66 | 0.32 (0.80) | |

TABLE 32-continued

Secondary Outcomes in 3-Cycle Study

| Outcome Measure | N | Mean (SD) Reduction* | P-value vs. Placebo |
|---|---|---|---|
| Sanitary Products Used | | | |
| 3.9 gm/day TXA MR | 112 | 6.36 (6.80) | <0.0001 |
| Placebo | 67 | 2.40 (6.13) | |
| Reduction in Large Stains** | | | |
| 3.9 gm/day TXA MR | 111 | 71 (64.0) | 0.156 |
| Placebo | 67 | 35 (52.2) | |

*Positive means reflect a decrease from baseline
**The reduction in large stains is reported as the number (%) of women who were classified as responders (i.e., subjects who experienced a positive change from baseline)

Six-Cycle Treatment Study

This study compared the effects of one dose of TXA MR (3.9 g/day) versus placebo on MBL over a 6-cycle treatment duration. A total of 196 patients (123 TXA MR 3.9 g/day, 73 Placebo) were randomized. Replicating the results from the 3-cycle treatment study, MBL was significantly reduced in patients treated with 3.9 g/day TXA MR compared to placebo (mean 3.9 g/day TXA MR=69.6 mL [percent MBL reduction=40.4%]; placebo mean=12.6 mL [percent MBL reduction=8.2%]; p<0.0001). This reduction met the criterion for being a clinically meaningful improvement (MBL≧50 mL) and a meaningful improvement to women (MBL≧36 mL). Limitations on social, leisure, and physical activities were also significantly reduced in the 3.9 g/day TXA MR dose group compared to placebo (see Table 33). No significant treatment differences were observed in sanitary products used or in response rates on the number of large stains.

TABLE 33

Secondary Outcomes in 6-Cycle Study

| Outcome Measure | N | Mean (SD) Reduction* | P-value vs. Placebo |
|---|---|---|---|
| Social and Leisure Activities (MI) | | | |
| 3.9 gm/day TXA MR | 115 | 0.89 (0.85) | <0.0001 |
| Placebo | 72 | 0.38 (0.82) | |
| Physical Activities (MI) | | | |
| 3.9 gm/day TXA MR | 115 | 0.90 (0.86) | <0.0001 |
| Placebo | 72 | 0.35 (0.90) | |
| Sanitary Products Used | | | |
| 3.9 gm/day TXA MR | 115 | 5.20 (6.39) | 0.129 |
| Placebo | 72 | 4.03 (5.94) | |
| Reduction in Large Stains** | | | |
| 3.9 gm/day TXA MR | 115 | 66 (57.4) | 0.453 |
| Placebo | 72 | 37 (51.4) | |

*Positive means reflect a decrease from baseline
**The reduction in large stains is reported as the number (%) of women who were classified as responders (i.e., subjects who experienced a positive change from baseline)

Example 10

Additional Pharmacokinetics

The pharmacokinetics of the modified release tranexamic acid tablets of Example 1 were further evaluated. After oral administration peak plasma levels ($C_{max}$) occurred at approximately 3 hours ($T_{max}$). The systemic bioavailability of the tablets in women aged 18-49 was approximately 45%. The mean $C_{max}$ and the area under the plasma concentration curve (AUC) remained unchanged after repeated (1.3 gm TID) oral dosing for 5 days as compared to a single 1.3 gm oral dose.

The $C_{max}$ and AUC after administration of a single 1.3 gm dose of tranexamic modified release tablets increased by 7% and 15% after food intake compared to fasting conditions, respectively. Therefore, the modified release tranexamic acid tablets can be taken with food.

The pharmacokinetic profile of the modified release tranexamic acid tablets was determined in 39 healthy women following a single 1.3 gm oral dose compared to repeated doses of 1.3 gm TID for 5 days. The results are shown in Table 34.

TABLE 34

| Parameter | 1 day | 5 days |
|---|---|---|
| Dose | 1.3 gm | 1.3 gm TID[a] |
| AUC (mcg * h/L) | 74.6[b] | 74.8[c] |
| Coefficient of variation | 33% | 30% |
| $C_{max}$ (mg/L) | 13.2 | 15.8 (5.2[d]) |
| $T_{max}$ (h) | 3.1 | 2.6 |
| $T_{1/2}$ (h)[e] | 11.1 | N/A |

Note:
Values represent geometric means, except Tmax which is the arithmetic mean.
[a]Dosed every 8 hours (3.9 g/day)
[b]$AUC_{0-t}$
[c]$AUC_t$
[d]$C_{min}$ corresponding steady-state concentration
[e]Reflects terminal half-life

CONCLUSION

While the invention herein disclosed has been described by means of specific embodiments and applications thereof, numerous modifications and variations could be made thereto by those skilled in the art without departing from the spirit and scope of the present invention. Such modifications are understood to be within the scope of the appended claims.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. A tranexamic acid tablet formulation, comprising:
   tranexamic acid or a pharmaceutically acceptable salt thereof; and
   a modified release material, wherein the modified release material comprises a polymer selected from the group consisting of hydroxyalkylcelluloses, alkylcelluloses, cellulose ethers, partial esters thereof, and mixtures thereof;
   wherein the modified release material is present in the formulation in an amount from about 10% to about 35% by weight of the formulation;
   wherein the formulation provides an in-vitro dissolution release rate of the tranexamic acid or pharmaceutically acceptable salt thereof, when measured by the USP 27 Apparatus Type II Paddle Method @ 50 RPM in 900 ml water at 37±0.5° C., of less than about 70% by weight tranexamic acid or pharmaceutically acceptable salt thereof released at about 45 minutes, and about 100% by weight tranexamic acid or pharmaceutically acceptable salt thereof released by about 120 minutes; and
   wherein each tablet of the formulation provides a dose of about 650 mg of tranexamic acid.

2. The tranexamic acid formulation of claim 1, wherein the formulation provides a mean in-vitro dissolution release rate of the tranexamic acid or pharmaceutically acceptable salt thereof, when measured by the USP 27 Apparatus Type II Paddle Method @ 50 RPM in 900 ml water at 37±0.5° C., of about 15% to about 29% by weight tranexamic acid or pharmaceutically acceptable salt thereof released at about 15 minutes, about 56% to about 69% by weight tranexamic acid or pharmaceutically acceptable salt thereof released at about 45 minutes, and about 89% to about 100% by weight tranexamic acid or pharmaceutically acceptable salt thereof released at about 90 minutes.

3. The tranexamic acid tablet formulation of claim 1, wherein the tablet is a matrix tablet which comprises a pre-granulated drug mixed together with the modified release material.

4. The tranexamic acid tablet formulation of claim 1, wherein the modified release material comprises a hydroxyalkylcellulose or a cellulose ether.

5. The tranexamic acid tablet formulation of claim 1, wherein the modified release material comprises hydroxypropylmethylcellulose.

6. The tranexamic acid tablet formulation of claim 1, wherein the modified release material is present in an amount of about 15% by weight of the formulation.

7. The tranexamic acid tablet formulation of claim 5, wherein the modified release material is present in an amount of about 15% by weight of the formulation.

8. The tranexamic acid tablet formulation of claim 1, wherein a single administration of the formulation comprising a dose of 1300 mg of tranexamic acid provides a mean maximum plasma concentration ($C_{max}$) of tranexamic acid in a range from about 9 mcg/ml to about 14.5 mcg/ml following the administration.

9. The tranexamic acid tablet formulation of claim 1, wherein administration of the formulation comprising a dose of 1300 mg of tranexamic acid three times daily provides a mean maximum plasma concentration ($C_{max}$) of tranexamic acid in a range from about 12.5 mcg/ml to about 25 mcg/ml after multi-dose administration.

10. The tranexamic acid tablet formulation of claim 1, wherein said formulation provides a mean $T_{max}$ at from about 2 hours to about 3.5 hours after single dose oral administration.

11. A tranexamic acid tablet formulation, comprising:
    tranexamic acid or a pharmaceutically acceptable salt thereof; and
    an effective amount of a modified release material, wherein the modified release material comprises a polymer selected from the group consisting of hydroxyalkylcelluloses, alkylcelluloses, cellulose ethers, partial esters thereof, and mixtures thereof;
    wherein the modified release material is present in the formulation in an amount from about 10% to about 35% by weight of the formulation;
    wherein the formulation releases from about 10% to about 25% by weight tranexamic acid or pharmaceutically acceptable salt thereof every 15 minutes when measured in vitro utilizing the USP 27 Apparatus Type II Paddle Method @ 50 RPM in 900 ml water at 37±0.5° C. such that about 100% of tranexamic acid or pharmaceutically acceptable salt thereof is released by about 120 minutes; and
    wherein each tablet of the formulation provides a dose of about 650 mg of tranexamic acid.

12. The tranexamic acid tablet formulation of claim 1, wherein administration of the formulation comprising a dose of 1300 mg of tranexamic acid three times daily provides a mean maximum plasma concentration ($C_{max}$) of about 10 mcg/ml to about 20 mcg/ml after multi-dose administration.

13. The tranexamic acid tablet formulation of claim 1, wherein a single administration of the formulation comprising a dose of 1300 mg of tranexamic acid provides a mean maximum plasma concentration ($C_{max}$) of tranexamic acid in a range from about 9 mcg/ml to about 17.5 mcg/ml.

14. The tranexamic acid tablet formulation of claim 5, wherein the hydroxypropylmethylcellulose is present in an amount of about 10% to about 35% by weight of the formulation.

15. The tranexamic acid tablet formulation of claim 14, wherein the hydroxypropylmethylcellulose is present in an amount of about 15% by weight of the formulation.

16. A tranexamic acid tablet formulation, comprising:
   tranexamic acid or a pharmaceutically acceptable salt thereof; and
   hydroxypropylmethylcellulose in an amount from about 10% to about 35% by weight of the formulation;
   wherein the formulation provides an in-vitro dissolution release rate of the tranexamic acid or pharmaceutically acceptable salt thereof, when measured by the USP 27 Apparatus Type II Paddle Method @ 50 RPM in 900 ml water at 37±0.5° C., of less than about 70% by weight tranexamic acid or pharmaceutically acceptable salt thereof released at about 45 minutes, and about 100% by weight tranexamic acid or pharmaceutically acceptable salt thereof released by about 120 minutes; and
   wherein each tablet of the formulation provides a dose of about 650 mg of tranexamic acid.

17. The tranexamic acid tablet formulation of claim 16, wherein the hydroxypropylmethylcellulose is present in an amount of about 15% by weight of the formulation.

18. A tranexamic acid tablet formulation according to claim 11, comprising:
   tranexamic acid or a pharmaceutically acceptable salt thereof; and
   hydroxypropylmethylcellulose in an amount from about 10% to about 35% by weight of the formulation;
   wherein the formulation releases from about 10% to about 25% by weight tranexamic acid or pharmaceutically acceptable salt thereof every 15 minutes when measured in vitro utilizing the USP 27 Apparatus Type II Paddle Method @ 50 RPM in 900 ml water at 37±0.5° C. such that about 100% of tranexamic acid or pharmaceutically acceptable salt thereof is released by about 120 minutes; and
   wherein each tablet of the formulation provides a dose of about 650 mg of tranexamic acid.

19. The tranexamic acid tablet formulation of claim 18, wherein the hydroxypropylmethylcellulose is present in an amount of about 15% by weight of the formulation.

* * * * *